(12) United States Patent
Park et al.

(10) Patent No.: US 10,667,712 B2
(45) Date of Patent: *Jun. 2, 2020

(54) WEARABLE MONITOR

(71) Applicant: iRhythm Technologies, Inc., San Francisco, CA (US)

(72) Inventors: Shena Hae Park, San Francisco, CA (US); Mark J. Day, San Francisco, CA (US); Frank Garcia, Redwood City, CA (US); Hung H. Ho, San Francisco, CA (US); Nicholas Hughes, Orinda, CA (US); Genaro S. Sepulveda, San Francisco, CA (US); Yuriko Tamura, San Mateo, CA (US)

(73) Assignee: iRhythm Technologies, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,224

(22) Filed: May 24, 2019

(65) Prior Publication Data

US 2019/0274574 A1    Sep. 12, 2019

Related U.S. Application Data

(63) Continuation of application No. 16/160,173, filed on Oct. 15, 2018, now Pat. No. 10,299,691, which is a
(Continued)

(51) Int. Cl.
*A61B 5/0408* (2006.01)
*A61B 5/0205* (2006.01)
(Continued)

(52) U.S. Cl.
CPC ........ *A61B 5/04087* (2013.01); *A61B 5/0006* (2013.01); *A61B 5/0022* (2013.01);
(Continued)

(58) Field of Classification Search
None
See application file for complete search history.

(56) References Cited

U.S. PATENT DOCUMENTS

| 1,497,079 A | 6/1924 | Gullborg |
| 2,179,922 A | 11/1939 | Dana |

(Continued)

FOREIGN PATENT DOCUMENTS

| AU | 2011252998 | 8/2015 |
| AU | 2014209376 | 6/2017 |

(Continued)

OTHER PUBLICATIONS

US 8,750,980 B2, 06/2014, Katra et al. (withdrawn)
(Continued)

*Primary Examiner* — Brian T Gedeon
(74) *Attorney, Agent, or Firm* — Knobbe, Martens, Olson & Bear, LLP

(57) ABSTRACT

The present disclosure relates to a wearable monitor device and methods and systems for using such a device. In certain embodiments, the wearable monitor records cardiac data from a mammal and extracts particular features of interest. These features are then transmitted and used to provide health-related information about the mammal.

20 Claims, 25 Drawing Sheets

Related U.S. Application Data continuation of application No. 15/966,258, filed on Apr. 30, 2018, now Pat. No. 10,098,559, which is a continuation of application No. 15/463,944, filed on Mar. 20, 2017, now Pat. No. 9,955,887, which is a continuation of application No. 14/929,121, filed on Oct. 30, 2015, now Pat. No. 9,597,004.

(60) Provisional application No. 62/073,910, filed on Oct. 31, 2014.

(51) Int. Cl.

| | | |
|---|---|---|
| A61B 5/04 | (2006.01) | |
| A61B 5/0456 | (2006.01) | |
| A61B 5/046 | (2006.01) | |
| A61B 5/0472 | (2006.01) | |
| A61B 5/00 | (2006.01) | |
| A61B 5/0432 | (2006.01) | |
| G16H 40/63 | (2018.01) | |
| A61B 5/0468 | (2006.01) | |
| G16H 50/30 | (2018.01) | |
| G16H 50/20 | (2018.01) | |
| G16H 80/00 | (2018.01) | |
| A61B 7/04 | (2006.01) | |
| G06F 19/00 | (2018.01) | |
| G16H 40/67 | (2018.01) | |
| A61B 5/024 | (2006.01) | |
| A61B 5/0404 | (2006.01) | |

(52) U.S. Cl.
CPC ............ *A61B 5/0205* (2013.01); *A61B 5/046* (2013.01); *A61B 5/04012* (2013.01); *A61B 5/04015* (2013.01); *A61B 5/0456* (2013.01); *A61B 5/0468* (2013.01); *A61B 5/0472* (2013.01); *A61B 5/04325* (2013.01); *A61B 5/4839* (2013.01); *A61B 5/6832* (2013.01); *A61B 7/04* (2013.01); *G06F 19/00* (2013.01); *G06F 19/3418* (2013.01); *G16H 40/63* (2018.01); *G16H 40/67* (2018.01); *G16H 50/20* (2018.01); *G16H 50/30* (2018.01); *G16H 80/00* (2018.01); *A61B 5/02416* (2013.01); *A61B 5/02438* (2013.01); *A61B 5/0404* (2013.01); *A61B 5/04014* (2013.01); *A61B 5/6833* (2013.01); *A61B 5/6843* (2013.01); *A61B 5/7282* (2013.01); *A61B 2560/0209* (2013.01); *A61B 2560/0412* (2013.01); *A61B 2560/0468* (2013.01); *A61B 2562/0219* (2013.01)

(56) References Cited

U.S. PATENT DOCUMENTS

| | | |
|---|---|---|
| 2,201,645 A | 5/1940 | Epner |
| 2,311,060 A | 2/1943 | Lurrain |
| 2,500,840 A | 3/1950 | Lyons |
| 3,215,136 A | 11/1965 | Holter et al. |
| 3,547,107 A | 12/1970 | Chapman et al. |
| 3,870,034 A | 3/1975 | James |
| 3,882,853 A | 5/1975 | Gofman |
| 3,911,906 A | 10/1975 | Reinhold |
| 4,023,312 A | 5/1977 | Stickney |
| 4,027,664 A | 6/1977 | Heavner, Jr. et al. |
| 4,121,573 A | 10/1978 | Crovella et al. |
| 4,123,785 A | 10/1978 | Cherry et al. |
| 4,126,126 A | 11/1978 | Bare |
| 4,202,139 A | 5/1980 | Hong et al. |
| 4,274,419 A | 6/1981 | Tam et al. |
| 4,274,420 A | 6/1981 | Hymes |
| 4,286,610 A | 9/1981 | Jones |
| 4,333,475 A | 6/1982 | Moreno et al. |
| 4,361,990 A | 12/1982 | Link |
| 4,381,792 A | 5/1983 | Busch |
| 4,438,767 A | 3/1984 | Nelson |
| 4,459,987 A | 7/1984 | Pangburn |
| 4,535,783 A | 8/1985 | Marangoni |
| 4,537,207 A | 8/1985 | Gilhaus |
| 4,572,187 A | 2/1986 | Schetrumpf |
| 4,621,465 A | 11/1986 | Pangburn |
| 4,658,826 A | 4/1987 | Weaver |
| 4,712,552 A | 12/1987 | Pangburn |
| 4,736,752 A | 4/1988 | Munck et al. |
| 4,925,453 A | 5/1990 | Kannankeril |
| 4,938,228 A | 7/1990 | Righter et al. |
| 4,981,141 A | 1/1991 | Segalowitz |
| 5,003,987 A | 4/1991 | Grinwald |
| 5,027,824 A | 7/1991 | Dougherty et al. |
| 5,082,851 A | 1/1992 | Appelbaum et al. |
| 5,086,778 A | 2/1992 | Mueller et al. |
| 5,191,891 A | 3/1993 | Righter |
| 5,205,295 A | 4/1993 | Del Mar et al. |
| 5,226,425 A | 7/1993 | Righter |
| 5,228,450 A | 7/1993 | Sellers |
| 5,230,119 A | 7/1993 | Woods et al. |
| 5,289,824 A | 3/1994 | Mills et al. |
| 5,305,746 A | 4/1994 | Fendrock |
| 5,309,909 A | 5/1994 | Gadsby |
| 5,365,935 A | 11/1994 | Righter et al. |
| 5,458,141 A | 10/1995 | Neil |
| 5,483,967 A | 1/1996 | Ohtake |
| 5,489,624 A | 2/1996 | Kantner et al. |
| 5,511,553 A | 4/1996 | Segalowitz |
| 5,515,858 A | 5/1996 | Myllymaki |
| 5,536,768 A | 7/1996 | Kantner et al. |
| 5,581,369 A | 12/1996 | Righter et al. |
| 5,626,140 A | 5/1997 | Feldman et al. |
| 5,634,468 A | 6/1997 | Platt et al. |
| 5,645,063 A | 7/1997 | Straka |
| 5,645,068 A | 7/1997 | Mezack et al. |
| 5,730,143 A | 3/1998 | Schwarzberg |
| 5,749,365 A | 5/1998 | Magill |
| 5,749,367 A | 5/1998 | Gamlyn et al. |
| 5,771,524 A | 6/1998 | Woods et al. |
| 5,776,072 A | 7/1998 | Hsu et al. |
| 5,881,743 A | 3/1999 | Nadel |
| 5,916,239 A | 6/1999 | Geddes et al. |
| 5,931,791 A | 8/1999 | Saltzstein et al. |
| 5,941,829 A | 8/1999 | Saltzstein et al. |
| 5,957,854 A | 9/1999 | Besson et al. |
| 5,959,529 A | 9/1999 | Kail |
| 6,013,007 A | 1/2000 | Root et al. |
| 6,032,060 A | 2/2000 | Carim |
| 6,038,469 A | 3/2000 | Karlsson et al. |
| 6,044,515 A | 4/2000 | Zygmont |
| 6,093,146 A | 7/2000 | Filangeri |
| D429,336 S | 8/2000 | Francis et al. |
| 6,102,856 A | 8/2000 | Groff et al. |
| 6,117,077 A | 9/2000 | Del Mar et al. |
| 6,132,371 A | 10/2000 | Dempsey et al. |
| 6,134,480 A | 10/2000 | Minogue |
| 6,136,008 A | 10/2000 | Becker et al. |
| 6,161,036 A | 12/2000 | Matsumura et al. |
| 6,169,915 B1 | 1/2001 | Krumbiegel et al. |
| 6,178,357 B1 | 1/2001 | Gliner et al. |
| 6,200,265 B1 | 3/2001 | Walsh et al. |
| 6,225,901 B1 | 5/2001 | Kail |
| 6,232,366 B1 | 5/2001 | Wang et al. |
| 6,238,338 B1 | 5/2001 | DeLuca et al. |
| 6,248,115 B1 | 6/2001 | Halk |
| 6,287,252 B1 | 9/2001 | Lugo |
| 6,290,707 B1 | 9/2001 | Street |
| 6,315,719 B1 | 11/2001 | Rode et al. |
| 6,379,237 B1 | 4/2002 | Gordon |
| 6,385,473 B1 | 5/2002 | Haines et al. |
| 6,389,308 B1 | 5/2002 | Shusterman |
| 6,416,471 B1 | 7/2002 | Kumar et al. |
| 6,434,410 B1 | 8/2002 | Cordero et al. |
| 6,441,747 B1 | 8/2002 | Khair et al. |
| 6,454,708 B1 | 9/2002 | Ferguson et al. |

(56) References Cited

U.S. PATENT DOCUMENTS

| | | |
|---|---|---|
| 6,456,872 B1 | 9/2002 | Faisandier |
| 6,464,815 B1 | 10/2002 | Beaudry |
| 6,493,898 B1 | 12/2002 | Woods et al. |
| 6,496,705 B1 | 12/2002 | Ng et al. |
| 6,510,339 B2 | 1/2003 | Kovtun et al. |
| 6,546,285 B1 | 4/2003 | Owen et al. |
| 6,564,090 B2 | 5/2003 | Taha et al. |
| 6,569,095 B2 | 5/2003 | Eggers |
| 6,577,893 B1 | 6/2003 | Besson et al. |
| 6,580,942 B1 | 6/2003 | Willshire |
| 6,585,707 B2 | 7/2003 | Cabiri et al. |
| 6,589,170 B1 | 7/2003 | Flach et al. |
| 6,589,187 B1 | 7/2003 | Dimberger et al. |
| 6,605,046 B1 | 8/2003 | Del Mar et al. |
| 6,615,083 B2 | 9/2003 | Kupper |
| 6,622,035 B1 | 9/2003 | Merilainen |
| 6,626,865 B1 | 9/2003 | Prisell |
| 6,656,125 B2 | 12/2003 | Misczynski et al. |
| 6,664,893 B1 | 12/2003 | Eveland et al. |
| 6,665,385 B2 | 12/2003 | Rogers et al. |
| 6,690,959 B2 | 2/2004 | Thompson |
| 6,694,177 B2 | 2/2004 | Eggers et al. |
| 6,701,184 B2 | 3/2004 | Henkin |
| 6,711,427 B1 | 3/2004 | Ketelhohn |
| 6,730,028 B2 | 5/2004 | Eppstein |
| 6,773,396 B2 | 8/2004 | Flach et al. |
| 6,775,566 B2 | 8/2004 | Nissila |
| 6,801,137 B2 | 10/2004 | Eggers |
| 6,801,802 B2 | 10/2004 | Sitzman et al. |
| 6,871,089 B2 | 3/2005 | Korzinov et al. |
| 6,871,211 B2 | 3/2005 | Labounty et al. |
| 6,875,174 B2 | 4/2005 | Braun et al. |
| 6,881,191 B2 | 4/2005 | Oakley et al. |
| 6,893,396 B2 | 5/2005 | Schulze et al. |
| 6,897,788 B2 | 5/2005 | Khair et al. |
| 6,925,324 B2 | 8/2005 | Shusterman |
| 6,940,403 B2 | 9/2005 | Kail |
| 6,954,163 B2 | 10/2005 | Toumazou et al. |
| 6,957,107 B2 | 10/2005 | Rogers et al. |
| 6,987,965 B2 | 1/2006 | Ng et al. |
| 7,002,468 B2 | 2/2006 | Eveland et al. |
| 7,020,508 B2 | 3/2006 | Stivoric et al. |
| 7,024,248 B2 | 4/2006 | Penner et al. |
| 7,072,708 B1 | 7/2006 | Andresen et al. |
| 7,072,709 B2 | 7/2006 | Xue |
| 7,076,283 B2 | 7/2006 | Cho et al. |
| 7,076,287 B2 | 7/2006 | Rowlandson |
| 7,076,288 B2 | 7/2006 | Skinner |
| 7,076,289 B2 | 7/2006 | Sarkar et al. |
| 7,079,977 B2 | 7/2006 | Osorio et al. |
| 7,082,327 B2 | 7/2006 | Houben |
| 7,089,048 B2 | 8/2006 | Matsumura et al. |
| 7,099,715 B2 | 8/2006 | Korzinov et al. |
| 7,117,031 B2 | 10/2006 | Lohman et al. |
| 7,120,485 B2 | 10/2006 | Glass et al. |
| 7,130,396 B2 | 10/2006 | Rogers et al. |
| 7,161,484 B2 | 1/2007 | Tsoukalis |
| 7,171,166 B2 | 1/2007 | Ng et al. |
| 7,179,152 B1 | 2/2007 | Rhoades |
| 7,186,264 B2 | 3/2007 | Liddicoat et al. |
| 7,193,264 B2 | 3/2007 | Lande |
| 7,194,300 B2 | 3/2007 | Korzinov |
| 7,206,630 B1 | 4/2007 | Tarler |
| 7,212,850 B2 | 5/2007 | Prystowsky et al. |
| 7,222,054 B2 | 5/2007 | Geva |
| 7,242,318 B2 | 7/2007 | Harris |
| 7,266,361 B2 | 9/2007 | Burdett |
| 7,316,671 B2 | 1/2008 | Lastovich et al. |
| 7,349,947 B1 | 3/2008 | Slage et al. |
| 7,354,423 B2 | 4/2008 | Zelickson et al. |
| 7,387,607 B2 | 6/2008 | Holt et al. |
| 7,444,177 B2 | 10/2008 | Nazeri |
| 7,477,933 B2 | 1/2009 | Ueyama |
| 7,478,108 B2 | 1/2009 | Townsend et al. |
| 7,481,772 B2 | 1/2009 | Banet |
| 7,482,314 B2 | 1/2009 | Grimes et al. |
| 7,502,643 B2 | 3/2009 | Farringdon et al. |
| 7,539,533 B2 | 5/2009 | Tran |
| 7,542,878 B2 | 6/2009 | Nanikashvili |
| 7,587,237 B2 | 9/2009 | Korzinov et al. |
| 7,630,756 B2 | 12/2009 | Linker |
| 7,632,174 B2 | 12/2009 | Gringer et al. |
| 7,672,714 B2 | 3/2010 | Kuo et al. |
| 7,715,905 B2 | 5/2010 | Kurzweil et al. |
| 7,729,753 B2 | 6/2010 | Kremliovsky et al. |
| 7,733,224 B2 | 6/2010 | Tran |
| D621,048 S | 8/2010 | Severe et al. |
| 7,815,494 B2 | 10/2010 | Gringer et al. |
| 7,841,039 B1 | 11/2010 | Squire |
| 7,889,070 B2 | 2/2011 | Reeves et al. |
| D634,431 S | 3/2011 | Severe et al. |
| 7,904,133 B2 | 3/2011 | Gehman et al. |
| 7,907,956 B2 | 3/2011 | Uhlik |
| 7,907,996 B2 | 3/2011 | Prystowsky et al. |
| 7,941,207 B2 | 5/2011 | Korzinov |
| 7,970,450 B2 | 6/2011 | Kroecker et al. |
| 7,979,111 B2 | 7/2011 | Acquista |
| 7,996,075 B2 | 8/2011 | Korzinov et al. |
| 7,996,187 B2 | 8/2011 | Nanikashvili et al. |
| 8,002,701 B2 | 8/2011 | John et al. |
| 8,077,042 B2 | 12/2011 | Peeters |
| 8,103,333 B2 | 1/2012 | Tran |
| 8,108,036 B2 | 1/2012 | Tran |
| 8,116,841 B2 | 2/2012 | Bly et al. |
| 8,150,502 B2 | 4/2012 | Kumar et al. |
| 8,156,945 B2 | 4/2012 | Hart |
| 8,160,682 B2 | 4/2012 | Kumar et al. |
| D659,836 S | 5/2012 | Bensch et al. |
| 8,200,319 B2 | 6/2012 | Pu et al. |
| 8,214,007 B2 | 7/2012 | Baker et al. |
| 8,244,335 B2 | 8/2012 | Kumar et al. |
| 8,249,686 B2 | 8/2012 | Libbus et al. |
| 8,261,754 B2 | 9/2012 | Pitstick |
| 8,265,907 B2 | 9/2012 | Nanikashvili et al. |
| RE43,767 E | 10/2012 | Eggers et al. |
| 8,280,749 B2 | 10/2012 | Hsieh et al. |
| 8,285,356 B2 | 10/2012 | Bly et al. |
| 8,290,129 B2 | 10/2012 | Rogers et al. |
| 8,290,574 B2 | 10/2012 | Field et al. |
| 8,301,219 B2 | 10/2012 | Chen et al. |
| 8,301,236 B2 | 10/2012 | Baumann et al. |
| 8,311,604 B2 | 11/2012 | Rowlandson et al. |
| 8,315,687 B2 | 11/2012 | Cross et al. |
| 8,315,695 B2 | 11/2012 | Sebelius et al. |
| 8,323,188 B2 | 12/2012 | Tran |
| 8,326,394 B2 | 12/2012 | Rowlandson et al. |
| 8,326,407 B2 | 12/2012 | Linker |
| 8,328,718 B2 | 12/2012 | Tran |
| 8,343,116 B2 | 1/2013 | Ignon |
| 8,369,936 B2 | 2/2013 | Farringdon et al. |
| 8,374,688 B2 | 2/2013 | Libbus et al. |
| 8,386,009 B2 | 2/2013 | Lindberg et al. |
| 8,388,543 B2 | 3/2013 | Chon et al. |
| 8,406,843 B2 | 3/2013 | Tiegs et al. |
| 8,412,317 B2 | 4/2013 | Mazar |
| 8,417,326 B2 | 4/2013 | Chon et al. |
| 8,425,414 B2 | 4/2013 | Eveland |
| 8,449,471 B2 | 5/2013 | Tran |
| 8,452,356 B2 | 5/2013 | Vestel et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,478,418 B2 | 7/2013 | Fahey |
| 8,483,809 B2 | 7/2013 | Kim et al. |
| 8,500,636 B2 | 8/2013 | Tran |
| 8,515,529 B2 | 8/2013 | Pu et al. |
| 8,525,673 B2 | 9/2013 | Tran |
| 8,535,223 B2 | 9/2013 | Corroy et al. |
| 8,538,503 B2 | 9/2013 | Kumar et al. |
| 8,540,731 B2 | 9/2013 | Kay |
| 8,560,046 B2 | 10/2013 | Kumar et al. |
| 8,562,527 B2 | 10/2013 | Braun et al. |
| 8,571,645 B2 | 10/2013 | Wu et al. |
| 8,588,908 B2 | 11/2013 | Moorman et al. |

(56) References Cited

U.S. PATENT DOCUMENTS

| | | |
|---|---|---|
| 8,591,430 B2 | 11/2013 | Amurthur et al. |
| 8,594,763 B1 | 11/2013 | Bibian |
| 8,626,262 B2 | 1/2014 | McGusty et al. |
| 8,639,319 B2 | 1/2014 | Hugh et al. |
| 8,668,643 B2 | 3/2014 | Kinast |
| 8,684,900 B2 | 4/2014 | Tran |
| 8,684,925 B2 | 4/2014 | Amurthur et al. |
| 8,688,189 B2 | 4/2014 | Shennib |
| 8,688,190 B2 | 4/2014 | Libbus et al. |
| 8,688,202 B2 | 4/2014 | Brockway et al. |
| 8,718,742 B2 | 5/2014 | Beck et al. |
| 8,718,752 B2 | 5/2014 | Libbus et al. |
| 8,718,753 B2 | 5/2014 | Chon et al. |
| 8,731,632 B1 | 5/2014 | Sereboff et al. |
| 8,738,118 B2 | 5/2014 | Moon et al. |
| 8,755,876 B2 | 6/2014 | Chon et al. |
| 8,782,308 B2 | 7/2014 | Vlach |
| 8,789,727 B2 | 7/2014 | Mortazavi |
| 8,790,257 B2 | 7/2014 | Libbus et al. |
| 8,795,174 B2 | 8/2014 | Manicka et al. |
| 8,818,481 B2 | 8/2014 | Bly et al. |
| 8,823,490 B2 | 9/2014 | Libbus et al. |
| 8,838,218 B2 | 9/2014 | Khair |
| 8,858,450 B2 | 10/2014 | Chon et al. |
| 8,874,185 B2 | 10/2014 | Sonnenborg |
| 8,903,477 B2 | 12/2014 | Berkner |
| 8,903,484 B2 | 12/2014 | Mazar |
| 8,909,328 B2 | 12/2014 | Chon |
| 8,909,330 B2 | 12/2014 | McCombie et al. |
| 8,909,332 B2 | 12/2014 | Vitali et al. |
| 8,909,333 B2 | 12/2014 | Rossi |
| 8,909,832 B2 | 12/2014 | Vlach et al. |
| 8,926,509 B2 | 1/2015 | Magar et al. |
| 8,945,019 B2 | 2/2015 | Prystowsky et al. |
| 8,948,854 B2 | 2/2015 | Friedman et al. |
| 8,954,129 B1 | 2/2015 | Schlegel et al. |
| 8,956,293 B2 | 2/2015 | McCombie et al. |
| 8,968,195 B2 | 3/2015 | Tran |
| 8,972,000 B2 | 3/2015 | Manera |
| 8,979,755 B2 | 3/2015 | Szydlo-Moore et al. |
| 9,014,777 B2 | 4/2015 | Woo |
| 9,015,008 B2 | 4/2015 | Geva et al. |
| 9,017,255 B2 | 4/2015 | Raptis et al. |
| 9,017,256 B2 | 4/2015 | Gottesman |
| 9,021,161 B2 | 4/2015 | Vlach et al. |
| 9,021,165 B2 | 4/2015 | Vlach |
| 9,026,190 B2 | 5/2015 | Shenasa et al. |
| 9,037,223 B2 | 5/2015 | Oral et al. |
| 9,044,148 B2 | 6/2015 | Michelson et al. |
| 9,084,548 B2 | 7/2015 | Bouguerra |
| 9,095,274 B2 | 8/2015 | Fein et al. |
| 9,101,264 B2 | 8/2015 | Acquista |
| 9,138,144 B2 | 9/2015 | Geva |
| 9,149,228 B2 | 10/2015 | Kinast |
| 9,173,670 B2 | 11/2015 | Sepulveda et al. |
| 9,179,851 B2 | 11/2015 | Baumann et al. |
| 9,211,076 B2 | 12/2015 | Kim |
| 9,226,679 B2 | 1/2016 | Balda |
| 9,241,649 B2 | 1/2016 | Kumar et al. |
| 9,241,650 B2 | 1/2016 | Amirim |
| 9,277,864 B2 | 3/2016 | Yang et al. |
| 9,282,894 B2 | 3/2016 | Banet et al. |
| 9,307,921 B2 | 4/2016 | Friedman et al. |
| 9,345,414 B1 | 5/2016 | Bardy et al. |
| 9,355,215 B2 | 5/2016 | Vlach |
| 9,357,939 B1 | 6/2016 | Nosrati |
| 9,364,150 B2 | 6/2016 | Sebelius et al. |
| 9,398,853 B2 | 7/2016 | Nanikashvili |
| 9,408,576 B2 | 8/2016 | Chon et al. |
| 9,414,753 B2 | 8/2016 | Chon et al. |
| 9,414,786 B1 | 8/2016 | Brockway et al. |
| 9,433,367 B2 | 9/2016 | Felix et al. |
| 9,439,566 B2 | 9/2016 | Arne et al. |
| 9,439,599 B2 | 9/2016 | Thompson et al. |
| 9,445,719 B2 | 9/2016 | Libbus et al. |
| 9,451,890 B2 | 9/2016 | Gitlin et al. |
| 9,451,975 B2 | 9/2016 | Sepulveda et al. |
| 9,474,445 B2 | 10/2016 | Eveland |
| 9,474,461 B2 | 10/2016 | Fisher et al. |
| 9,478,998 B1 | 10/2016 | Lapetina et al. |
| D773,056 S | 11/2016 | Vlach |
| 9,492,084 B2 | 11/2016 | Behar et al. |
| 9,504,423 B1 | 11/2016 | Bardy et al. |
| 9,510,764 B2 | 12/2016 | Li et al. |
| 9,510,768 B2 | 12/2016 | Rossi |
| 9,526,433 B2 | 12/2016 | Lapetina et al. |
| 9,579,020 B2 | 2/2017 | Libbus et al. |
| 9,597,004 B2 | 3/2017 | Hughes et al. |
| 9,615,793 B2 | 4/2017 | Solosko et al. |
| 9,655,518 B2 | 5/2017 | Lin |
| 9,662,030 B2 | 5/2017 | Thng et al. |
| 9,675,264 B2 | 6/2017 | Acquista et al. |
| 9,706,938 B2 | 7/2017 | Chakravarthy et al. |
| 9,706,956 B2 | 7/2017 | Brockway et al. |
| 9,713,428 B2 | 7/2017 | Chon et al. |
| 9,730,604 B2 | 8/2017 | Li et al. |
| 9,775,534 B2 | 10/2017 | Korzinov et al. |
| 9,782,095 B2 | 10/2017 | Ylostalo et al. |
| 9,839,363 B2 | 12/2017 | Albert |
| 9,888,866 B2 | 2/2018 | Chon et al. |
| 9,907,478 B2 | 3/2018 | Friedman et al. |
| 9,986,921 B2 | 6/2018 | Chon et al. |
| 10,095,841 B2 | 10/2018 | Dettinger et al. |
| 10,299,691 B2* | 5/2019 | Hughes ............... A61B 5/6832 |
| 2001/0056262 A1 | 12/2001 | Cabiri et al. |
| 2002/0067256 A1 | 6/2002 | Kail |
| 2002/0082491 A1 | 6/2002 | Nissila |
| 2002/0087167 A1 | 7/2002 | Winitsky |
| 2002/0180605 A1 | 12/2002 | Ozguz et al. |
| 2003/0069510 A1 | 4/2003 | Semler |
| 2003/0083559 A1 | 5/2003 | Thompson |
| 2003/0149349 A1 | 8/2003 | Jensen |
| 2003/0176795 A1 | 9/2003 | Harris et al. |
| 2003/0195408 A1 | 10/2003 | Hastings |
| 2003/0199811 A1 | 10/2003 | Sage, Jr. et al. |
| 2003/0212319 A1 | 11/2003 | Magill |
| 2004/0032957 A1 | 2/2004 | Mansy et al. |
| 2004/0068195 A1 | 4/2004 | Massicotte et al. |
| 2004/0077954 A1 | 4/2004 | Oakley et al. |
| 2004/0082843 A1 | 4/2004 | Menon |
| 2004/0215091 A1 | 10/2004 | Lohman et al. |
| 2004/0236202 A1 | 11/2004 | Burton |
| 2004/0254587 A1 | 12/2004 | Park |
| 2004/0260189 A1 | 12/2004 | Eggers et al. |
| 2005/0096513 A1 | 5/2005 | Ozguz et al. |
| 2005/0101875 A1 | 5/2005 | Semler et al. |
| 2005/0118246 A1 | 6/2005 | Wong et al. |
| 2005/0119580 A1 | 6/2005 | Eveland |
| 2005/0165323 A1 | 7/2005 | Montgomery et al. |
| 2005/0204636 A1 | 9/2005 | Azar et al. |
| 2005/0277841 A1 | 12/2005 | Shennib |
| 2005/0280531 A1 | 12/2005 | Fadem et al. |
| 2006/0030781 A1 | 2/2006 | Shennib |
| 2006/0030782 A1 | 2/2006 | Shennib |
| 2006/0047215 A1 | 3/2006 | Newman et al. |
| 2006/0084883 A1 | 4/2006 | Linker |
| 2006/0142648 A1 | 6/2006 | Banet et al. |
| 2006/0142654 A1 | 6/2006 | Rytky |
| 2006/0149156 A1 | 7/2006 | Cochran et al. |
| 2006/0155173 A1 | 7/2006 | Anttila et al. |
| 2006/0155183 A1 | 7/2006 | Kroecker et al. |
| 2006/0155199 A1 | 7/2006 | Logier et al. |
| 2006/0155200 A1 | 7/2006 | Ng et al. |
| 2006/0161064 A1 | 7/2006 | Watrous et al. |
| 2006/0161065 A1 | 7/2006 | Elion |
| 2006/0161066 A1 | 7/2006 | Elion |
| 2006/0161067 A1 | 7/2006 | Elion |
| 2006/0161068 A1 | 7/2006 | Hastings et al. |
| 2006/0224072 A1 | 10/2006 | Shennib |
| 2006/0264767 A1 | 11/2006 | Shennib |
| 2007/0003695 A1 | 1/2007 | Tregub et al. |
| 2007/0010729 A1 | 1/2007 | Virtanen |
| 2007/0027388 A1 | 2/2007 | Chou |
| 2007/0088419 A1 | 4/2007 | Florina et al. |

(56) References Cited

U.S. PATENT DOCUMENTS

| | | |
|---|---|---|
| 2007/0156054 A1 | 7/2007 | Korzinov et al. |
| 2007/0225611 A1 | 9/2007 | Kumar et al. |
| 2007/0249946 A1 | 10/2007 | Kumar et al. |
| 2007/0255153 A1 | 11/2007 | Kumar et al. |
| 2007/0270678 A1 | 11/2007 | Fadem et al. |
| 2007/0285868 A1 | 12/2007 | Lindberg et al. |
| 2007/0293776 A1 | 12/2007 | Korzinov et al. |
| 2008/0039730 A1 | 2/2008 | Pu et al. |
| 2008/0091089 A1 | 4/2008 | Guillory et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0275327 A1 | 11/2008 | Faarbaek et al. |
| 2008/0288026 A1 | 11/2008 | Cross et al. |
| 2009/0062670 A1 | 3/2009 | Sterling et al. |
| 2009/0062671 A1 | 3/2009 | Brockway |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0182204 A1 | 7/2009 | Semler et al. |
| 2009/0253975 A1 | 10/2009 | Tiegs |
| 2009/0292194 A1 | 11/2009 | Libbus et al. |
| 2010/0022864 A1 | 1/2010 | Cordero |
| 2010/0042113 A1 | 2/2010 | Mah |
| 2010/0049006 A1 | 2/2010 | Magar et al. |
| 2010/0051039 A1 | 3/2010 | Ferrara |
| 2010/0056881 A1 | 3/2010 | Libbus et al. |
| 2010/0057056 A1 | 3/2010 | Gurtner |
| 2010/0081913 A1 | 4/2010 | Cross et al. |
| 2010/0145359 A1 | 6/2010 | Keller |
| 2010/0191310 A1 | 7/2010 | Bly |
| 2010/0234716 A1 | 9/2010 | Engel |
| 2010/0249625 A1 | 9/2010 | Lin |
| 2010/0268103 A1 | 10/2010 | McNamara et al. |
| 2010/0312131 A1 | 12/2010 | Naware et al. |
| 2010/0331711 A1 | 12/2010 | Krauss et al. |
| 2011/0021937 A1 | 1/2011 | Hugh et al. |
| 2011/0087083 A1 | 4/2011 | Poeze et al. |
| 2011/0144470 A1 | 6/2011 | Mazar et al. |
| 2011/0160601 A1 | 6/2011 | Wang et al. |
| 2011/0166468 A1 | 7/2011 | Prystowsky et al. |
| 2011/0190650 A1 | 8/2011 | McNair |
| 2011/0218415 A1 | 9/2011 | Chen et al. |
| 2011/0237922 A1 | 9/2011 | Parker, III et al. |
| 2011/0306862 A1 | 12/2011 | Hayes-Gill |
| 2012/0029307 A1 | 2/2012 | Paquet et al. |
| 2012/0071730 A1 | 3/2012 | Romero |
| 2012/0071731 A1 | 3/2012 | Gottesman |
| 2012/0071743 A1 | 3/2012 | Todorov et al. |
| 2012/0083670 A1 | 4/2012 | Rotondo et al. |
| 2012/0088999 A1 | 4/2012 | Bishay et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0110226 A1 | 5/2012 | Vlach et al. |
| 2012/0110228 A1 | 5/2012 | Vlach et al. |
| 2012/0172676 A1 | 7/2012 | Penders et al. |
| 2012/0197150 A1 | 8/2012 | Cao et al. |
| 2012/0209102 A1 | 8/2012 | Ylotalo et al. |
| 2012/0215123 A1 | 8/2012 | Kumar et al. |
| 2012/0220835 A1 | 8/2012 | Chung |
| 2012/0259233 A1 | 10/2012 | Chan et al. |
| 2012/0271141 A1 | 10/2012 | Davies |
| 2012/0310070 A1 | 12/2012 | Kumar et al. |
| 2012/0323257 A1 | 12/2012 | Sutton |
| 2013/0046151 A1 | 2/2013 | Bsoul et al. |
| 2013/0085347 A1 | 4/2013 | Manicka et al. |
| 2013/0096395 A1 | 4/2013 | Katra et al. |
| 2013/0116533 A1 | 5/2013 | Lian et al. |
| 2013/0116585 A1 | 5/2013 | Bouguerra |
| 2013/0144146 A1 | 6/2013 | Linker |
| 2013/0150698 A1 | 6/2013 | Hsu et al. |
| 2013/0191035 A1 | 7/2013 | Chon et al. |
| 2013/0225938 A1 | 8/2013 | Vlach |
| 2013/0225967 A1 | 8/2013 | Esposito |
| 2013/0226018 A1 | 8/2013 | Kumar et al. |
| 2013/0245415 A1 | 9/2013 | Kumar et al. |
| 2013/0245472 A1 | 9/2013 | Eveland |
| 2013/0253285 A1 | 9/2013 | Bly et al. |
| 2013/0274584 A1 | 10/2013 | Finlay et al. |
| 2013/0296680 A1 | 11/2013 | Linker |
| 2013/0300575 A1 | 11/2013 | Kurzweil et al. |
| 2013/0324868 A1 | 12/2013 | Kaib et al. |
| 2013/0331663 A1 | 12/2013 | Albert et al. |
| 2013/0331665 A1 | 12/2013 | Bly et al. |
| 2013/0338448 A1 | 12/2013 | Libbus et al. |
| 2014/0012154 A1 | 1/2014 | Mazar |
| 2014/0058280 A1 | 2/2014 | Chefles et al. |
| 2014/0094709 A1 | 4/2014 | Korzinov et al. |
| 2014/0100432 A1 | 4/2014 | Golda et al. |
| 2014/0171751 A1 | 6/2014 | Sankman et al. |
| 2014/0116825 A1 | 7/2014 | Kurzweil et al. |
| 2014/0206976 A1 | 7/2014 | Thompson et al. |
| 2014/0206977 A1 | 7/2014 | Bahney et al. |
| 2014/0275827 A1 | 9/2014 | Gill et al. |
| 2014/0275928 A1 | 9/2014 | Acquista et al. |
| 2014/0330136 A1 | 11/2014 | Manicka et al. |
| 2015/0022372 A1 | 1/2015 | Vosch |
| 2015/0057512 A1 | 2/2015 | Kapoor |
| 2015/0073252 A1 | 3/2015 | Mazar |
| 2015/0081959 A1 | 3/2015 | Vlach et al. |
| 2015/0082623 A1 | 3/2015 | Felix et al. |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087933 A1 | 3/2015 | Gibson et al. |
| 2015/0087948 A1 | 3/2015 | Bishay et al. |
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0088007 A1 | 3/2015 | Bardy et al. |
| 2015/0088020 A1 | 3/2015 | Dreisbach et al. |
| 2015/0094556 A1 | 4/2015 | Geva et al. |
| 2015/0173671 A1 | 6/2015 | Paalasmaa et al. |
| 2015/0223711 A1 | 8/2015 | Raeder et al. |
| 2015/0238107 A1 | 8/2015 | Acquista et al. |
| 2015/0289814 A1 | 10/2015 | Magar et al. |
| 2015/0297134 A1 | 10/2015 | Albert et al. |
| 2015/0327781 A1 | 11/2015 | Hernandez-Silveira et al. |
| 2015/0351799 A1 | 12/2015 | Sepulveda et al. |
| 2015/0374244 A1 | 12/2015 | Yoo et al. |
| 2016/0022161 A1 | 1/2016 | Khair |
| 2016/0029906 A1 | 2/2016 | Tompkins et al. |
| 2016/0066808 A1 | 3/2016 | Hijazi |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0113520 A1 | 4/2016 | Manera |
| 2016/0120433 A1 | 5/2016 | Hughes et al. |
| 2016/0120434 A1 | 5/2016 | Park et al. |
| 2016/0128597 A1 | 5/2016 | Lin et al. |
| 2016/0135746 A1 | 5/2016 | Kumar et al. |
| 2016/0157744 A1 | 6/2016 | Wu et al. |
| 2016/0166155 A1 | 6/2016 | Banet et al. |
| 2016/0192852 A1 | 7/2016 | Bozza et al. |
| 2016/0192855 A1 | 7/2016 | Geva et al. |
| 2016/0192856 A1 | 7/2016 | Lee |
| 2016/0198972 A1 | 7/2016 | Lee et al. |
| 2016/0232807 A1 | 8/2016 | Ghaffari et al. |
| 2016/0262619 A1 | 9/2016 | Marcus et al. |

(56) References Cited

U.S. PATENT DOCUMENTS

| | | |
|---|---|---|
| 2016/0287177 A1 | 10/2016 | Huppert et al. |
| 2016/0287207 A1 | 10/2016 | Xue |
| 2016/0296132 A1 | 10/2016 | Bojovic et al. |
| 2016/0302726 A1 | 10/2016 | Chang |
| 2016/0317048 A1 | 11/2016 | Chan et al. |
| 2016/0317057 A1 | 11/2016 | Li et al. |
| 2016/0367164 A1 | 12/2016 | Felix et al. |
| 2016/0374583 A1 | 12/2016 | Cerruti et al. |
| 2017/0042447 A1 | 2/2017 | Rossi |
| 2017/0065823 A1 | 3/2017 | Kaib et al. |
| 2017/0188872 A1 | 7/2017 | Hughes et al. |
| 2018/0146875 A1 | 5/2018 | Friedman et al. |
| 2018/0374576 A1 | 12/2018 | Dettinger et al. |

FOREIGN PATENT DOCUMENTS

| | | |
|---|---|---|
| CA | 2752154 | 8/2010 |
| CA | 2797980 | 11/2011 |
| CA | 2898626 | 7/2014 |
| CA | 2651203 | 9/2017 |
| EP | 01782729 | 5/2007 |
| EP | 1981402 | 10/2008 |
| EP | 2262419 | 12/2010 |
| EP | 2395911 | 12/2011 |
| EP | 2568878 | 3/2013 |
| EP | 2635179 | 9/2013 |
| EP | 2635180 | 9/2013 |
| EP | 2948050 | 12/2015 |
| EP | 2983593 | 2/2016 |
| EP | 3165161 | 5/2017 |
| EP | 3212061 | 9/2017 |
| GB | 2299038 | 9/1996 |
| GB | 2348707 | 10/2000 |
| JP | 08-317913 | 3/1996 |
| JP | 2000-126145 | 5/2000 |
| JP | 2001-057967 | 3/2001 |
| JP | 2004-121360 | 4/2004 |
| JP | 2007-045967 | 2/2007 |
| JP | 2007-503910 A | 3/2007 |
| JP | 2007-504917 A | 3/2007 |
| JP | 2007-097822 | 4/2007 |
| JP | 2007-296266 | 11/2007 |
| JP | 2009-518099 A | 5/2009 |
| JP | 2009-525816 | 7/2009 |
| JP | 2011-519583 | 7/2011 |
| JP | 2013-521966 | 6/2013 |
| JP | 5203973 | 6/2013 |
| JP | 5559425 | 7/2014 |
| JP | 2014-236982 | 12/2014 |
| JP | 2016-504159 | 2/2016 |
| JP | 2013-517053 | 5/2016 |
| JP | 2017-136380 | 8/2017 |
| JP | 6198849 | 9/2017 |
| KR | 10-1513288 | 4/2015 |
| WO | WO 1999/023943 | 5/1999 |
| WO | WO 2001/016607 | 3/2001 |
| WO | WO 2004/100785 | 11/2004 |
| WO | WO 2005/025668 | 3/2005 |
| WO | WO 2005/037946 | 4/2005 |
| WO | WO 2005/084533 | 9/2005 |
| WO | WO 2006/094513 | 9/2006 |
| WO | WO 2007/049080 | 3/2007 |
| WO | WO 2007/036748 | 4/2007 |
| WO | WO 2007/063436 | 6/2007 |
| WO | WO 2007/071180 | 6/2007 |
| WO | WO 2007/072069 | 6/2007 |
| WO | WO 2007/092543 | 8/2007 |
| WO | WO 2008/005015 | 1/2008 |
| WO | WO 2008/005016 | 1/2008 |
| WO | WO 2008/057884 | 5/2008 |
| WO | WO 2008/120154 | 10/2008 |
| WO | WO 2009/074928 | 6/2009 |
| WO | WO 2009/112976 | 9/2009 |
| WO | WO 2009/112979 | 9/2009 |
| WO | WO 2009/134826 | 11/2009 |
| WO | WO 2010/104952 | 9/2010 |
| WO | WO 2010/105203 | 9/2010 |
| WO | WO 2010/093900 | 10/2010 |
| WO | WO 2011/077097 | 6/2011 |
| WO | WO 2011/143490 | 11/2011 |
| WO | WO 2011/149755 | 12/2011 |
| WO | WO 2012/009453 | 1/2012 |
| WO | WO 2012/061509 | 5/2012 |
| WO | WO 2012/061518 | 5/2012 |
| WO | WO 2012/125425 | 9/2012 |
| WO | WO 2012/160550 | 11/2012 |
| WO | WO 2014047032 A1 | 3/2014 |
| WO | WO 2014/051563 | 4/2014 |
| WO | WO 2014/055994 A1 | 4/2014 |
| WO | WO 2014/116825 | 7/2014 |
| WO | WO 2014/168841 | 10/2014 |
| WO | WO 2016044514 A1 | 3/2016 |
| WO | WO 2016044515 A1 | 3/2016 |
| WO | WO 2016044519 A1 | 3/2016 |
| WO | WO 2016057728 A1 | 4/2016 |
| WO | WO 2016/070128 | 5/2016 |
| WO | WO 2016/181321 | 11/2016 |
| WO | WO 2017/039518 | 3/2017 |
| WO | WO 2017/041014 | 3/2017 |

OTHER PUBLICATIONS

U.S. Appl. No. 15/005,854, filed Jan. 25, 2016, Kumar et al.

3M Corporation, "3M Surgical Tapes—Choose the Correct Tape" quicksheet (2004).

Del Mar et al.; The history of clinical holter monitoring; A.N.E.; vol. 10; No. 2; pp. 226-230; Apr. 2005.

Enseleit et al.; Long-term continuous external electrocardiographic recording: a review; Europsace; vol. 8; pp. 255-266; 2006.

Hoefman et al.; Optimal duration of event recording for diagnosis of arrhythmias in patients with palpitations and light-headedness in the general practice; Family Practice; Dec. 7, 2006.

International Search Report and Written Opinion for International Application No. PCT/US2015/058478 dated Feb. 16, 2016 in 12 pages.

Kennedy et al.; The history, science, and innovation of holter technology; A.N.E.; vol. 11; No. 1; pp. 85-94; 2006.

Mundt et al. "A Multiparameter Wearable Physiologic Monitoring System for Space and Terrestrial Applications" IEEE Transactions on Information Technology in Biomedicine, vol. 9, No. 3, pp. 382-384, Sep. 2005.

Reiffel et al.; Comparison of autotriggered memory loop recorders versus standard loop recorders versus 24-hour holter monitors for arrhythmia detection; Am. J. Cardiology; vol. 95; pp. 1055-1059; May 1, 2005.

Request for Reexamination of U.S. Pat. No. 7,020,508 under 35 U.S.C. §§ 311-318 and 37 C.F.R. § 1.913 as submitted Sep. 14, 2012 in 78 pages.

Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Sep. 24, 2012.

Ward et al.; Assessment of the diagnostic value of 24-hour ambulatory electrocardiographic monitoring; Biotelemetry Patient monitoring; vol. 7; 1980.

Ziegler et al.; Comparison of continuous versus intermittent monitoring of atrial arrhythmias; Heart Rhythm; vol. 3; No. 12; pp. 1445-1452; Dec. 2006.

Zimetbaum et al.; The evolving role of ambulatory arrhythmia monitoring in general clinic practice; Ann. Intern. Med.; vol. 130; pp. 846-8556; 1999.

Zimetbaum et al.; Utility of patient-activated cardiac event recorders in general clinical practice; The Amer. J. of Cardiology; vol. 79; Feb. 1, 1997.

Mayo Clinic, "Mayo Alumni", Spring 2011, in 24 pages, Rochester, MN.

* cited by examiner

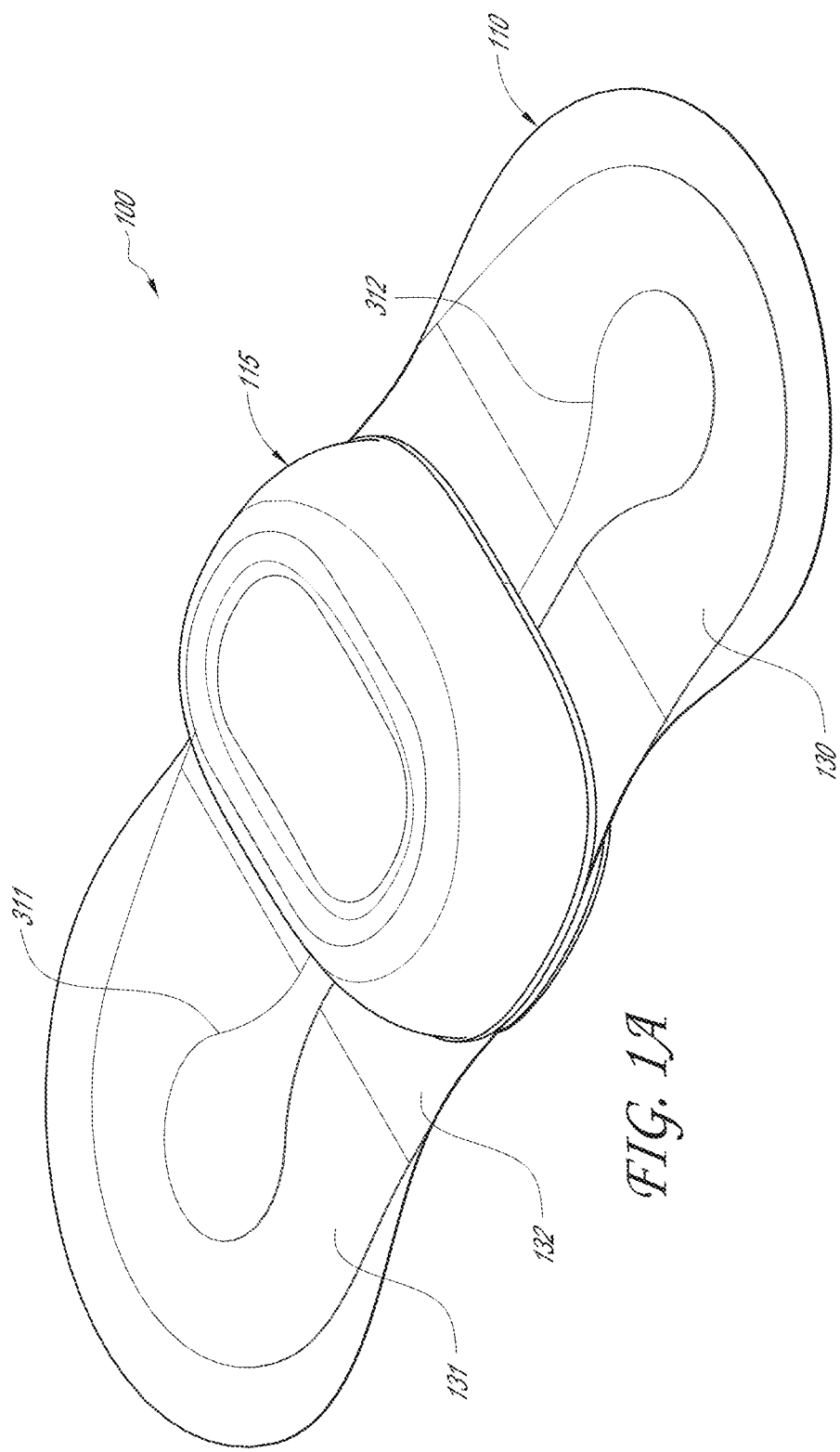

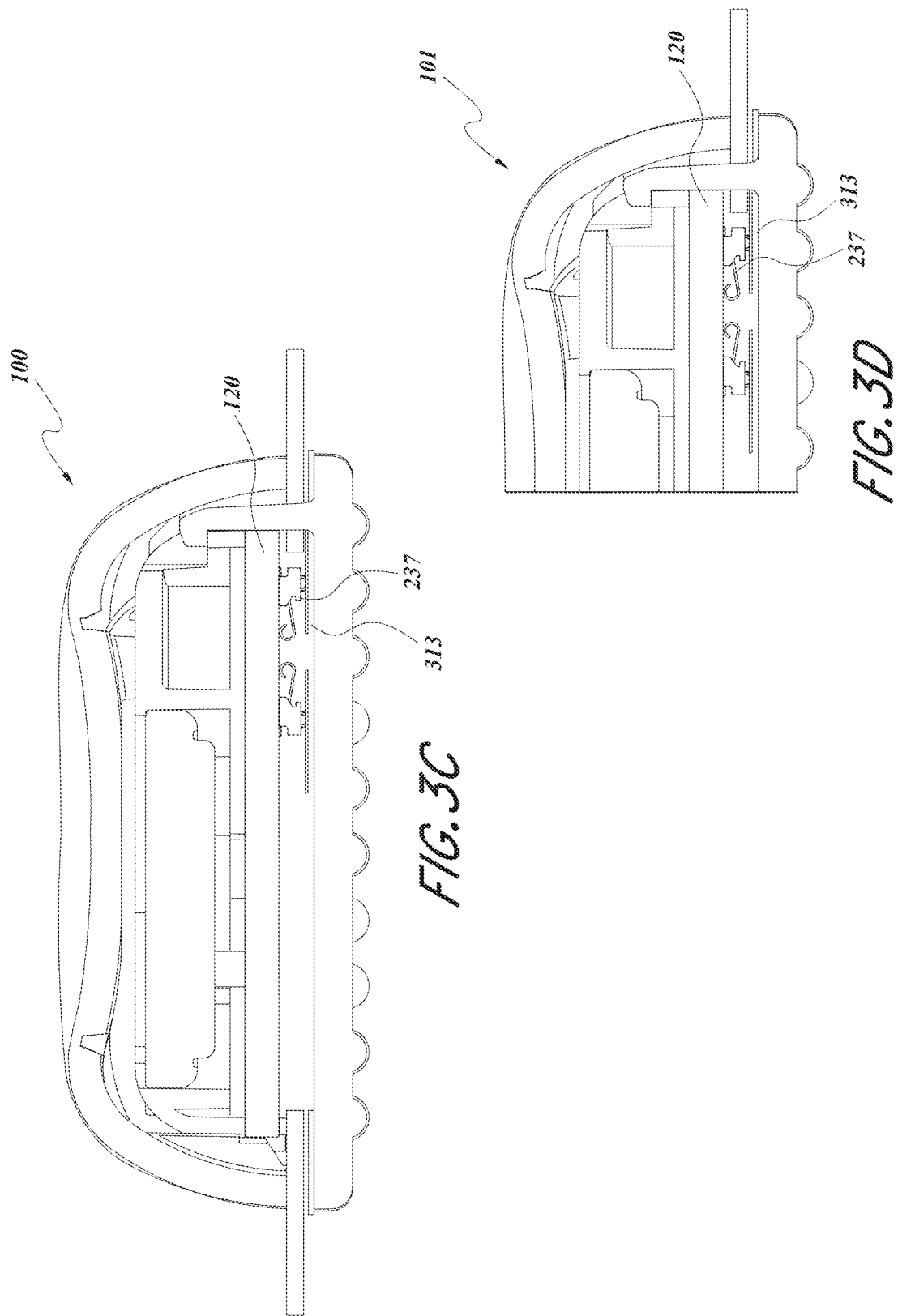

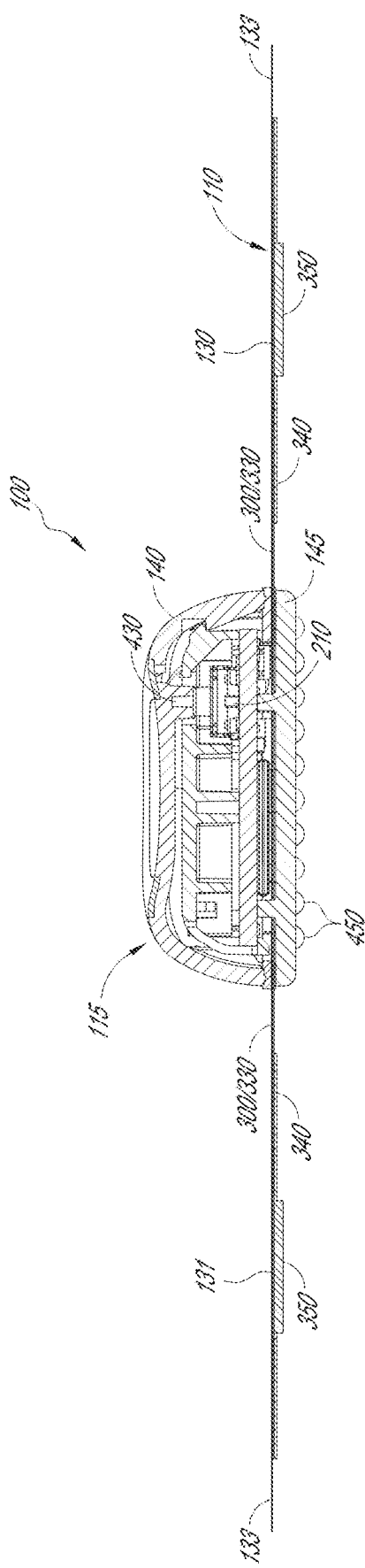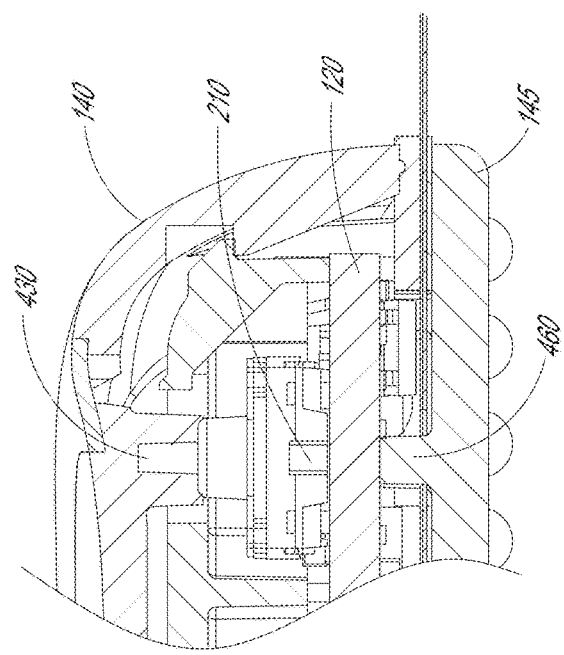
FIG. 6A
FIG. 6B

WEARABLE MONITOR

CROSS-REFERENCE TO RELATED APPLICATIONS

This application is a continuation of U.S. application Ser. No. 16/160,173, filed Oct. 15, 2018, entitled WEARABLE MONITOR WITH ARRHYTHMIA BURDEN EVALUATION, which is a continuation of U.S. application Ser. No. 15/966,258, filed Apr. 30, 2018, entitled WEARABLE MONITOR WITH ARRHYTHMIA BURDEN EVALUATION, which is a continuation of U.S. application Ser. No. 15/463,944, filed Mar. 20, 2017, entitled WEARABLE MONITOR, which is a continuation of U.S. application Ser. No. 14/929,121 filed Oct. 30, 2015, entitled WEARABLE MONITOR, which claims the benefit of U.S. Provisional Application No. 62/073,910, filed Oct. 31, 2014, entitled WIRELESS PHYSIOLOGICAL MONITORING. The content of the aforementioned applications is hereby incorporated by reference in their entireties as if fully set forth herein. The benefit of priority to the foregoing applications is claimed under the appropriate legal basis, including, without limitation, under 35 U.S.C. § 119(e).

BACKGROUND

For purposes of this disclosure, certain aspects, advantages, and novel features of various embodiments are described herein. It is to be understood that not necessarily all such advantages may be achieved in accordance with any particular embodiment. Thus, various embodiments may be or carried out in a manner that achieves one advantage or group of advantages as taught herein without necessarily achieving other advantages as may be taught or suggested herein.

FIELD OF THE INVENTION

System for inferring cardiac rhythm information from heart beat time series information collected by wearable sensors, and system for selective transmission of electrocardiographic signal data from a wearable sensor

DESCRIPTION OF THE RELATED ART

Abnormal heart rhythms, or arrhythmias, may cause various types of symptoms, such as loss of—consciousness, palpitations, dizziness, or even death. An arrhythmia that causes such symptoms is often an indicator of significant underlying heart disease. It is important to identify when such symptoms are due to an abnormal heart rhythm, since treatment with various procedures, such as pacemaker implantation or percutaneous catheter ablation, can successfully ameliorate these problems and prevent significant symptoms and death. For example, monitors such as Holter monitors and similar devices are currently in use to monitor heart rhythms.

BRIEF SUMMARY OF EMBODIMENTS

Embodiments described herein are directed to a physiological monitoring device that may be worn continuously and comfortably by a human or animal subject for at least one week or more and more typically two to three weeks or more. In one embodiment, the device is specifically designed to sense and record cardiac rhythm (for example, electrocardiogram, ECG) data, although in various alternative embodiments one or more additional physiological parameters may be sensed and recorded. Such physiological monitoring devices may include a number of features to facilitate and/or enhance the patient experience and to make diagnosis of cardiac arrhythmias more accurate and timely.

In some embodiments, an electronic device for monitoring physiological signals in a mammal comprises: at least two flexible wings extending laterally from a rigid housing, wherein the flexible wings comprise a first set of materials which enable the wings to conform to a surface of the mammal and the rigid housing comprises a second set of materials; a printed circuit board assembly housed within the rigid housing, wherein the rigid housing is configured to prevent deformation of the printed circuit board in response to movement of the mammal; at least two electrodes embedded within the flexible wings, the electrodes configured to provide conformal contact with the surface of the mammal and to detect the physiological signals of the mammal; at least two electrode traces embedded within the wings and mechanically decoupled from the rigid housing, the electrode traces configured to provide conformal contact with the surface of the mammal and transmit electrical signals from the electrodes to the printed circuit board assembly; and, at least one hinge portion connecting the wings to the rigid housing, the hinge portions configured to flex freely at the area where it is joined to the rigid housing.

In certain embodiments, each wing may comprise an adhesive. In embodiments, the electrodes can be in the same plane as the adhesive. In certain embodiments, each wing comprises at least one rim, wherein the rim is thinner than an adjacent portion of each wing. The rigid housing may further comprise dimples configured to allow for airflow between the rigid housing and the surface of the mammal. In certain embodiments, the rim is configured to prevent the release of a portion of the wing from the surface of the mammal. In some embodiments, an electronic device for monitoring physiological systems may comprise a measuring instrument configured to detect motion signals in at least one axis. This measuring instrument may be an accelerometer that can be configured to detect motion signals in three axes.

In embodiments, the motion signals can be collected in time with the physiological signals. In certain embodiments, a motion artifact is identified when the physiological signals and the motion signals match. Further embodiments may call for an event trigger coupled to the printed circuit board assembly. In some embodiments, the event trigger input is supported by the rigid housing so as to prevent mechanical stress on the printed circuit board when the trigger is activated which, in turn, can reduce a source of artifact in the recorded signal. The event trigger may be concave and larger than a human finger such that the event trigger is easily located. In certain embodiments, the electrode traces are configured to minimize signal distortion during movement of the mammal. In particular embodiments, gaskets may be used as a means for sealable attachment to the rigid housing.

In certain embodiments, a method for monitoring physiological signals in a mammal may comprise: attaching an electronic device to the mammal, wherein the device comprises: at least two electrodes configured to detect physiological signals from the mammal, at least one measuring instrument configured to detect secondary signals, and at least two electrode traces connected to the electrodes and a rigid housing; and, comparing the physiological signals to the secondary signals to identify an artifact.

In certain embodiments, identification of artifacts comprises a comparison between the frequency spectrum of the physiological signals and the frequency spectrum of the secondary signals. In embodiments, the secondary signals comprise motion signals that may be used to derive the activity and position of the mammal. In certain embodiments, the secondary signals are collected in three axes. In some embodiments, a tertiary signal may also be collected. In certain embodiments, the secondary signals comprise information about the connection between the electronic device and the mammal. In some embodiments, the secondary signals may be used to detect when the mammal is sleeping.

In some embodiments, a method of removing and replacing portions of a modular physiological monitoring device may comprise: applying the device described above to a mammal for a period of time greater than 7 days and collecting physiological data; using the device to detect a first set of physiological signals; removing the device from the surface of the mammal; removing a first component from the device; and, incorporating the first component into a second physiological monitoring device, the second physiological monitoring device configured to detect a second set of physiological signals.

In some embodiments, the first component is electrically connected to other device components without the use of a permanent connection. In some embodiments, the device may further comprise spring connections. In certain embodiments, the first component may be preserved for a second use by a rigid housing to prevent damage. In particular embodiments, the first component is secured within a device by a mechanism that is capable of re-securing a second component once the first component is removed.

Certain embodiments may concern a system for inferring cardiac rhythm information from time-series data of heart beat intervals, as obtained from either consumer wearable or medical device products. A further aspect concerns improvements to the system to enable cardiac rhythm information to be inferred in a more robust and/or timely manner through the use of additional sources of data. This additional data may include summary statistics or specific signal features derived from an ECG, user activity time series data derived from an accelerometer, information related to user state, or information related to the day/time of the recording.

In certain embodiments, a system for selective transmission of electrocardiographic signal data from a wearable medical sensor, where QRS refers to the three fiducial points of an ECG recording at the time of ventricle depolarization, may comprise:

a. A wearable medical sensor incorporating a QRS detector that produces a real-time estimate of each R peak location in the ECG b. Transmission of an R-R interval time series together with an onset time stamp from the sensor to a smartphone or internet-connected gateway device, according to a predefined schedule c. Transmission of the R-R interval time series and the onset time stamp from the smartphone or internet-connected gateway device to a server d. Server-side algorithmic inference of the most probable rhythms and their onset/offset times from the R-R interval time series data e. Filtering the list of inferred heart rhythms according to specific filter criteria, such that only inferred rhythms matching the given criteria are retained after filtering f. Transmission of the onset/offset time for each rhythm remaining after filtering, from the server to the smartphone or internet-connected gateway device g. Transmission of the onset/offset time for each rhythm remaining after filtering, from the smartphone or internet-connected gateway device to the wearable sensor h. Transmission of the section of recorded ECG corresponding to each onset-offset time pair from the sensor to the smartphone or internet-connected gateway device i. Transmission of the section of recorded ECG corresponding to each onset-offset time pair from the smartphone or internet-connected gateway device to the server The rhythm filter criteria may be specified by a physician or other medical professional prior to the use of the wearable sensor by a patient. In other embodiments, the rhythm filter criteria are dynamic and can be updated during the use of the system according to predefined rules. In some embodiments, these predefined rules may describe an adjustment to the filter criteria based on previous findings during use of the system. In some embodiments, the onset and offset time for each inferred rhythm may be adjusted such that the resulting duration for each rhythm is less than a given maximum permissible duration. Computed confidence measures may be an input to the rhythm filter criteria. In some embodiments, the system comprises inferring cardiac rhythm information from R-R interval time series data. In certain embodiments, the cardiac rhythm inference system is implemented as a cloud service accessible via an API.

In certain embodiments, the cardiac rhythm inference system is provided through a software library that can be incorporated into a standalone application. The R-R interval values may be are estimated from a photoplethysmography signal.

In certain embodiments of a method for inferring cardiac rhythm information, the cardiac rhythm inference system computes a confidence score for each type of cardiac rhythm, the method comprising:

a. Computing the frequency and duration of each cardiac rhythm type inferred from the collection of R-R interval time series data for the given user b. Estimating a confidence statistic for each rhythm type based on the inferred frequency and duration of the rhythm across the collection of R-R interval time series for the given user c. Evaluating if the confidence statistic for each inferred rhythm exceeds a pre-determined threshold value d. Providing rhythm information back to the calling software only for those inferred rhythms for which the confidence statistic exceeds the threshold value In certain embodiments, the cardiac rhythm inference system accepts additional sources of data, comprising one or more of:

e. User activity time series data measured by an accelerometer f. Information on the specific day and time of each R-R interval time series recording g. Information on user age, gender, clinical indication for monitoring, pre-existing medical conditions, medication information, and medical history h. ECG signal features and summary statistics, such as the mean, median, standard deviation or sum of the ECG signal sample values within a given time period i. A confidence rating provided by the measurement device to indicate the quality of heart beat estimation, for example, for each beat or for sequential time periods.

j. Intra-beat interval measurements

In embodiments, a system for monitoring cardiac signal data, comprises:

a wearable medical sensor, the wearable medical sensor configured to detect cardiac signals from a mammal and estimate the R-peak location within the cardiac signal;

wherein the wearable medical sensor is configured to transmit an R-R interval time series and a time stamp to an intermediary device, the intermediary device configured to further transmit the R-R interval time series and time stamp to a server;

wherein the server is configured to infer the most probable rhythms and their onset/offset times from the R-R interval time series and time stamp, the server configured to filter the most probable rhythms according to a first criteria into a filtered data set;

wherein the server is configured to transmit the filtered data set back to the wearable sensor via the intermediary device; and wherein the sensor transmits the full resolution cardiac signal to the server for a time period surrounding each of the filtered events.

In certain embodiments, a system for monitoring cardiac signal data comprises:

a server configured to communicate with a wearable sensor, the wearable sensor configured to detect cardiac signals from a mammal and estimate the R peak location within the cardiac signal;

wherein the wearable sensor is configured to transmit an R-R interval time series and a time stamp to the server;

wherein the server is configured to infer the most probable rhythms and their onset/offset times from the R-R interval time series and time stamp, the server configured to filter the most probable rhythms according to a first criteria into a filtered data set; and wherein the server is configured to transmit a summary of the filtered data.

In particular embodiments, a server for monitoring cardiac signal data, comprises:

a portal configured to communicate with a wearable sensor, the wearable sensor configured to detect cardiac signals from a mammal and estimate the R peak location within the cardiac signal, wherein the wearable sensor is configured to transmit an R-R interval time series and a time stamp to an intermediary device, the intermediary device configured to further transmit the R-R interval time series and time stamp to a server;

a processor configured to infer the most probable rhythms and their onset/offset times from the R-R interval time series and time stamp, the processor configured to filter the most probable rhythms according to a first criteria into a filtered data set; and wherein the server is configured to transmit a summary of the filtered data set.

In embodiments, a non-transitory storage medium having computer-executable instructions stored thereon, the computer-executable instructions readable by a computing system comprising one or more computing devices, wherein the computer-executable instructions are executable on the computing system in order to cause the computing system to perform operations comprises: receiving, by a computing system through a communication link, physiological sensor data generated by a patient monitoring device, the physiological sensor data associated with a first patient; analyzing, by the computing system, the physiological sensor data to determine whether one or more points in the physiological data that are likely indicative of one or more predetermined set of conditions; and after determining that at least one of the one or more points in the physiological data is likely indicative of at least one of the one or more predetermined set of conditions, generating, by the computing system, an electronic data package for transmission to the patient monitoring device, the electronic data package including location data regarding the at least one of the one or more points in the physiological sensor data that are likely indicative of the at least one of the one or more predetermined set of conditions.

In certain embodiments, the physiological sensor data may comprise a sampling of interval data measured from the recorded signal data, the sampling of interval data of a data size less than the recorded signal data.

In particular embodiments, a system for monitoring physiological signals in a mammal may comprise: a wearable adhesive monitor configured to detect and record cardiac rhythm data from a mammal, the wearable adhesive monitor configured to extract a feature from the cardiac rhythm data; and wherein the wearable adhesive monitor is configured to transmit the feature to a processing device, the processing device configured to analyze the feature, identify locations of interest, and transmit the locations of interest back to the wearable adhesive monitor.

In certain embodiments, a system for assessing physiological sensor data from a patient monitoring device comprises: a computer processor and non-transitory computer-readable media combined with the computer processor configured to provide a program that includes a set of instructions stored on a first server, the set of instructions being executable by the computer processor, and further configured to execute a sensor data inference module of the program; the sensor data inference module of the program storing instructions to: receive physiological sensor data generated by a patient monitoring device, the physiological sensor data associated with a first patient; analyze the physiological sensor data to determine whether one or more points in the physiological data that are likely indicative of one or more predetermined set of conditions; and after determining that at least one of the one or more points in the physiological data is likely indicative of at least one of the one or more predetermined set of conditions, generating an electronic data package for transmission to the patient monitoring device, the electronic data package including location data regarding the at least one of the one or more points in the physiological sensor data that are likely indicative of the at least one of the one or more predetermined set of conditions.

In certain embodiments, a computerized method may comprise: accessing computer-executable instructions from at least one computer-readable storage medium; and executing the computer-executable instructions, thereby causing computer hardware comprising at least one computer processor to perform operations comprising: receiving, by a server computer through a communication link, physiological sensor data generated by a patient monitoring device, the physiological sensor data associated with a first patient; analyzing, by the server computer, the physiological sensor data to determine whether one or more points in the physiological data that are likely indicative of one or more predetermined set of conditions; and after determining that at least one of the one or more points in the physiological data is likely indicative of at least one of the one or more predetermined set of conditions, generating, by the server computer, an electronic data package for transmission to the patient monitoring device, the electronic data package including location data regarding the at least one of the one or more points in the physiological sensor data that are likely indicative of the at least one of the one or more predetermined set of conditions.

These and other aspects and embodiments of the invention are described in greater detail below, with reference to the drawing figures.

BRIEF DESCRIPTION OF THE DRAWINGS

FIGS. 1A and 1B are perspective and exploded profile views, respectively, of a physiological monitoring device, according to one embodiment.

FIGS. 3A, 3B, 3C, 3D, and 3E are perspective and exploded views of a flexible body and gasket of the physiological monitoring device, according to one embodiment.

FIGS. 6A and 6B are cross sectional views of the physiological monitoring device, according to one embodiment.

DETAILED DESCRIPTION OF EMBODIMENTS

Figure 1B:
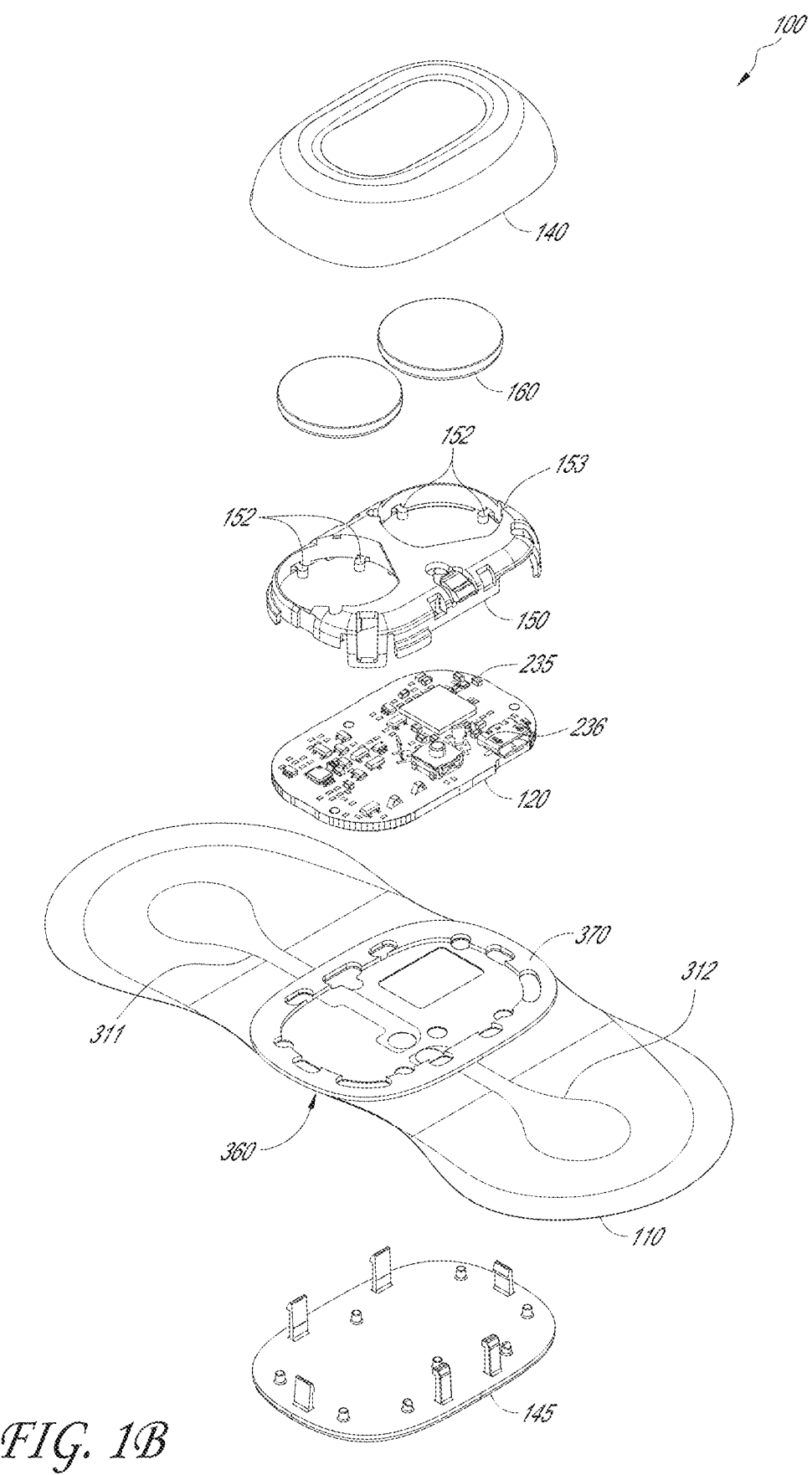

The following description is directed to a number of various embodiments. The described embodiments, however, may be implemented and/or varied in many different ways. For example, the described embodiments may be implemented in any suitable device, apparatus, or system to monitor any of a number of physiological parameters. For example, the following discussion focuses primarily on long-term, patch-based cardiac rhythm monitoring devices. In one alternative embodiment, a physiological monitoring device may be used, for example, for pulse oximetry and diagnosis of obstructive sleep apnea. The method of using a physiological monitoring device may also vary. In some cases, a device may be worn for one week or less, while in other cases, a device may be worn for at least seven days and/or for more than seven days, for example between fourteen days and twenty-one days or even longer. Many other alternative embodiments and applications of the described technology are possible. Thus, the following description is provided for exemplary purposes only. Throughout the specification, reference may be made to the term "conformal." It will be understood by one of skill in the art that the term "conformal" as used herein refers to a relationship between surfaces or structures where a first surface or structure adapts to the contours of a second surface or structure.

Since abnormal heart rhythms or arrhythmias can often be due to other, less serious causes, a key challenge is to determine when any of these symptoms are due to an arrhythmia. Oftentimes, arrhythmias occur infrequently and/or episodically, making rapid and reliable diagnosis difficult. As mentioned above, currently, cardiac rhythm monitoring is primarily accomplished through the use of devices, such as Holter monitors, that use short-duration (less than 1 day) electrodes affixed to the chest. Wires connect the electrodes to a recording device, usually worn on a belt. The electrodes need daily changing and the wires are cumbersome. The devices also have limited memory and recording time. Wearing the device interferes with patient movement and often precludes performing certain activities while being monitored, such as bathing. Further, Holter monitors are capital equipment with limited availability, a situation that often leads to supply constraints and corresponding testing delays. These limitations severely hinder the diagnostic usefulness of the device, the compliance of patients using the device, and the likelihood of capturing all important information. Lack of compliance and the shortcomings of the devices often lead to the need for additional devices, follow-on monitoring, or other tests to make a correct diagnosis.

Current methods to correlate symptoms with the occurrence of arrhythmias, including the use of cardiac rhythm monitoring devices, such as Holter monitors and cardiac event recorders, are often not sufficient to allow an accurate diagnosis to be made. In fact, Holter monitors have been shown to not lead to a diagnosis up to 90% of the time ("Assessment of the Diagnostic Value of 24-Hour Ambulatory Electrocardiographic Monitoring", by DE Ward et al. Biotelemetry Patient Monitoring, vol. 7, published in 1980).

Additionally, the medical treatment process to actually obtain a cardiac rhythm monitoring device and initiate monitoring is typically very complicated. There are usually numerous steps involved in ordering, tracking, monitoring, retrieving, and analyzing the data from such a monitoring device. In most cases, cardiac monitoring devices used today are ordered by a cardiologist or a cardiac electrophysiologist (EP), rather than the patient's primary care physician (PCP). This is of significance since the PCP is often the first physician to see the patient and determine that the patient's symptoms could be due to an arrhythmia. After the patient sees the PCP, the PCP will make an appointment for the patient to see a cardiologist or an EP. This appointment is usually several weeks from the initial visit with the PCP, which in itself leads to a delay in making a potential diagnosis as well as increases the likelihood that an arrhythmia episode will occur and go undiagnosed. When the patient finally sees the cardiologist or EP, a cardiac rhythm monitoring device will usually be ordered. The monitoring period can last 24 to 48 hours (Holter monitor) or up to a month (cardiac event monitor or mobile telemetry device). Once the monitoring has been completed, the patient typically must return the device to the clinic, which itself can be an inconvenience. After the data has been processed by the monitoring company or by a technician on-site at a hospital or office, a report will finally be sent to the cardiologist or EP for analysis. This complex process results in fewer patients receiving cardiac rhythm monitoring than would ideally receive it.

To address some of these issues with cardiac monitoring, the assignee of the present application developed various embodiments of a small, long-term, wearable, physiological monitoring device. One embodiment of the device is the Zio® Patch. Various embodiments are also described, for example, in U.S. Pat. Nos. 8,150,502, 8,160,682 8,244,335, 8,560,046, and 8,538,503, the full disclosures of which are hereby incorporated herein by reference. Generally, the physiological patch-based monitors described in the above references fit comfortably on a patient's chest and are designed to be worn for at least one week and typically two to three weeks. The monitors detect and record cardiac rhythm signal data continuously while the device is worn, and this cardiac rhythm data is then available for processing and analysis.

These smaller, long-term, patch-based physiological monitoring devices provide many advantages over prior art devices. At the same time, further improvements are desired. One of the most meaningful areas for improvement is to offer more timely notice of critical arrhythmias to managing clinicians. The hallmark of these initial embodiments was that—for reasons of performance, compliance and cost—the device only recorded information during the extended wear period, with analysis and reporting occurring after the recording completed. Thus, a desirable improvement would be to add the capability of either real-time or timely analysis of the collected rhythm information. While diagnostic monitors with such timely reporting capabilities currently exist, they require one or more electrical components of the system to be either regularly recharged or replaced. These actions are associated with reduced patient compliance and, in turn, reduced diagnostic yield. As such, a key area of improvement is to develop a physiologic monitor that can combine long-term recording with timely reporting without requiring battery recharging or replacement.

Patient compliance and device adhesion performance are two factors that govern the duration of the ECG record and consequently the diagnostic yield. Compliance can be increased by improving the patient's wear experience, which is affected by wear comfort, device appearance, and the extent to which the device impedes the normal activities of daily living. Given that longer ECG records provide greater diagnostic yield and hence value, improvements to device adhesion and patient compliance are desirable.

Signal quality is important throughout the duration of wear, but may be more important where the patient marks the record, indicating an area of symptomatic clinical significance. Marking the record is most easily enabled through a trigger located on the external surface of the device. However, since the trigger may be part of a skin-contacting platform with integrated electrodes, the patient can introduce significant motion artifacts when feeling for the trigger. A desirable device improvement would be a symptom trigger that can be activated with minimal addition of motion artifact.

Further, it is desirable for the device to be simple and cost effective to manufacture, enabling scalability at manufacturing as well as higher quality due to repeatability in process. Simplicity of manufacture can also lead to ease of disassembly, which enables the efficient recovery of the printed circuit board for quality-controlled reuse in another device. Efficient reuse of this expensive component can be important for decreasing the cost of the diagnostic monitor.

There remain clinical scenarios where still longer-duration and lower-cost solutions may be a valuable addition to a portfolio of cardiac ambulatory monitoring options. Inspiration for a potential solution to these needs can be found in the continuous heart rate sensing functionality that is increasingly being incorporated in a variety of consumer health and fitness products, including smart watches and wearable fitness bands. Although continuous heart rate data can be used to provide the user with information about their general fitness levels, it is more both more challenging and valuable to use this data to provide meaningful information related to their health and wellness. For example, the ability to detect potential arrhythmias from continuous heart rate data would enable consumer devices incorporating heart rate sensing functionality to serve as potential screening tools for the early detection of cardiac abnormalities. Such an approach could be clinically valuable in providing a long-term, cost-effective screening method for at-risk populations, for example, heart failure patients at risk for Atrial Fibrillation. Alternatively, this monitoring approach could be helpful in the long-term titration of therapeutic drug dosages to ensure efficaciousness while reducing side effects, for example, in the management of Paroxysmal Atrial Fibrillation. Beyond cardiac arrhythmia detection, the appropriate analysis of heart rate information could also yield insight into sleep and stress applications.

Long-term ambulatory monitoring with a physiologic device, such as an adhesive patch, has a number of clinical applications, particularly when timely information about the occurrence and duration of observed arrhythmias can be provided during the monitoring period. In terms of prevalence, particularly as driven by an aging population, efficiently detecting Atrial Fibrillation (AF) remains the most significant monitoring need. This need is not just evident for patients presenting with symptoms, but also—given the increased risk of stroke associated with this arrhythmia—for broader, population-based monitoring of asymptomatic AF in individuals at risk due to one or more factors of advanced age, the presence of chronic illnesses like Heart Disease, or even the occurrence of surgical procedures. For the latter group, both perioperative and post-procedure monitoring can be clinically valuable, and not just for procedures targeted at arrhythmia prevention (for example, the MAZE ablation procedure, or hybrid endo and epicardial procedures, both for treatment of AF), but also for general surgeries involving anesthesia. For some applications, the goal of ambulatory monitoring for Atrial Fibrillation will sometimes be focused on the simple binary question of yes or no—did AF occur in a given time period. For example, monitoring a patient following an ablation procedure will typically seek to confirm success, typically defined as the complete lack of AF occurrence. Likewise, monitoring a patient post-stroke will be primarily concerned with evaluating the presence of Atrial Fibrillation.

However, even in those scenarios, if AF occurs, it may be clinically meaningful to evaluate additional aspects to better characterize the occurrence, such as daily burden (% of time in AF each day), and duration of episodes (expressed, for example, as a histogram of episode duration, or as the percentage of episodes that extend beyond a specified limit, say six minutes), both either in absolute terms or in comparison to prior benchmarks (for example, from a baseline, pre-procedure monitoring result). Indeed, measuring daily AF burden, evaluating AF episode duration, and reviewing AF occurrence during sleep and waking periods, and evaluating the presence of AF in response to the degree of a patient's physical movement can be important in a variety of clinical scenarios, including evaluating the effectiveness of drug-based treatment for this arrhythmia.

Making this information available in a timely manner during the monitoring period could allow the managing physician to iteratively titrate treatment, for example, by adjusting the dosage and frequency of a novel oral anticoagulant drug (NOAC) until management was optimized. A further example of this management paradigm is for the patient to be notified of asymptomatic AF—either directly by the device through audible or vibration-based alert, through notification from an application connected to the device, or via phone, email or text-message communication from the managing clinician—for the timely application of a "pill in the pocket" for AF management.

The theme of timely management and/or intervention is certainly evident in situations where clinically significant arrhythmias are observed, for example, asymptomatic second-degree and complete Heart Block, extended pauses, high-rate supraventricular tachycardias, prolonged ventricular tachycaridas, and ventricular fibrillation. For example, the clinical scenario where an extended pause or complete heart block causes Syncope is a particularly significant case where the availability of a timely and dependable monitoring method could reduce or even eliminate the need for in-hospital monitoring of at-risk patients. The theme can also extend to more subtle changes in morphology, for example, QT prolongation in response to medications, which has been shown to have significant cardiac safety implications. Timely awareness of such prolongation could lead, for example, to early termination of clinical studies evaluating drug safety and effectiveness or, alternatively, to adjusting the dosage or frequency as a means to eliminate observed prolongation.

Physiological Monitoring Devices

Referring to FIGS. 1A and 1B, perspective and exploded profile views of one embodiment of a physiological monitoring device 100 are provided. As seen in FIG. 1A, physiological monitoring device 100 may include a flexible body 110 coupled with a watertight, rigid housing 115. Flexible body 110 (which may be referred to as "flexible substrate" or "flexible construct") typically includes two wings 130, 131, which extend laterally from rigid housing 115, and two flexible electrode traces 311, 312, each of which is embedded in one of wings 130, 131. Each electrode trace 311, 312 is coupled, on the bottom surface of flexible body 110, with a flexible electrode (not visible in FIG. 1A). The electrodes are configured to sense heart rhythm signals from a patient to which monitoring device 100 is attached. Electrode traces 311, 312 then transmit those signals to electronics (not visible in FIG. 1A) housed in rigid housing 115. Rigid housing 115 also typically contains a power source, such as one or more batteries.

The combination of a highly flexible body 110, including flexible electrodes and electrode traces 311, 312, with a very rigid housing 115 may provide a number of advantages. A key advantage is high fidelity signal capture. The highly conformal and flexible wings 130, 131, electrodes and traces 311, 312 limit the transmission of external energy to the electrode-skin interface. If motion is imparted to the rigid housing 115, for example, the system of conformal adhesion to the skin limits the extent to which that motion affects the monitored signal. Flexible electrode traces 311, 312 generally may help provide conformal contact with the subject's skin and may help prevent electrodes 350 (electrodes 350 are not visible in FIG. 1, but are visible in FIG. 6A described below) from peeling or lifting off of the skin, thereby providing strong motion artifact rejection and better signal quality by minimizing transfer of stress to electrodes 350. Furthermore, flexible body 110 includes a configuration and various features that facilitate comfortable wearing of device 100 by a patient for fourteen (14) days or more without removal. Rigid housing 115, which typically does not adhere to the patient in the embodiments described herein, includes features that lend to the comfort of device 100. Hinge portions 132 are relatively thin, even more flexible portions of flexible body 110. They allow flexible body 110 to flex freely at the area where it is joined to rigid housing 115. This flexibility enhances comfort, since when the patient moves, housing 115 can freely lift off of the patient's skin. Electrode traces 311, 312 are also very thin and flexible, to allow for patient movement without signal distortion.

Referring now to FIG. 1B, a partially exploded view of physiological monitoring device 100 illustrates component parts that make up, and that are contained within, rigid housing 115 in greater detail. In this embodiment, rigid housing 115 includes an upper housing member 140, which detachably couples with a lower housing member 145. Sandwiched between upper housing member 140 and lower housing member 145 are an upper gasket 370, and a lower gasket 360 (not visible on FIG. 1B but just below upper gasket 370). Gaskets 370, 360 help make rigid housing member 115 watertight when assembled. A number of components of monitoring device 100 may be housed between upper housing member 140 and lower housing member 145. For example, in one embodiment, housing 115 may contain a portion of flexible body 110, a printed circuit board assembly (PCBA) 120, a battery holder 150, and two batteries 160. Printed circuit board assembly 120 is positioned within housing 115 to contact electrode traces 311, 312 and batteries 160. In various embodiments, one or more additional components may be contained within or attached to rigid housing 115. Some of these optional components are described further below, in reference to additional drawing figures.

Battery holder 150, according to various alternative embodiments, may hold two batteries (as in the illustrated embodiment), one battery, or more than two batteries. In other alternative embodiments, other power sources may be used. In the embodiment shown, battery holder 150 includes multiple retain tabs 153 for holding batteries 160 in holder 150. Additionally, battery holder 150 includes multiple feet 152 to establish correct spacing of batteries 160 from the surface of PCBA 120 and ensure proper contact with spring fingers 235 and 236. Spring fingers 235 and 236 are used in this embodiment rather than soldering batteries 160 to PCBA 120. Although soldering may be used in alternative embodiments, one advantage of spring fingers 235 and 236 is that they allow batteries 160 to be removed from PCBA 120 and holder 150 without damaging either of those components, thus allowing for multiple reuses of both.

Eliminating solder connections also simplifies and speeds up assembly and disassembly of monitoring device 100.

In some embodiments, upper housing member 140 may act as a patient event trigger. When a patient is wearing physiological monitoring device 100 for cardiac rhythm monitoring, it is typically advantageous for the patient to be able to register with device 100 (for example, log into the device's memory) any cardiac events perceived by the patient. If the patient feels what he/she believes to be an episode of heart arrhythmia, for example, the patient may somehow trigger device 100 and thus provide a record of the perceived event. In some embodiments, trigger of perceived events by the patient may initiate transmission of data associated with the triggered event. In some embodiments, trigger of perceived events may simply mark a continuous record with the location of the triggered event. In some embodiments, both transmission of associated data as well as marking of the continuous record may occur. At some later time, the patient's recorded symptom during the perceived event could be compared with the patient's actual heart rhythm, recorded by device 100, and this may help determine whether the patient's perceived events correlate with actual cardiac events. One problem with patient event triggers in currently available wearable cardiac rhythm monitoring devices, however, is that a small trigger may be hard to find and/or activate, especially since the monitoring device is typically worn under clothing. Additionally, pressing a trigger button may affect the electronics and/or the electrodes on the device in such a way that the recorded heart rhythm signal at that moment is altered simply by the motion caused to the device by the patient triggering. For example, pressing a trigger may jar one or both of the electrodes in such a way that the recorded heart rhythm signal at that moment appears like an arrhythmia, even if no actual arrhythmia event occurred. Additionally, there is a chance that the trigger may be inadvertently activated, for instance while sleeping or laying on the monitoring device.

In the embodiment shown in FIGS. 1A and 1B, however, rigid housing 115 is sufficiently rigid, and flexible body 110 is sufficiently flexible, that motion applied to housing 115 by a patient may rarely or ever cause an aberrant signal to be sensed by the electrodes. In this embodiment, the central portion of upper housing member 140 is slightly concave and, when pressed by a patient who is wearing device 100, this central portion depresses slightly to trigger a trigger input on PCBA 120. Because the entire upper surface of rigid housing 115 acts as the patient event trigger, combined with the fact that it is slightly concave, it will generally be quite easy for a patient to find and push down the trigger, even under clothing. Additionally, the concave nature of the button allows it to be recessed which protects it from inadvertent activations. Thus, the present embodiment may alleviate some of the problems encountered with patient event triggers on currently available heart rhythm monitors. These and other aspects of the features shown in FIGS. 1A and 1B will be described in further detail below.

Figure 2A:
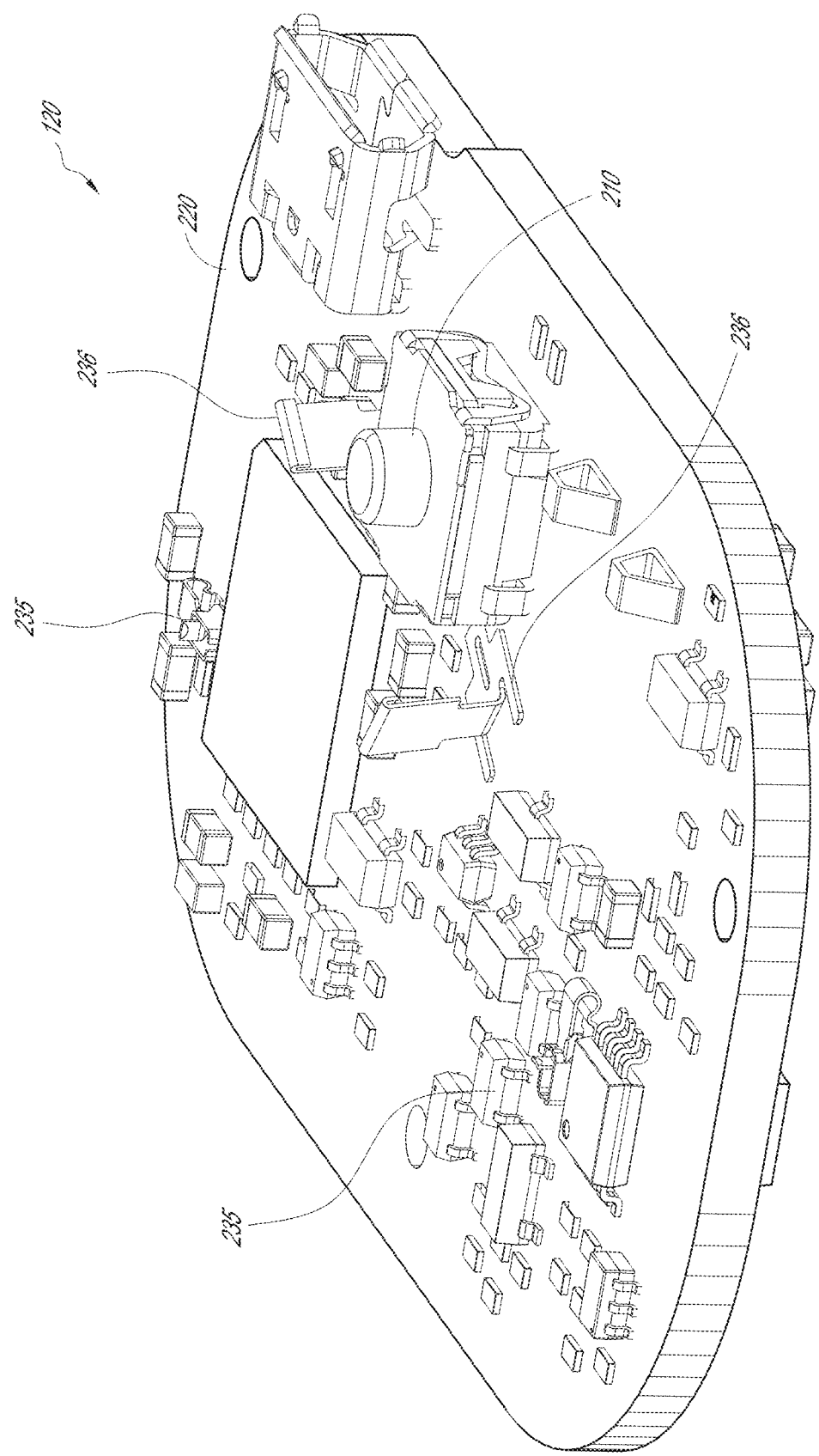
FIGS. 2A and 2B are top perspective and bottom perspective views, respectively, of a printed circuit board assembly of the physiological monitoring device, according to one embodiment.
Figure 2B:
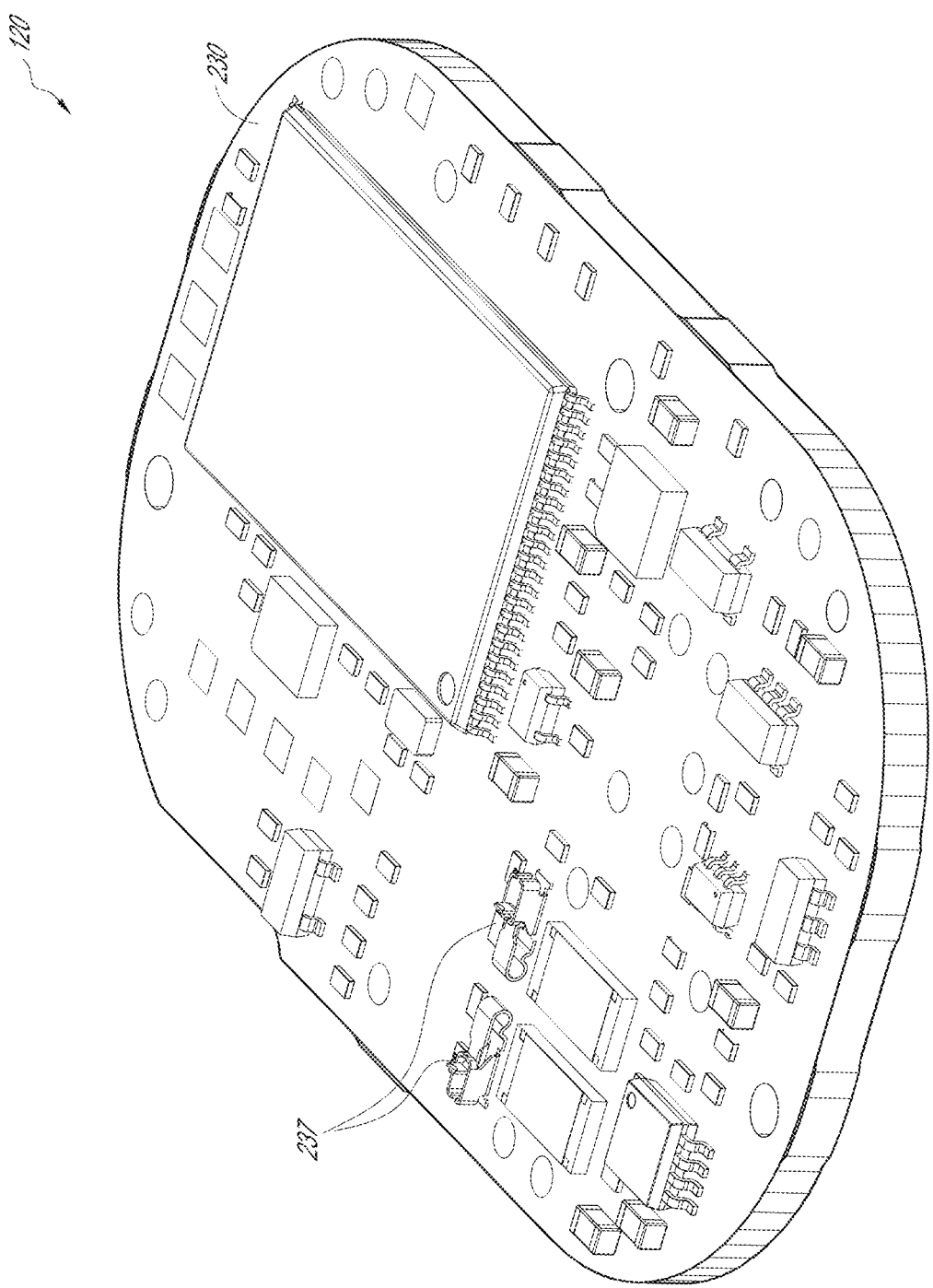

Referring now to the embodiments in FIGS. 2A and 2B, printed circuit board assembly 120 (or PCBA) may include a top surface 220, a bottom surface 230, a patient trigger input 210 and spring contacts 235, 236, and 237. Printed circuit board assembly 120 may be used to mechanically support and electrically connect electronic components using conductive pathways, tracks or electrode traces 311, 312. Furthermore, because of the sensitive nature of PCBA 120 and the requirement to mechanically interface with rigid body 115, it is beneficial to have PCBA 120 be substantially rigid enough to prevent unwanted deflections which may introduce noise or artifact into the ECG signal. This is especially possible during patient trigger activations when a force is transmitted through rigid body 115 and into PCBA 120. One way to ensure rigidity of the PCBA is in some embodiments, to ensure that the thickness of the PCBA is relatively above a certain value. For example, a thickness of at least about 0.08 cm is desirable and, more preferably, a thickness of at least about 0.17 cm is desirable. In this application, PCBA 120 may also be referred to as, or substituted with, a printed circuit board (PCB), printed wiring board (PWB), etched wiring board, or printed circuit assembly (PCA). In some embodiments, a wire wrap or point-to-point construction may be used in addition to, or in place of, PCBA 120. PCBA 120 may include analog circuits and digital circuits.

Patient trigger input 210 may be configured to relay a signal from a patient trigger, such as upper housing member 140 described above, to PCBA 120. For example, patient trigger input 210 may be a PCB switch or button that is responsive to pressure from the patient trigger (for example, the upper surface of upper housing portion 140). In various embodiments, patient trigger input 210 may be a surface mounted switch, a tactile switch, an LED illuminated tactile switch, or the like. In some embodiments, patient trigger input 210 may also activate an indicator, such as an LED. Certain embodiments may involve a remotely located trigger such as on a separate device or as a smart phone app.

One important challenge in collecting heart rhythm signals from a human or animal subject with a small, two-electrode physiological monitoring device such as device 100 described herein, is that having only two electrodes can sometimes provide a limited perspective when trying to discriminate between artifact and clinically significant signals. For example, when a left-handed patient brushes her teeth while wearing a small, two-electrode physiological monitoring device on her left chest, the tooth brushing may often introduce motion artifact that causes a recorded signal to appear very similar to Ventricular Tachycardia, a serious heart arrhythmia. Adding additional leads (and, hence, vectors) is the traditional approach toward mitigating this concern, but this is typically done by adding extra wires adhered to the patient's chest in various locations, such as with a Holter monitor. This approach is not consistent with a small, wearable, long term monitor such as physiological monitoring device 100.

An alternate approach to the problem described above is to provide one or more additional data channels to aid signal discrimination. In some embodiments, for example, device 100 may include a data channel for detecting patch motion. In certain embodiments, an accelerometer or other suitable device may provide patch motion by simply analyzing the change in magnitude of a single axis measurement, or alternatively of the combination of all three axes. The accelerometer may record device motion at a sufficient sampling rate to allow algorithmic comparison of its frequency spectrum with that of the recorded ECG signal. If there is a match between the motion and recorded signal, it is clear that the device recording in that time period is not from a clinical (for example, cardiac) source, and thus that portion of the signal can be confidently marked as artifact. This technique may be particularly useful in the tooth brushing motion example aforementioned, where the rapid frequency of motion as well as the high amplitude artifact is similar to the heart rate and morphology, respectively, of a potentially life-threatening arrhythmia like Ventricular Tachycardia. Other suitable devices described herein this section and elsewhere in the specification may also be utilized to provide motion information.

In some embodiments, using the magnitude of all three axes for such an analysis would smooth out any sudden changes in values due to a shift in position rather than a change in activity. In other embodiments, there may be some advantage in using a specific axis of measurement such as along the longitudinal axis of the body to focus on a specific type of artifact introduced by upward and downward movements associated with walking or running. In a similar vein, the use of a gyroscope in conjunction with the accelerometer may provide further resolution as to the nature of the motion experienced. While whole body movements may be sufficiently analyzed with an accelerometer on its own, specific motion of interest such as rotational motion due to arm movement is sufficiently complex that an accelerometer alone might not be able to distinguish.

In addition to detecting motion artifact, an accelerometer tuned to the dynamic range of human physical activities may provide activity levels of the patient during the recording, which can also enhance accuracy of algorithmic true arrhythmia detection. Given the single-lead limitation of device 100, arrhythmias that require observation of less prominent waves (for example P-wave) in addition to rate changes such as Supraventricular Tachycardia pose challenges to both computerized algorithms as well as the trained human eye. This particular arrhythmia is also characterized by the sudden nature of its onset, which may be more confidently discriminated from a non-pathological Sinus Tachycardia if a sudden surge in the patient's activity level is detected at the same time as the increase in heart rate. Broadly speaking, the provision of activity information to clinical professionals may help them discriminate between exercise-induced arrhythmia versus not. As with motion artifact detection, a single-axis accelerometer measurement optimized to a particular orientation may aid in more specifically determining the activity type such as walking or running. This additional information may help explain symptoms more specifically and thereby affect the subsequent course of therapeutic action.

In certain embodiments, an accelerometer with 3 axes may confer advantages beyond what magnitude of motions can provide. When the subject is not rapidly moving, 3-dimensional accelerometer readings may approximate the tilt of PCBA 120, and therefore body orientation relative to its original orientation. The original body orientation can be assumed to be in either an upright or supine position which is required for appropriate positioning and application of the device to the body. This information may aid in ruling out certain cardiac conditions that manifest as beat-to-beat morphology changes, such as cardiac alternans where periodic amplitude changes are observed, often in heart failure cases. Similar beat-to-beat morphology changes are observable in healthy subjects upon shift in body position due to the shift in heart position relative to the electrode vector, for example from an upright to a slouching position. By design, the single-channel device 100 does not have an alternate ECG channel to easily rule out potential pathological shifts in morphology, however, correlation with shifts in body orientation will help explain these normal changes and avoid unnecessary treatment due to false diagnosis.

In other embodiments, the accelerometer may also be used as a sleep indicator, based on body orientation and movement. When presenting clinical events (for example, pauses), it is diagnostically helpful to be able to present information in a manner that clearly separates events that occurred during sleep from those during waking hours. In fact, certain algorithms such as for ECG-derived respiratory rate only make sense to run when the patient is in a relatively motionless state and therefore subtle signal modulation introduced by chest movement due to breathing is observable. Respiratory rate information is useful as one channel of information necessary to detect sleep apnea in certain patient populations.

In certain embodiments, the accelerometer may also be used to detect free-falls, such as fainting. With an accelerometer, device 100 may be able to mark fainting (syncope) and other free-fall events without relying on patient trigger. In some embodiments, such free-fall event triggers may initiate transmission of associated data. In order to allow timely detection of such critical events, yet considering the battery and memory limitations of a small, wearable device such as device 100, acquisition of accelerometer readings may be done in bursts, where only interesting information such as a potential free fall is written to memory at a high sampling rate. An expansion of this event-trigger concept is to use specific tapping motions on device 100 as a patient trigger instead of or in conjunction with the button previously described. The use and detection of multiple types of tapping sequences may provide better resolution and accuracy into what exactly the patient was feeling, instead of relying on the patient to manually record their symptom and duration in a trigger log after the fact. An example of such added resolution is to indicate the severity of the symptom by the number of sequential taps.

Alternatively, in other embodiments, optical sensors may be used to distinguish between device motion and patient body motion. Further, in additional embodiments, the device may not require a button or trigger. In still more embodiments, suitable devices described herein this section or elsewhere in the specification may also be used.

Another optional data channel that may be added to physiological monitoring device 100 is a channel for detecting flex and/or bend of device 100. In various embodiments, for example, device 100 may include a strain gauge, piezoelectric sensor or optical sensor to detect motion artifact in device 100 itself and thus help to distinguish between motion artifact and cardiac rhythm data. Yet another optional data channel for device 100 may be a channel for detecting heart rate. For example, a pulse oximeter, microphone or stethoscope may provide heart rate information. Redundant heart rate data may facilitate discrimination of ECG signals from artifact. This is particularly useful in cases where arrhythmia such as Supraventricular Tachycardia is interrupted by artifact, and decisions must be made whether the episode was actually multiple shorter episodes or one sustained episode. Another data channel may be included for detecting ambient electrical noise. For example, device 100 may include an antenna for picking up electromagnetic interference. Detection of electromagnetic interference may facilitate discrimination of electrical noise from real ECG signals. Any of the above-described data channels may be stored to support future noise discrimination or applied for immediate determination of clinical validity in real-time.

Figure 3A:
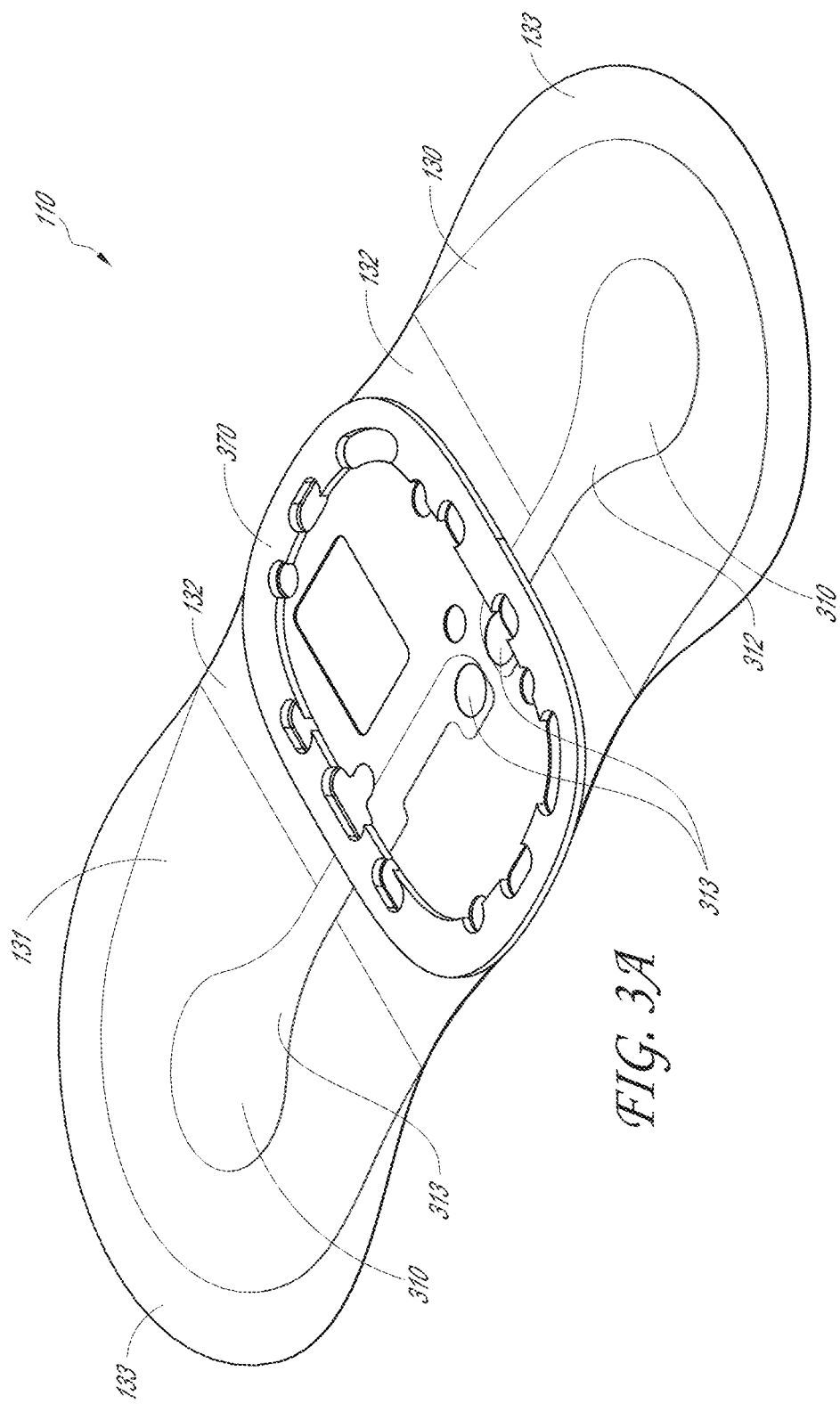
Figure 3B:
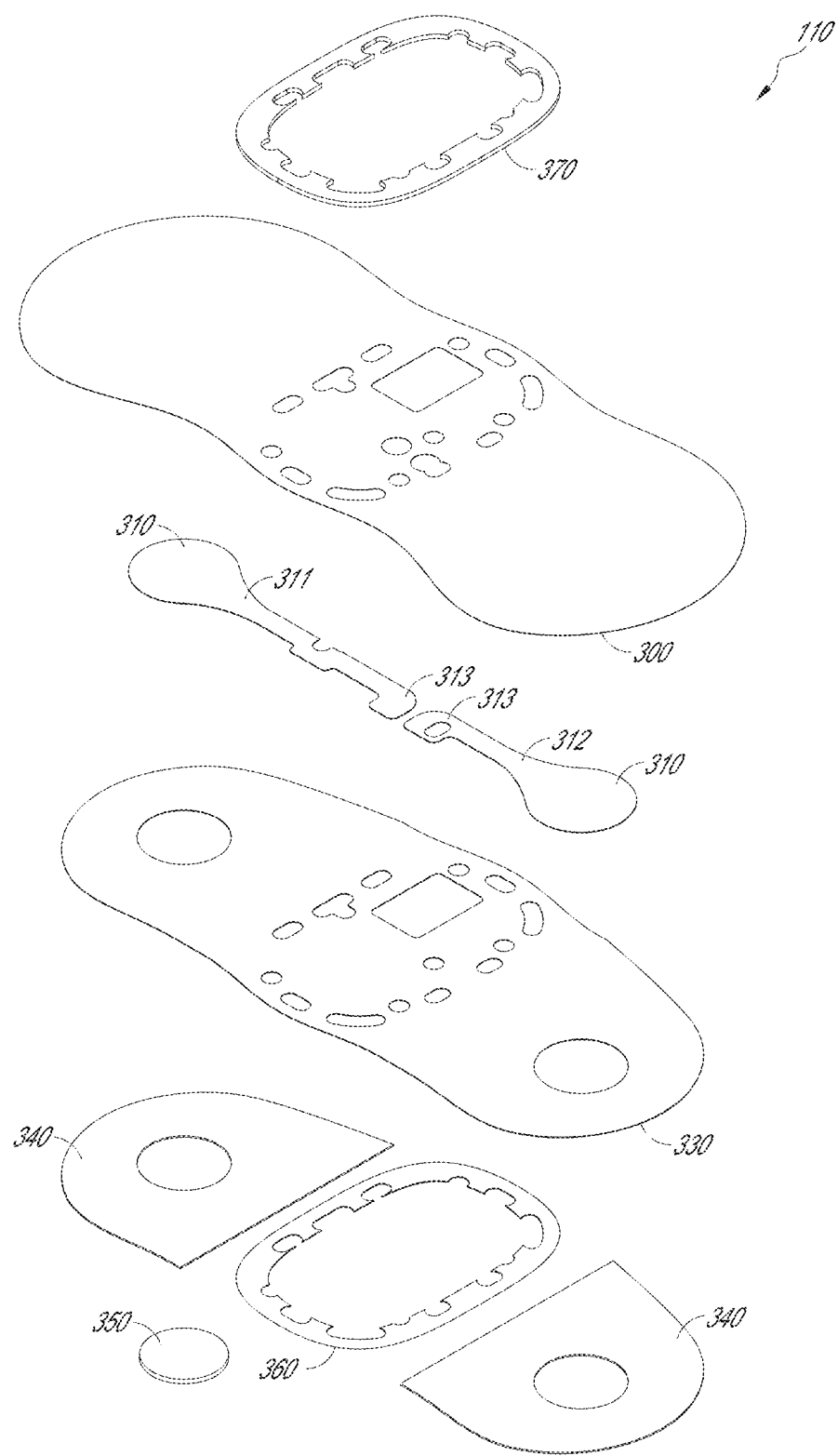

With reference now to the embodiments of FIGS. 3A and 3B, flexible body 110 is shown in greater detail. As illustrated in FIG. 3A, flexible body 110 may include wings 130, 131, a thin border 133 (or "rim" or "edge") around at least part of each wing 130, 131, electrode traces 311, 312, and a hinge portion 132 (or "shoulder") at or near a junction of each wing 130, 131 with rigid housing 115. Also shown in FIG. 3A is upper gasket 370, which is not considered part of flexible body 110 for this description, but which facilitates attachment of flexible body 110 to rigid housing 115.

Hinge portions 132 are relatively thin, even more flexible portions of flexible body 110. They allow flexible body 110 to flex freely at the area where it is joined to rigid housing 115. This flexibility enhances comfort, since when the patient moves, housing 115 can freely lift off of the patient's skin. Electrode traces 311, 312 are also very thin and flexible, to allow for patient movement without signal distortion. Borders 133 are portions of flexible body 110 that is thinner than immediately adjacent portions and that provide for a smooth transition from flexible body 110 to a patient's skin, thus preventing edge-lift and penetration of dirt or debris below flexible body 110.

As shown in greater detail in FIG. 3B, flexible body 110 may include multiple layers. As mentioned previously, in some embodiments, upper gasket 370 and lower gasket 360 are not considered part of flexible body 110 for the purposes of this description but are shown for completeness of description. This distinction is for ease of description only, however, and should not be interpreted to limit the scope of the described embodiments. Flexible body 110 may include a top substrate layer 300, a bottom substrate layer 330, an adhesive layer 340, and flexible electrodes 350. Top and bottom substrate layers 300, 330 may be made of any suitable, flexible material, such as one or more flexible polymers. Suitable flexible polymers can include, but are not limited to, polyurethane, polyethylene, polyester, polypropylene, nylon, teflon and carbon impregnated vinyl. The material of substrate layers 300, 330 may be selected based on desired characteristics. For example, the material of substrate layers 300, 330 may be selected for flexibility, resilience, durability, breathability, moisture transpiration, adhesion and/or the like. In one embodiment, for example, top substrate layer 300 may be made of polyurethane, and bottom substrate layer 330 may be made of polyethylene or alternatively polyester. In other embodiments, substrate layers 300, 330 may be made of the same material. In yet another embodiment, substrate layer 330 may contain a plurality of perforations in the area over adhesive layer 340 to provide for even more breathability and moisture transpiration. In various embodiments, physiological monitoring device 100 may be worn continuously by a patient for as many as 14-21 days or more, without removal during the time of wear and with device 100 being worn during showering, exercising and the like. Thus, the material(s) used and the thickness and configuration of substrate layers 300, 330 affect the function of physiological monitoring device 100. In some embodiments, the material of substrate layers 300, 330 acts as an electric static discharge (ESD) barrier to prevent arcing.

Typically, top and bottom substrate layers 300, 330 are attached to one another via adhesive placed on one or both layers 300, 330. For example, the adhesive or bonding substance between substrate layers 300, 330 may be an acrylic-based, rubber-based, or silicone-based adhesive. In other alternative embodiments, flexible body 110 may include more than two layers of flexible material.

In addition to the choice of material(s), the dimensions—thickness, length and width—of substrate layers 300, 330 may be selected based on desired characteristics of flexible body 110. For example, in various embodiments, the thickness of substrate layers 300, 330 may be selected to give flexible body 110 an overall thickness of between about 0.1 mm to about 1.0 mm. According to various embodiments, flexible body 110 may also have a length of between about 7 cm and 15 cm and a width of about 3 cm and about 6 cm. Generally, flexible body 110 will have a length sufficient to provide a necessary amount of separation between electrodes 350. For example, in one embodiment a distance from the center of one electrode 350 to the center of the other electrode 350 should be at least about 6.0 cm and more preferably at least about 8.5 cm. This separation distance may vary, depending on the application. In some embodiments, substrate layers 300, 330 may all have the same thickness. Alternatively, the two substrate layers 300, 330 may have different thicknesses.

As mentioned above, hinge portions 132 allow the rigid body 115 to lift away from the patient while flexible body 110 remains adhered to the skin. The functionality of hinge portions 132 is critical in allowing the device to remain adhered to the patient throughout various activities that may stretch and compress the skin. Furthermore, hinge portions 132 allow for significantly improved comfort while wearing the device. Generally, hinge portions 132 will be sufficiently wide enough to provide adequate lift of rigid body 115 without creating too large of a peel force on flexible body 110. For example, in various embodiments, the width of hinge portion 132 should be at least about 0.25 cm and more preferably at least about 0.75 cm.

Additionally, the shape or footprint of flexible body 110 may be selected based on desired characteristics. As seen in FIG. 3A, wings 130, 131 and borders 133 may have rounded edges that give flexible body 110 an overall "peanut" shape. However, wings 130, 131 can be formed in any number of different shapes such as rectangles, ovals, loops, or strips. In the embodiment shown in FIGS. 3A and 3B, the footprint top substrate layer 300 is larger than the footprint of bottom substrate layer 330, with the extension of top substrate layer 300 forming borders 133. Thus, borders 133 are made of the same polyurethane material that top layer 300 is made of. Borders 133 are thinner than an adjacent portion of each wing 130, 131, since they includes only top layer 300. The thinner, highly compliant rim 133 will likely enhance adherence of physiologic monitoring device 100 to a patient, as it provides a transition from an adjacent, slightly thicker portion of wings 130, 131 to the patient's skin and thus helps prevent the edge of device 110 from peeling up off the skin. Border 133 may also help prevent the collection of dirt and other debris under flexible body 110, which may help promote adherence to the skin and also enhance the aesthetics of device 110. In alternative embodiments, the footprint of substrate layers 300, 330 may be the same, thus eliminating borders 133.

While the illustrated embodiments of FIGS. 1A-3B include only two wings 130, 131, which extend from rigid housing 115 in approximately opposite directions (for example, at a 180-degree angle relative to each other), other configurations are possible in alternative embodiments. For example, in some embodiments, wings 130, 131 may be arranged in an asymmetrical orientation relative to one another and/or one or more additional wings may be included. As long as sufficient electrode spacing is provided to permit physiological signal monitoring, and as long as wings 130, 131 are configured to provide extended attachment to the skin, any suitable configuration and number of wings 130, 131 and electrode traces 311, 312 may be used. The embodiments described above have proven to be advantageous for adherence, patient comfort and accuracy of collected heart rhythm data, but in alternative embodiments it may be possible to implement alternative configurations.

Adhesive layer 340 is an adhesive that is applied to two portions of the bottom surface of bottom substrate layer 330, each portion corresponding to one of wings 130, 131. Adhesive layer 340 thus does not extend along the portion of bottom substrate layer 330 upon which rigid housing 115 is mounted. Adhesive layer 340 may be made of any suitable adhesive, although certain adhesives have been found to be advantageous for providing long term adhesion to patient skin with relative comfort and lack of skin irritation. For example, in one embodiment, adhesive layer 340 is a hydrocolloid adhesive. In another embodiment, the adhesive layer 340 is comprised of a hydrocolloid adhesive that contains naturally-derived or synthetic absorbent materials which take up moisture from the skin during perspiration.

With reference now to FIG. 3B, each of the two portions of adhesive layer 340 includes a hole, into which one of electrodes 350 fits. Electrodes 350 are made of flexible material to further provide for overall conformability of flexible body 110. In one embodiment, for example, flexible electrodes 350 may be made of a hydrogel 350. Electrodes 350 generally provide conformal, non-irritating contact with the skin to provide enhanced electrical connection with the skin and reduce motion artifact. In some embodiments, hydrogel electrodes 350 may be punched into adhesive layer 340, thus forming the holes and filling them with hydrogel electrodes 350. In one alternative embodiment, electrodes 350 and adhesive 340 may be replaced with an adhesive layer made of a conductive material, such that the entire adhesive layer on the underside of each wing 130, 131 acts as an electrode. Such an adhesive layer may include a hybrid adhesive/conductive substance or adhesive substance mixed with conductive elements or particles. For example, in one embodiment, such an adhesive layer may be a hybrid of a hydrogel and a hydrocolloid adhesive. Rigid housing 115 of FIG. 1A also protects the electronics and power source contained in housing 120, enhances the ability of a patient to provide an input related to a perceived cardiac event, and allows for simple manufacturing and reusability of at least some of the contents of housing 115. These and other features of physiological monitoring device 100 are described in greater detail below.

As discussed above, in some embodiments, adhesive layer 340 may cover a portion of the underside of lower substrate layer 330, such that at least a portion of the bottom side of flexible body 110 does not include adhesive layer 340. As seen in FIG. 3A, hinges 132 may be formed in the flexible body 110 as portions of each wing 130, 131 on which adhesive layer 340 is not applied. Hinge portions 132 are generally located at or near the junction of flexible body 110 with rigid housing 115, and thus provide for flexing of device 100 to accommodate patient movement. In some embodiments, hinge portions 132 may have a width that is less than that of adjacent portions of wings 130, 131, thus giving device 100 its "peanut" shape mentioned above. As shown in FIG. 8, as a subject moves, device 100 flexes along with patient movement. Device flexion may be severe and is likely to occur many times during long term monitoring. Hinge portions 132 may allow for dynamic conformability to the subject, while the rigidity of rigid housing 115 may allow housing 115 to pop up off the patient's skin during device flexion, thus preventing peeling of the device 100 off of the skin at its edge.

Flexible body 110 further includes two electrode traces 311, 312 sandwiched between upper substrate layer 300 and lower substrate layer 330. Each electrode trace 311, 312 may include an electrode interface portion 310 and an electro-cardiogram circuit interface portion 313. As illustrated in the embodiments of FIGS. 3C and 3D, ECG circuit interface portions 313 are in physical contact with spring fingers 237 and provide electrical communication with PCBA 120 when device 100 or zoomed-in device portion 101 is assembled. Electrode interface portions 310 contact hydrogel electrodes 350. Thus, electrode traces 311, 312 transmit cardiac rhythm signals (and/or other physiological data in various embodiments) from electrodes 350 to PCBA 120.

The material and thickness of electrode traces 311, 312 are important for providing a desired combination of flexibility, durability and signal transmission. For example, in one embodiment, electrode traces 311, 312 may include a combination of silver (Ag) and silver chloride (AgCl). The silver and silver chloride may be disposed in layers. For example, one embodiment of electrode traces 311, 312 may include a top layer of silver, a middle layer of carbon impregnated vinyl, and a bottom (patient-facing) layer of silver chloride. In another embodiment, both top and bottom layers of electrode traces 311, 312 may be made of silver chloride. In one embodiment, the top and bottom layers may be applied to the middle layer in the form of silver ink and silver chloride ink, respectively. In an alternative embodiment, each electrode trace may include only two layers, such as a top layer of silver and a bottom layer of silver chloride. In various embodiments, the material of a bottom layer of each electrode trace 311, 312, such as AgCl, may be selected to match the chemistry of the hydrogel electrodes 350 and create a half-cell with the body of the subject.

The thickness of the electrode traces 311, 312 may be selected to optimize any of a number of desirable properties. For example, in some embodiments, at least one of the layers of electrode traces 311, 312 can be of a sufficient thickness to minimize or slow depletion of the material from an anode/cathode effect over time. Additionally, the thickness may be selected for a desired flexibility, durability and/or signal transmission quality.

Figure 3E:
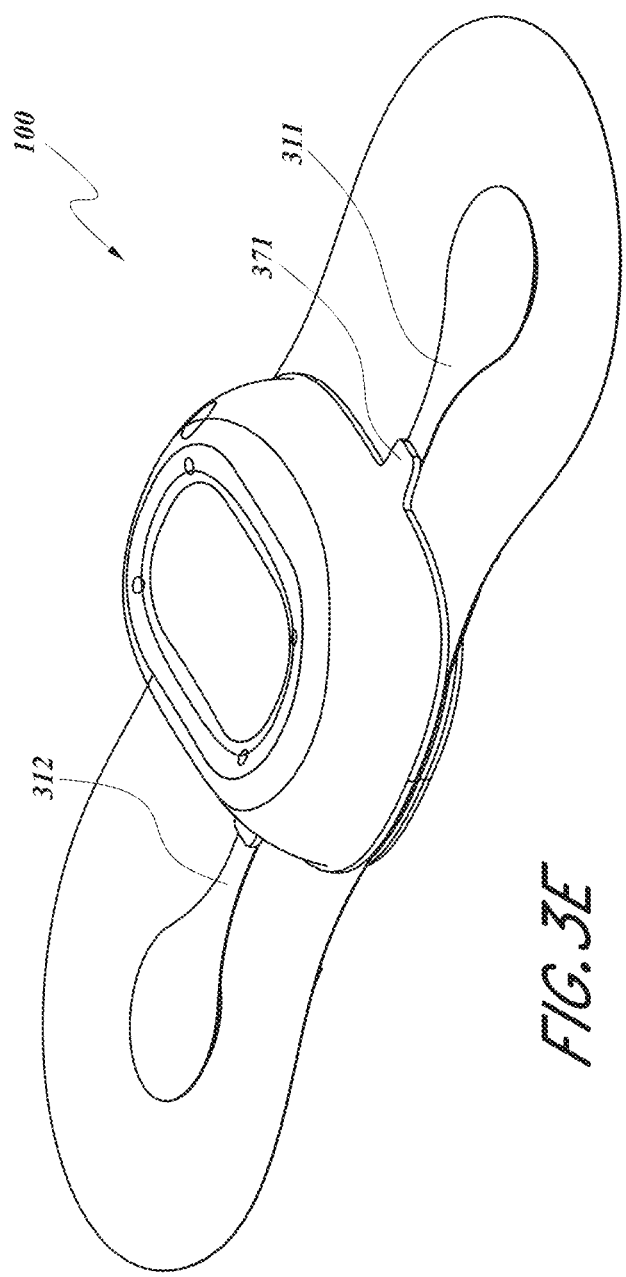

As mentioned above, in some embodiments, top gasket 370 and bottom gasket 360 may be attached upper substrate 300 and lower substrate 330 of flexible body 110. Gaskets 360, 370 may be made of any suitable material, such as urethane, which provides a water tight seal between the upper housing member 140 and lower housing member 145 of rigid housing 115. In one embodiment, top gasket 370 and/or bottom gasket 360 may include an adhesive surface. FIG. 3E depicts yet another embodiment where top gasket 370 includes tabs 371 that protrude away from the profile of top housing 140 while still being adhered to upper substrate 300. The tabs 371 cover a portion of electrode traces 311, 312 and provide a strain relief for the traces at the point of highest stress where the flexible body meets the rigid housing.

Figure 4:
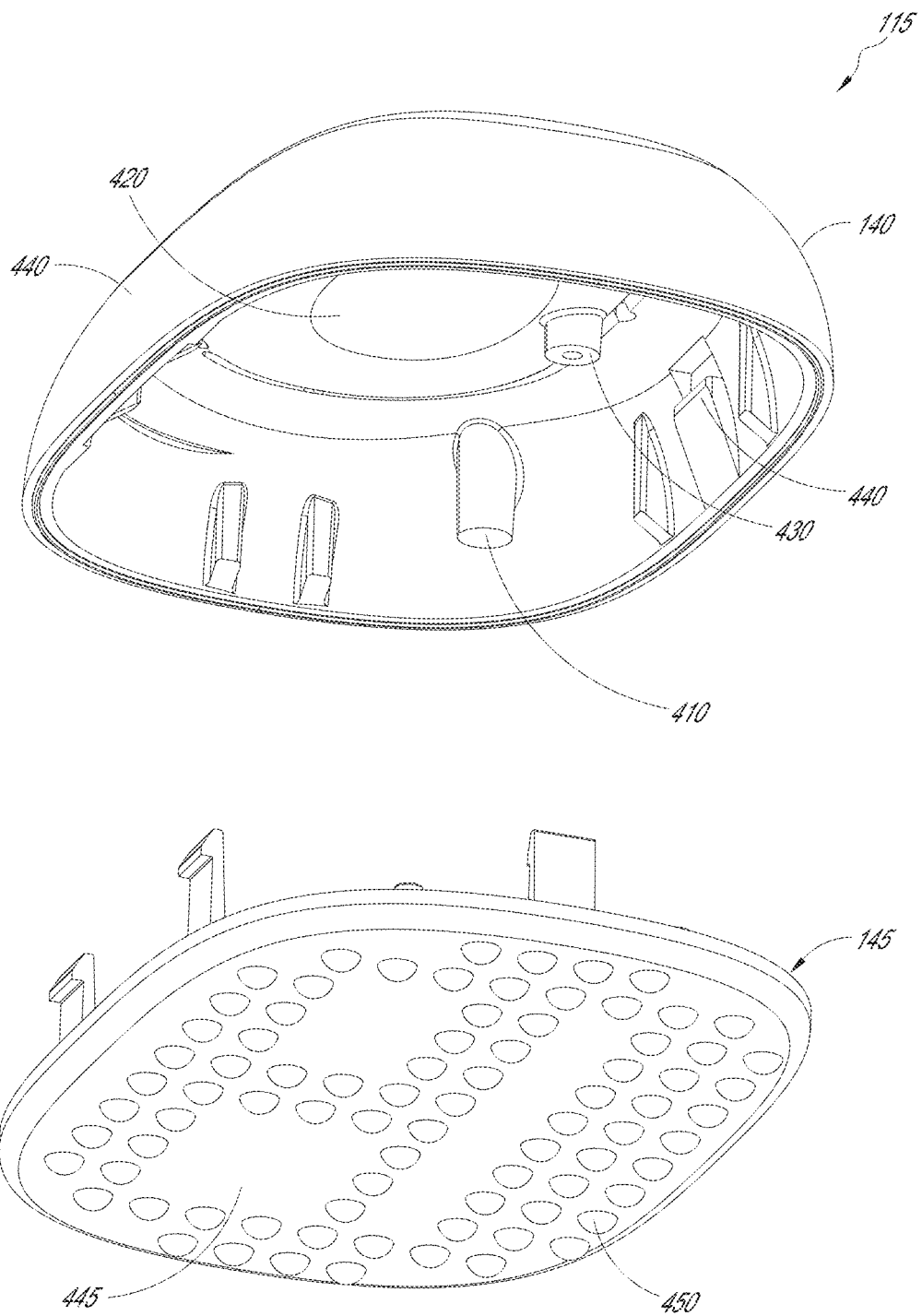
FIG. 4 is an exploded view of a rigid housing of the physiological monitoring device; according to one embodiment.

With reference now to the embodiment of FIG. 4, upper housing member 140 and lower housing member 145 of rigid housing 115 are shown in greater detail. Upper and lower housing members 140, 145 may be configured, when coupled together with gaskets 360, 370 in between, to form a watertight enclosure for containing PCBA 120, battery holder 150, batteries 160 and any other components contained within rigid housing 115. Housing members 140, 145 may be made of any suitable material to protect internal components, such as water resistant plastic. In one embodiment, upper housing member 140 may include a rigid sidewall 440, a light pipe 410 to transmit visual information from the LEDs on the PCBA through the housing member, a slightly flexible top surface 420, and an inner trigger member 430 extending inward from top surface 420. Top surface 420 is configured to be depressed by a patient when the patient perceives what he or she believes to be an arrhythmia or other cardiac event. When depressed, top surface 420 depresses inner trigger member 430, which contacts and activates trigger input 210 of PCBA 120. Additionally, as discussed previously, top surface 420 may have a concave shape (concavity facing the inside of housing 115) to accommodate the shape of a finger. It is believed that the design of upper housing member 140 isolates activation of the trigger input 210 from electrodes 350, thereby minimizing artifact in the data recording.

With continued reference to FIG. 4, lower housing member 145 may be configured to detachably connect with upper housing member 140 in such a way that housing members 140, 145 may be easily attached and detached for reusability of at least some of the component parts of monitoring device 100. In some embodiments, a bottom surface 445 (patient facing surface) of lower housing member 145 may include multiple dimples 450 (or "bumps," "protrusions" or the like), which will contact the patient's skin during use. Dimples 450 may allow for air flow between bottom surface 445 and the patient's skin, thus preventing a seal from forming between bottom surface 445 and the skin. It is believed that dimples 450 improve comfort and help prevent a perception in currently available devices in which the patient feels as if monitoring device 100 is falling off when it housing 115 lifts off the skin and breaks a seal with the skin. In yet another embodiment the bottom surface 445 of lower housing member 450 may include multiple divots (recesses instead of protrusions) to prevent a seal from forming.

Figure 5A:
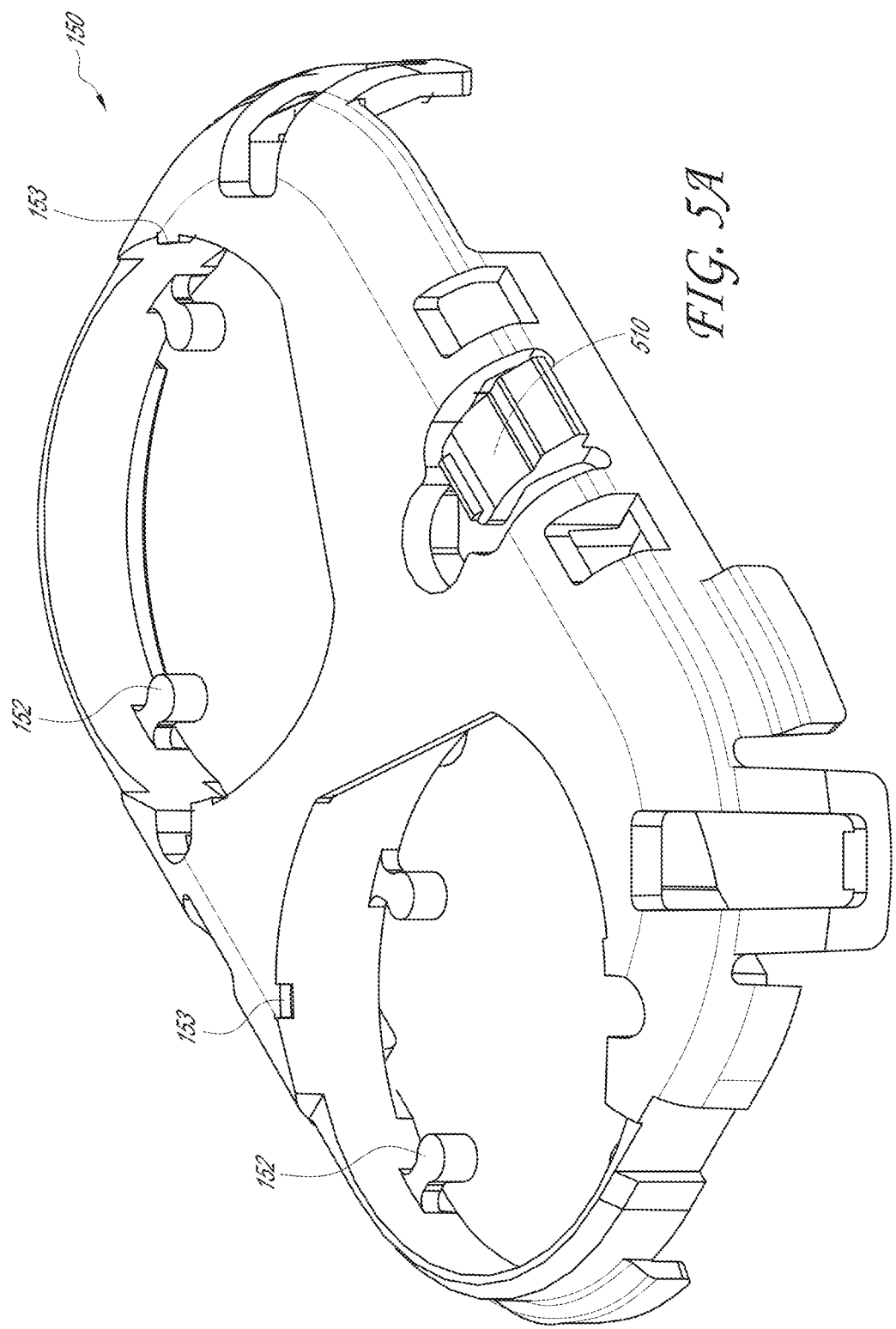
FIGS. 5A and 5B provide a perspective view of a battery holder of the physiological monitoring device, according to one embodiment.
Figure 5B:
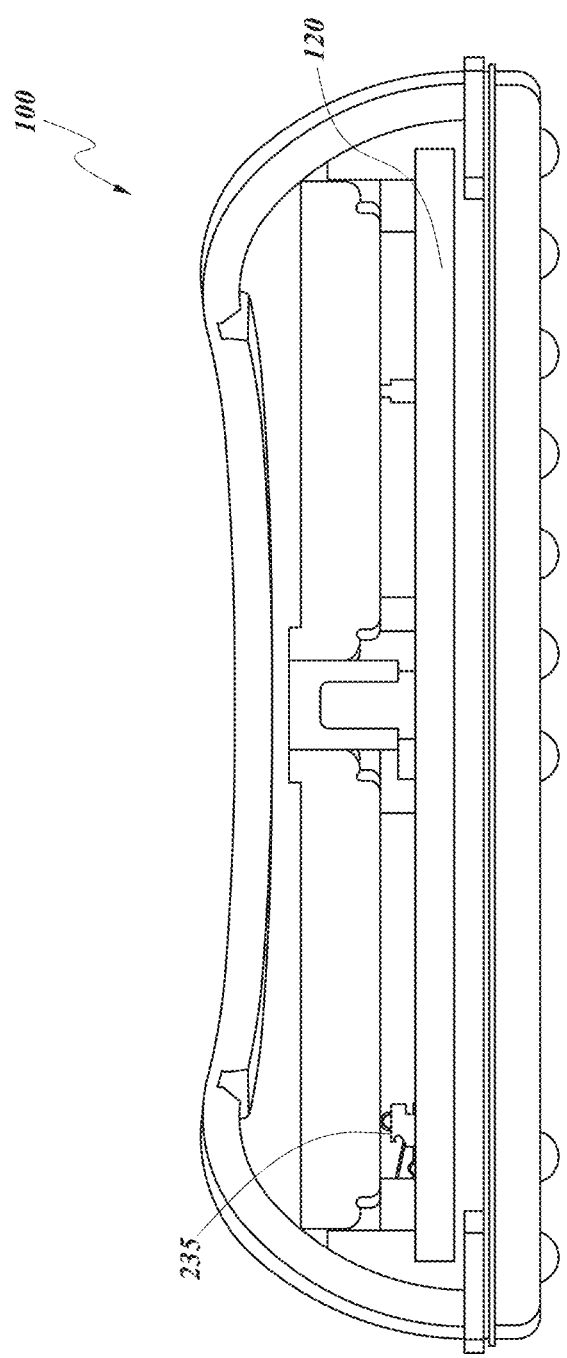

Referring now to the embodiment of FIG. 5A, battery holder 150 is shown in greater detail. Battery holder 150 may be made of plastic or other suitable material, is configured to be mounted to PCBA 120 and subsequently attached to rigid housing 115, and is capable of holding two batteries 160 (FIG. 1B). In alternative embodiments, battery holder 150 may be configured to hold one battery or more than two batteries. A plurality of protrusions 152 provide a stable platform for batteries 160 to be positioned a fixed distance above the surface of PCBA 120, avoiding unwanted contact with sensitive electronic components yet providing for adequate compression of spring contacts 235 (FIG. 5B). Protrusions 153 lock batteries 160 into position and resist the upward force on the batteries from spring contacts 235. Battery holder 150 also positions batteries appropriately 160 to provide for adequate compression of spring contacts 236. Use of battery holder 150 in conjunction with spring contacts 235 and 236 allows for batteries 160 to be electrically connected to PCBA 120 while still having additional electronic components between batteries 160 and PCBA 120 and maintain a very compact assembly. Battery holder 150 may include a flexible hook 510 which engages a corresponding rigid hook 440 of upper housing member 140. Under normal assembly conditions the flexible hook 510 remains securely mated with rigid hook 440. For disassembly, flexible hook 510 can be pushed and bent using an appropriate tool passed through top housing 140 causing it to disengage from rigid hook 440 and subsequently allow top housing 140 to be removed.

With reference now to the embodiments of FIGS. 6A and 6B, physiological monitoring device 100 is shown in side view cross-section. As shown in 6A, physiological monitoring device 100 may include flexible body 110 coupled with rigid housing 115. Flexible body 110 may include top substrate layer 300, bottom substrate layer 330, adhesive layer 340 and electrodes 350. Electrode traces 311, 312 are also typically part of flexible body 110 and are embedded between top substrate layer 300 and bottom substrate layer 330, but they are not shown in FIG. 6. Flexible body 110 forms two wings 130, 131, extending to either side of housing 115, and a border 133 surrounding at least part of each wing 130, 131. Rigid housing 115 may include an upper housing member 140 coupled with a lower housing member 145 such that it sandwiches a portion of flexible body 110 in between and provides a watertight, sealed compartment for PCBA 120. Upper housing member 140 may include inner trigger member 430, and PCBA may include patient trigger member 210. As discussed previously, lower housing member 145 may include multiple dimples 450 or divots to enhance the comfort of the monitoring device 100.

It is desirable that PCBA 120 is sufficiently rigid to prevent bending and introducing unwanted artifact into the signal. In certain embodiments, an additional mechanism to reduce and prevent unwanted bending of PCBA 120 may be used. This mechanism is shown in FIG. 6B. Support post 460 is integral to lower housing 145 and is positioned directly under patient trigger input 210. During patient symptom triggering, upper housing member 140 is depressed, engaging inner trigger mechanism 430 and transmitting a force through patient trigger input 210 into PCBA 120. The force is further transmitted through PCBA 120 and into support post 460 without creating a bending moment, thus avoiding unwanted artifact.

Figure 7:
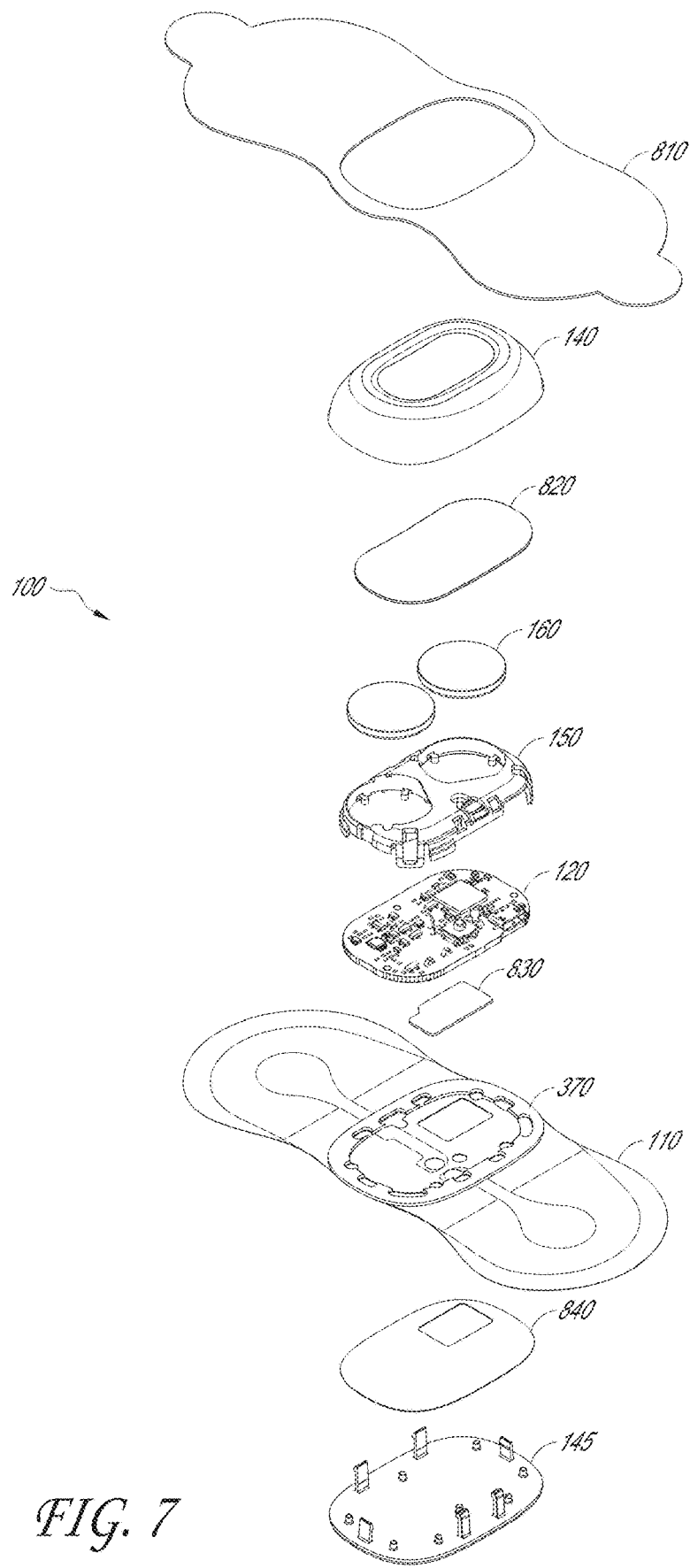
FIG. 7 is an exploded view of the physiological monitoring device including a number of optional items, according to one embodiment.

Referring to FIG. 7, in some embodiments, physiological monitoring device 100 may include one or more additional, optional features. For example, in one embodiment, monitoring device 100 may include a removable liner 810, a top label 820, a device identifier 830 and a bottom label 840. Liner 810 may be applied over a top surface of flexible member 110 to aid in the application of device 100 to the subject. As is described in further detail below, liner 810 may help support borders 133 of flexible body 110, as well as wings 130, 131, during removal of one or more adhesive covers (not shown) that cover adhesive surface 340 before use. Liner 810 may be relative rigid and/or firm, to help support flexible body 110 during removal of adhesive covers. In various embodiments, for example, liner 810 may be made of cardboard, thick paper, plastic or the like. Liner 810 typically includes an adhesive on one side for adhering to the top surface of wings 130, 131 of flexible body 110.

Labels 820, 840 may be any suitable labels and may include produce name(s), manufacturer name(s), logo(s), design(s) and/or the like. They may be removable or permanently attached upper housing member 140 and/or lower housing member 145, although typically they will be permanently attached, to avoid unregulated reuse and/or resale of the device by an unregistered user. Device identifier 830 may be a barcode sticker, computer readable chip, RFID, or the like. Device identifier 830 may be permanently or removably attached to PCBA 120, flexible body 110 or the like. In some embodiments, it may be beneficial to have device identifier 830 stay with PCBA 120.

Figure 8A:
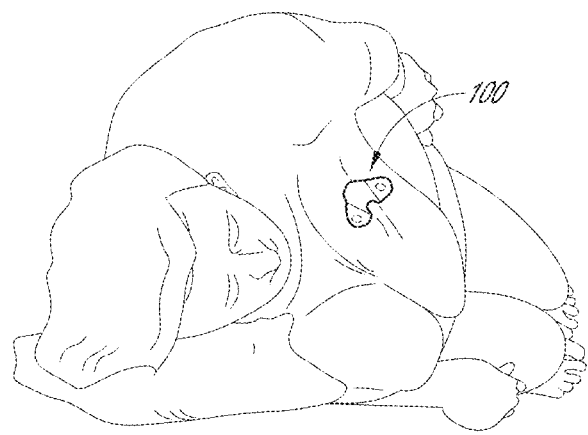
FIGS. 8A and 8B are perspective views of two people wearing the physiological monitoring device, illustrating how the device bends to conform to body movement and position, according to one embodiment.
Figure 8B:
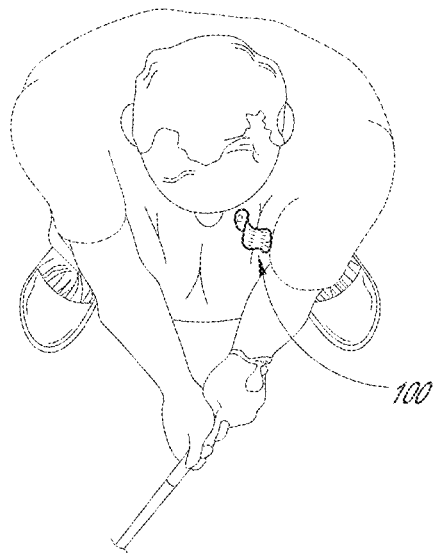

Referring now to the embodiments of FIGS. 8A and 8B, physiological monitoring device 100 generally includes hinge portions 132 at or near the juncture of each wing 130, 131 with rigid housing 115. Additionally, each wing 130, 131 is typically adhered to the patient via adhesive layers 340, while rigid body 115 is not adhered to the patient and is thus free to "float" (for example, move up and down) over the patient's skin during movement and change of patient position. In other words, when the patient's chest contracts, rigid housing pops up or floats over the skin, thus minimizing stress on device 100, enhancing comfort, and reducing the tendency of wings 130, 131 to peel off of the skin. The advantage provided by the combination of the floating rigid body 115 and the adhered wings 130, 131 is illustrated in FIGS. 8A and 8B. In FIG. 8A, a patient is sleeping, and in FIG. 8B, a patient is playing golf. In both examples, monitoring device 100 is squeezed together by the patient's body, causing rigid housing 115 to float above the skin as wings 130, 131 move closer together. This advantage of a floating, non-attached portion of a physiological monitoring device is described in further detail in U.S. Pat. No. 8,560,046, which was previously incorporated by reference.

Figure 9A:
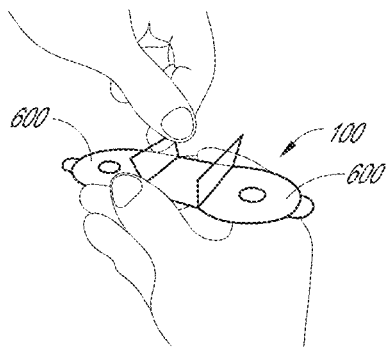
FIGS. 9A, 9B, 9C, 9D, 9E, and 9F illustrate various steps for applying the physiological monitor to a patient's body, according to one embodiment.
Figure 9B:
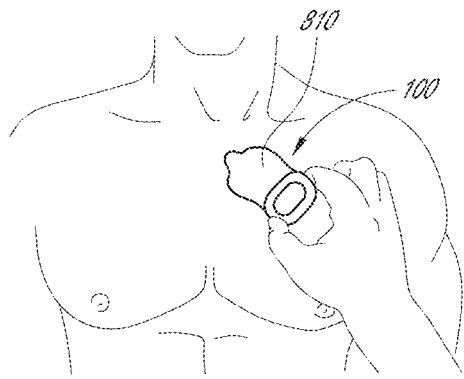
Figure 9C:
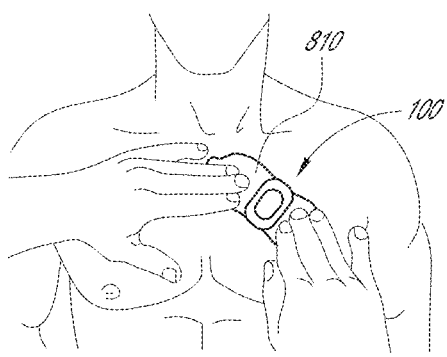

Referring now to FIGS. 9A-9F, one embodiment of a method for applying physiological monitoring device 100 to the skin of a human subject is described. In this embodiment, before the first step shown in FIG. 9A, the patient's skin may be prepared, typically by shaving a small portion of the skin on the left chest where device 100 will be placed and then abrading and/or cleaning the shaved portion. As shown in FIG. 9A, once the patient's skin is prepared, a first step of applying device 100 may include removing one or both of two adhesive covers 600 from adhesive layers 340 on the bottom surface of device 100, thus exposing adhesive layers 340. As illustrated in FIG. 9B, the next step may be to apply device 100 to the skin, such that adhesive layer 340 adheres to the skin in a desired location. In some embodiments, one adhesive cover 600 may be removed, the uncovered adhesive layer 340 may be applied to the skin, and then the second adhesive cover 600 may be removed, and the second adhesive layer 340 may be applied to the skin. Alternatively, both adhesive covers 600 may be removed before applying device 100 to the skin. While adhesive covers 600 are being removed, liner 810 acts as a support for flexible body 110, provides the physician or other user with something to hold onto, and prevents flexible body 110 and borders 133 of flexible body 110 from folding in on themselves, forming wrinkles, and so forth. As described above, liner 810 may be made of a relatively stiff, firm material to provide support for flexible body 110 during application of device 100 to the skin. Referring to FIG. 9C, after device 100 has been applied to the skin, pressure may be applied to flexible body 110 to press it down onto the chest to help ensure adherence of device 100 to the skin.

Figure 9D:
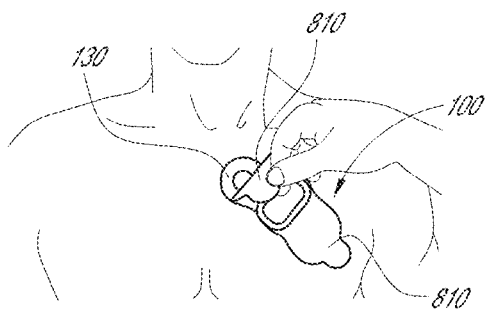
Figure 9E:
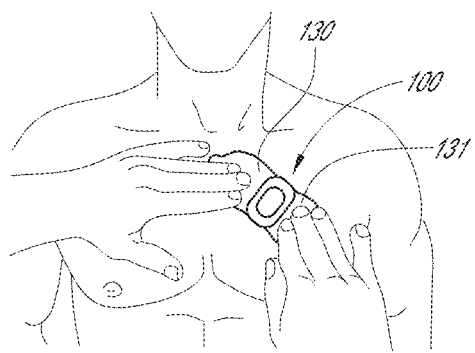
Figure 9F:
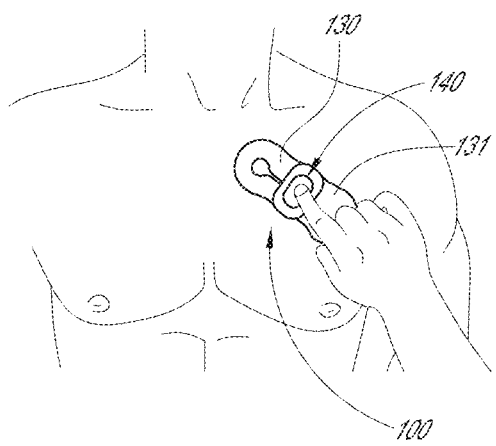

In a next step, referring to FIG. 9D, liner 810 is removed from (for example, peeled off of) the top surface of flexible body 110. As shown in FIG. 9E, once liner 810 is removed, pressure may again be applied to flexible body 110 to help ensure it is adhered to the skin. Finally, as shown in FIG. 9F, upper housing member 140 may be pressed to turn on physiological monitoring device 140. This described method is only one embodiment. In alternative embodiments, one or more steps may be skipped and/or one or more additional steps may be added.

In certain embodiments, when a desired monitoring period has ended, such as about 14 to 21 days in some cases, a patient (or physician, nurse or the like) may remove physiological monitoring device 100 from the patient's skin, place device 100 in a prepaid mailing pouch, and mail device 100 to a data processing facility. At this facility, device 100 may be partially or completely disassembled, PCBA 120 may be removed, and stored physiological data, such as continuous heart rhythm information, may be downloaded from device 100. The data may then be analyzed by any suitable method and then provided to a physician in the form of a report. The physician may then discuss the report with the patient. PCBA 120 and/or other portions of device 100, such as rigid housing 115, may be reused in the manufacture of subsequent devices for the same or other patients. Because device 100 is built up as a combination of several removably coupled parts, various parts may be reused for the same embodiment or different embodiments of device 100. For example, PCBA 120 may be used first in an adult cardiac rhythm monitor and then may be used a second time to construct a monitor for sleep apnea. The same PCBA 120 may additionally or alternatively be used with a differently sized flexible body 110 to construct a pediatric cardiac monitor. Thus, at least some of the component parts of device 100 may be interchangeable and reusable.

In further embodiments described in greater detail below, the monitoring data may be transmitted wirelessly or through other communication mediums to be analyzed, rather than requiring physical shipment of the device for analysis and reporting.

Advantageously, physiological monitoring device 100 may provide long term adhesion to the skin. The combination of the configuration of flexible and conformal body 110, the watertight, low profile configuration of rigid housing 115, and the interface between the two allows device 100 to compensate for stress caused as the skin of the subject stretches and bends. As a result, device 100 may be worn continuously, without removal, on a patient for as many as 14 to 21 days or more. In some cases, device 100 may be worn for greater or less time, but 14 to 21 days may often be a desirable amount of time for collecting heart rhythm data and/or other physiological signal data from a patient.

In various alternative embodiments, the shape of a particular physiological monitoring device may vary. The shape, footprint, perimeter or boundary of the device may be circular, an oval, triangular, a compound curve or the like, for example. In some embodiments, the compound curve may include one or more concave curves and one or more convex curves. The convex shapes may be separated by a concave portion. The concave portion may be between the convex portion on the rigid housing and the convex portion on the electrodes. In some embodiments, the concave portion may correspond at least partially with a hinge, hinge region or area of reduced thickness between the body and a wing.

While described in the context of a heart monitor, the device improvements described herein are not so limited. The improvements described in this application may be applied to any of a wide variety of physiological data monitoring, recording and/or transmitting devices. The improved adhesion design features may also be applied to devices useful in the electronically controlled and/or time released delivery of pharmacological agents or blood testing, such as glucose monitors or other blood testing devices. As such, the description, characteristics and functionality of the components described herein may be modified as needed to include the specific components of a particular application such as electronics, antenna, power supplies or charging connections, data ports or connections for down loading or off-loading information from the device, adding or offloading fluids from the device, monitoring or sensing elements such as electrodes, probes or sensors or any other component or components needed in the device specific function. In addition or alternatively, devices described herein may be used to detect, record, or transmit signals or information related to signals generated by a body including but not limited to one or more of ECG, EEG and/or EMG. In certain embodiments, additional data channels can be include to collect additional data, for example, device motion, device flex or bed, heart rate and/or ambient electrical or acoustic noise.

The physiological monitors described above and elsewhere in the specification may further be combined with methods and systems of data processing and transmission that improve the collection of data from the monitor. Further, the methods and systems described below may improve the performance of the monitors by enabling timely transmission of clinical information while maintaining the high patient compliance and ease-of-use of the monitor described above. For example, the methods and systems of data processing and transmission described herein this section of elsewhere in the specification may serve to extend the battery life of the monitor, improve the accuracy of the monitor, and/or provide other improvements and advantages as described herein this section or elsewhere in the specification.

Device Monitoring and Clinical Analysis Platform

The systems and methods described in detail below, in reference to the embodiments of FIGS. 10 to 17, may selectively extract, transmit, and analyze electrocardiographic signal data and other physiological data from a wearable physiological monitor, such as is described above in relation to FIGS. 1 through 9. The systems and methods described below can improve the performance of a wearable physiological monitor that simultaneously records and transmits data through multiple means. For example, selective transmission of extracted data allows for decreased power consumption because the wearable patch is not required to transmit all recorded data. By sending extracted data, much of the analysis may be performed away from the wearable device without requiring full on-board rhythm analysis, which can also be highly power consumptive, reducing battery life. Further, remote analysis without the power constraints inherent to a wearable device may allow for greater sensitivity and accuracy in analysis of the data. Decreased power consumption serves to improve patient compliance because it prolongs the time period between or even eliminates the need for device replacement, battery changes or battery recharging during the monitoring cycle. By decreasing battery consumption, longer monitoring times may be enabled without device replacement, for example, at least one week, at least two weeks, at least three weeks, or more than three weeks.

Figure 10:
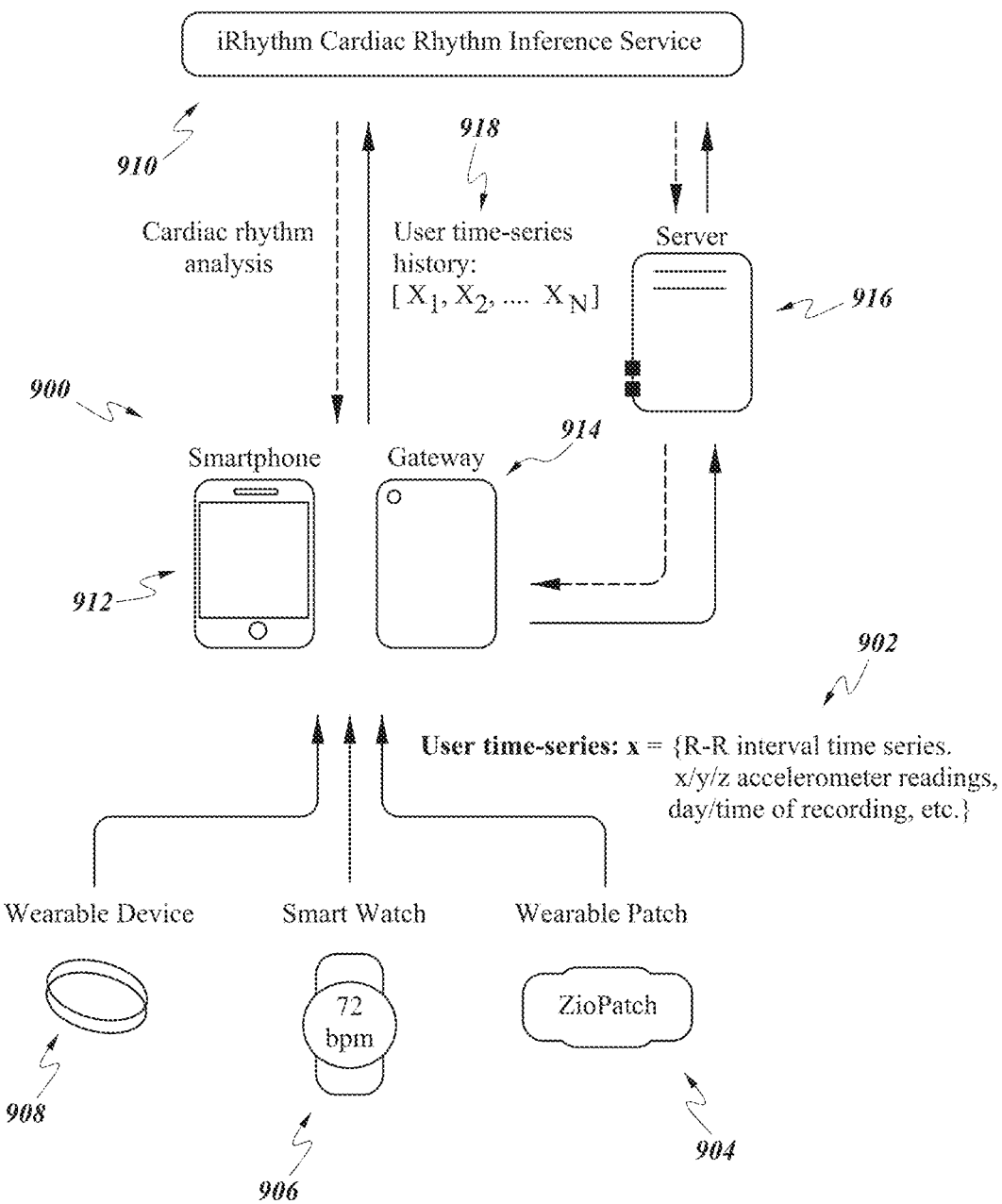
FIG. 10 illustrates a schematic diagram of an embodiment of a cardiac rhythm inference service.

FIG. 10 depicts a general overview of an embodiment of a system 900 for inferring cardiac rhythm information from an R-R interval time series 902, as may be generated by a continuous heart rate monitoring device 904. Such systems will be described in much greater detail below in relation to FIGS. 11 to 17. The R-R interval time series 902 inputted to the system may include a series of measurements of the timing interval between successive heartbeats. Typically each interval represents the time period between two successive R peaks as identified from an ECG signal. R peaks are part of the QRS complex, a combination of three graphical deflections typically seen on an ECG, representing the depolarization of the left and right ventricles of a mammal's heart. The R peak is generally the tallest and most visible upward deflection on an ECG, and thus makes for an appropriate reference point. However, in further embodiments, any characteristic ECG fiducial point (such as the QRS complex onset or offset) may be used in place of the R peak to provide an estimate of the R-R interval time series. As described above in relation to FIGS. 1 through 9, the physical characteristics of the monitoring device are constructed in such a way as to improve signal fidelity, therefore the high signal fidelity allows for a high level of confidence in accurately extracting R-R peak data.

The R-R interval time series 902 data may be extracted from or received from a dedicated heart rate monitor such as a heart rate chest strap or heart rate watch, or a wearable health or fitness device 906, 908 that incorporates heart rate sensing functionality. Alternatively, the R-R interval time series 902 may be derived from a wearable patch designed to measure an ECG signal 904 (for instance, by locating the R peaks in the ECG using a QRS detection algorithm). Furthermore, the R-R interval time series 902 may be estimated from an alternative physiological signal such as that obtained from photoplethysmography (PPG). In this scenario, the peak-to-peak interval time series determined from the PPG signal may be used as an accurate estimate of the R-R interval time series.

In one aspect, a cardiac rhythm inference system 910 is implemented as a cloud service or server-based system that exposes an application programming interface (API) enabling R-R interval time series data or other signal data to be transmitted to the system (for instance, via HTTP) and the resulting cardiac rhythm information to be returned to the calling software. The R-R interval time series data 902 or other signal data may be transmitted to the cloud service directly from the heart-rate monitoring device itself, or indirectly via a smartphone 912, tablet or other internet-enabled communication device 914 that can receive data from the heart rate monitoring device in either a wireless or wired manner. In addition, the R-R interval time series data 902 or other signals may be transmitted from a server 916 that stores the data for a number of users.

In some embodiments, a cardiac rhythm inference system 910 is provided through a software library that can be incorporated into a standalone application for installation and use on a smartphone, tablet or personal computer. The library may provide identical functionality to that of the inference service, but with R-R interval time series data 902 or other signal data transmitted directly through a functional call, as opposed to through a web service API.

In certain embodiments, a cardiac rhythm inference system may accept a plurality of R-R interval time series measured from devices of a given user 918, in addition to an individual R-R interval time series 902. In this scenario, the system computes the frequency and duration of each of the cardiac rhythm types inferred from the collection of time series data. These results may then be used to estimate confidence statistics for each type of cardiac rhythm based on the frequency and duration of occurrence of that rhythm across the various time series. In addition, the rhythm confidence statistics may be updated in a sequential manner for each separate call of the inference service. Furthermore, in some embodiments, the cardiac rhythm information inferred by the system may be provided back to the calling software only in the event that the confidence score for a given rhythm type exceeds a pre-determined threshold value.

In particular embodiments, a cardiac rhythm inference system 910 may accept additional sources of data, generally described as alternate sensor channels, in addition to R-R interval time series data, to enhance the accuracy and/or value of the inferred results. One additional source of data includes user activity time series data, such as that measured by a 3-axis accelerometer concurrently with the R-R interval time series measurements. In addition, the system may accept other relevant metadata that may help to improve the accuracy of the rhythm analysis, such as user age, gender, indication for monitoring, pre-existing medical conditions, medication information, medical history and the like, and also information on the specific day and time range for each time series submitted to the system. Furthermore, the measurement device might also provide some measure of beat detection confidence, for example, for each R-Peak or for sequential time periods. This confidence measure would be based on analysis the recorded signal that, in typical embodiments, would not be recorded due to storage space and battery energy requirements. Finally, in the particular case that the R-R interval time series data are derived from an ECG signal, the system may accept additional signal features computed from the ECG. These features may include a time series of intra-beat interval measurements (such as the QT or PR interval, or QRS duration), or a time series of signal statistics such as the mean, median, standard deviation or sum of the ECG signal sample values within a given time period.

The various aspects described above could be used either individually or in combination to provide an application providing insights into an individual's health, stress, sleep, fitness and/or other qualities.

Some embodiments concern a system for selective transmission of electrocardiographic signal data from a wearable medical sensor. Current wearable sensors, such as the iRhythm ZioPatch™ 904, and further described above in relation to FIGS. 1-9, are capable of recording a single-lead electrocardiogram (ECG) signal for up to two weeks on a single battery charge. In many situations however, it is desirable for the sensor to be able to transmit, in real-time or near real-time, specific sections of the recorded ECG signal with clinical relevance to a computer device, such as either a smartphone 912 or an internet-connected gateway device 914 for subsequent processing and analysis. In this way, the patient or their physician can be provided with potentially valuable diagnostic ECG information during the period that the patient wears the sensor.

As described above, a significant challenge with this approach is to manage the battery life of the wearable sensor without requiring replacement or recharging, both of which reduce user compliance. Each transmission of an ECG from the sensor to a smartphone or local gateway device (using, for example, Bluetooth Low Energy) results in a subsequent reduction in the total charge stored in the sensor battery. Some embodiments of the present disclosure, particularly those of FIGS. 10 to 17 address this issue through the use of a novel hardware and software combination to enable the selective transmission of clinically relevant sections of ECG from a wearable sensor.

In certain embodiments, the wearable sensor incorporates either a software, hardware or hybrid QRS detector that produces a real-time estimate of each R-peak location in the ECG. The R-peak location data is then used to compute an R-R interval time series that is subsequently transmitted to a smartphone or gateway device according to a predefined schedule (for example, once per hour). In addition, a time stamp is also transmitted which stores the onset time for the R-R interval time series relative to the start of the ECG recording. Since the R-R interval time series for a given section of ECG is significantly smaller (in terms of bytes occupied) than the ECG signal itself, it can be transmitted with considerably less impact on battery life.

In some embodiments of a second stage of the system, the R-R interval time series together with the onset time stamp is subsequently transmitted by the smartphone or gateway device to a server. On the server, the R-R interval time series is used to infer a list of the most probable heart rhythms, together with their onset and offset times, during the period represented by the time series data. The list of inferred heart rhythms is then filtered according to specific criteria, such that only rhythms matching the given criteria are retained after filtering. A measure of confidence may also be used to assist in filtering the events in a manner that might improve the Positive Predictivity of detection.

In certain embodiments of a third stage of the system, for each rhythm in the filtered rhythm set, the server transmits to the smartphone or gateway device the onset and offset time for that specific rhythm. In the event that the inferred rhythm duration exceeds a pre-defined maximum duration, the onset and offset times may be adjusted such that the resulting duration is less than the maximum permissible duration. The onset and offset times received by the gateway are then subsequently transmitted to the wearable sensor, which in turn transmits the section of the recorded ECG signal between the onset and offset times back to the gateway. This section of ECG is then transmitted to the server where it can be analyzed and used to provide diagnostic information to the patient or their physician.

In some embodiments, the system fundamentally allows a device worn for up to about: 14, 21, or 30 days or beyond without battery recharging or replacement (both activities that reduce patient compliance and, therefore, diagnostic value) to provide timely communication of asymptomatic arrhythmia events. This development is motivated by technology constraints: in order to enable a small, wearable device that does not require battery change or recharging while providing continuous arrhythmia analysis with high accuracy, it is desirable to limit the complexity of analysis performed on-board. Similarly, streaming of all of the recorded ECG data to an off-board analysis algorithm may not be practical without imposing greater power requirements. This motivates a more creative "triage" approach where selected features of the recorded ECG signal, including but not limited to R-R intervals, are sent for every beat, allowing a customized algorithm to locate a number (for example, 10) of 90-second events to request from the device in full resolution to support comprehensive analysis, for example, a resolution capable of supporting clinical diagnosis.

In other embodiments, the system would provide the ability to detect asymptomatic arrhythmias in a timely manner on a wearable, adhesively affixed device that does not require frequent recharging or replacement. This would be used to enhance the value of some current clinical offerings, which only provide clinical insight after the recording is completed and returned for analysis.

In certain embodiments, the system would allow actionable clinical insight to be derived from data collected on low-cost, easy-to-use consumer wearable devices that are otherwise only focused on fitness and wellness. For example, the technology could be used to create a very effective, low-cost screening tool capable of detecting the presence of Atrial Fibrillation in the at-large population. By using such a tool, not only would patients in need of care be found more easily, but it may be done earlier and more cost effectively, which lead to better outcomes—namely, through reducing stroke risk by identifying AF more quickly.

In particular embodiments, the system may provide the service through a downloadable application that, after receiving customer consent for data access and payment approval, would initiate access and analysis of heart beat data stored from wearable devices, either stored locally in a mobile device or in an online repository. This data pull and analysis would happen through an Algorithm API, and would result in a clinical finding being sent back to the application to be provided to the user. If the data was sufficient to support a "screening oriented" finding, for example, "Likely presence of an irregular rhythm was detected", the application would direct them to a cardiologist where a more diagnostically focused offering, for example, the ZIO® Service, could be provided to support clinical diagnosis and treatment. In further embodiments, as also described elsewhere in the specification, the system may trigger an alarm if a particular measurement and/or analysis indicates that an alarm is needed.

Further examples of additional scenarios of clinical value may include coupling ambulatory arrhythmia monitoring with a blood-alcohol monitor to study the interaction of AF and lifestyle factors. For example, ambulatory arrhythmia monitoring could be coupled with a blood-glucose monitor to study the impact of Hypoglycemia on arrhythmias. Alternatively, ambulatory arrhythmia monitoring could be coupled with a respiratory rate and/or volume monitor to study the interaction of sleep apnea and breathing disorders. Further, there could be evaluation of the high rates of supraventricular ectopic beats as a potential precursor for AF (for example, 720 SVEs in 24-hour period).

Extraction, Transmission, and Processing Systems

Figure 11:
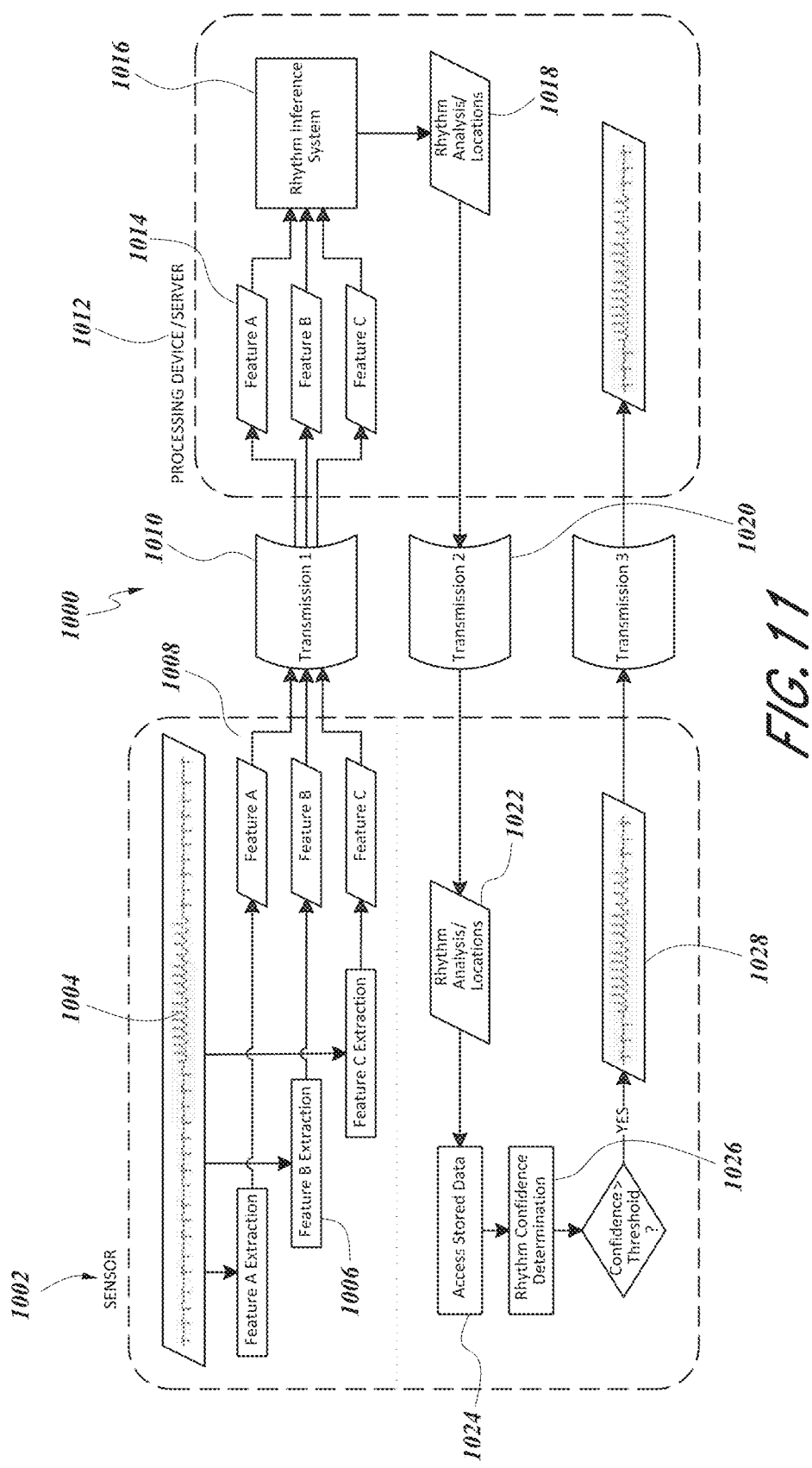
FIG. 11 is a schematic diagram of an embodiment of a system for extracting and transmitting data features from a physiological monitor.

FIG. 11 is a schematic illustration of an embodiment of a system and method 1000 for a wearable medical sensor 1002 with transmission capabilities, similar to the system and/or method described above in relation to FIG. 10. In some embodiments, sensor 1002, which may be any type of sensor or monitor described herein this section or elsewhere in the specification, continuously senses an ECG or comparable biological signal 1004 and continuously records an ECG or comparable biological signal 1004. In certain embodiments, the sensing and/or recording steps may be performed intermittently. The collected signal 1004 may then be continuously extracted into one or more features 1006, representing example features A, B, and C. The features are not intended to be samplings of different temporal sections of the signal, instead (as will be described in greater detail below) the different features may correspond to different types or pieces of data such as R-peak locations or R-peak amplitudes. The features of the ECG or comparable biological signal are extracted to facilitate analysis of the signal 1004 remotely. In certain embodiments, features are extracted on a windowed basis, with the window size varying for example between 1 hour or multiple hours to a few seconds. In certain embodiments, the window may be at most: about 0.1 second, about 1 second, about 2 seconds, about 3 seconds, about 5 seconds, about 10 seconds, about 30 seconds, about 1 minute, about 5 minutes, about 30 minutes, about 1 hour, about 2 hours, about 4 hours, or more than 4 hours. The extraction windows may be separated by various amounts of time if they are repeated. For example, the extraction windows may be separated by at least: about 30 seconds, about 1 minute, about 5 minutes, about 30 minutes, about 1 hour, about 3 hours, about 6 hours, about 12 hours, about 24 hours, about 48 hours, or more than three days. In certain embodiments, the windowing sizes may vary depending on the feature extracted. Feature extraction may be limited to one type or various types of features, and features chosen for extraction may vary depending on the nature of the signal observed.

A wide variety of different types of ECG or comparable biological signal features may be extracted. For example, R-peak locations may be extracted. In certain embodiments, the R-peak locations are extracted via various methods such as: a Pan-Tompkins algorithm (Pan and Tompkins, 1985), providing a real-time QRS complex detection algorithm employing a series of digital filtering steps and adaptive thresholding, or an analog R-peak detection circuit comprising an R-peak detector consisting of a bandpass filter, a comparator circuit, and dynamic gain adjustment to locate R-peaks. The RR-intervals may be calculated from peak locations and used as the primary feature for rhythm discrimination. In embodiments, an R-peak overflow flag may be extracted. If more than a certain number of R-peaks were detected during a given time window such that not all data can be transmitted, a flag may be raised by the firmware. Such an extraction may be used to eliminate noisy segments from analysis, on the basis that extremely short intervals of R-R are not physiologically possible. With similar motivation, an R-peak underflow flag may be extracted to indicate an unrealistically long interval between successive R peaks, provided appropriate considerations for asystole are made in this evaluation. In an alternative implementation with the same goal, the lack of presence of R peaks in a prolonged interval could be associated with a confidence measure, which would describe the likelihood that the interval was clinical or artifact.

Another example of a feature that may be extracted 1006 includes a saturation flag, a firmware or hardware-determined indication that the signal saturated during a given time window (for example 1 second). Such an extraction may be used to eliminate noisy segments from analysis. In certain embodiments, P/T-wave locations may be extracted. This is similar to R-peak detection, but tuned to lower frequency waves. R-peak locations may be used to determine the areas of possible wave components. Still another example of a feature that may be extracted includes the breathing rate. ECG-derived respiration (EDR) may be derived from studying the amplitude modulation of ECG signal amplitude. EDR may be associated with other clinical indicators of arrhythmia. In embodiments, R-peak amplitude may be extracted, by measuring the ECG signal amplitude at R-peak locations. This pattern may be studied to discriminate between true and false peak detection, and/or to detect changes in beat morphology.

In particular embodiments, the ECG signal amplitude proxy may be extracted. This feature may include: the range of the raw signal data during a given time period, the maximum value of the signal during a given time period, or the minimum value of the signal during a given time period. This feature may be used as a data point for noise detection or possible changes in morphology of the ECG (for example ventricular ectopy). In some embodiments, additional ECG signal samples may be extracted. Sampling a few data points at regular intervals or consecutively from a region in-between selected R-peaks will allow for determination of the confidence of rhythm and/or noise classification. Such a selection may be based on R-R interval length. For instance, if the interval is longer than 3 seconds, it may be an indicator of a pause. Local ECG signal energy may also be extracted, for example by taking the sum square of signal values within a window centered on a point of interest, for example an R-peak, thereby providing an integral of ECG sample values in a given time window. This information may be used to characterize the morphology of beats (supraventricular tachycardia (SVT) vs. ventricular tachycardia (VT)).

In certain embodiments, spectral information may be extracted via extracting statistics from the output from one or more filters, either realized on hardware (during signal acquisition) or firmware. Filters may be implemented as a filter bank, such as a short-time Fourier transform (STFT) or wavelet transform. Such information may be used to characterize the morphology of heart beats. Output from simple machine-learned models may be extracted. For example, the likelihood of a selected ECG signal segment under a probability model, for example Gaussian, given raw collected data values or any combination of features derived from available channels of data may be extracted. The use of a simple machine-learned model may allow transmission of less data. In embodiments, the output can directly or indirectly give insight into: the type of underlying rhythm, the presence of ECG features such as a P-wave, the confidence level of R-peak detection, and the presence of noise.

Once the feature extraction as described above is completed, various features 1008 may then be transmitted 1010 to a processing device/server 1012. The features 1008 (and alternate sensor channel data and/or features as described below) are transmitted 1010 at regular intervals to a processor 1012 that is not a physical part of the sensor 1002. The interval definition may be pre-set or, configurable with each use, or dynamically configurable. Transmission 1010 of features 1008 may also be bundled and sent when another reason for communication exists, such as transmission of symptomatic data (described in greater detail below in relation to FIG. 16). In certain embodiments, the processing device 1012 may be: a cloud-based server, a physical server at a company location, a physical server at patient or clinic location, a smartphone, tablet, personal computer, smartwatch, automobile console, audio device and/or an alternate device on or off-site. In particular embodiments, the transmission 1010 may utilize short-range RF communication protocols, such as: Bluetooth, ZigBee, WiFi (802.11), Wireless USB, ANT or ANT+, Ultrawideband (UWB), and/or custom protocols. The transmission 1010 may be via infrared communication, such as IrDA and/or inductive coupling communication, such as NFC. In certain embodiments, transmission may be accomplished via cellular data networks and/or wired communication protocols, such as: USB, Serial, TDMA, or other suitable custom means.

In some embodiments, the transmitted features 1014 are processed by the remote processor utilizing the data features 1014 to perform analysis via a rhythm inference system 1016 that analyzes and identifies segments/locations 1018 likely to include arrhythmia. For example, arrhythmia and ectopy types that may be identified could include: Pause, $2^{nd}$ or $3^{rd}$ degree AVB, Complete Heart Block, SVT, AF, VT, VF, Bigeminy, Trigeminy, and/or Ectopy. Confidence of determination may be included in the identification of rhythms. Further, the rhythm inference system 1016 may also utilize patient demographic data, such as age, gender, or indication to improve accuracy and/or refine confidence in determinations.

The identified arrhythmia locations 1018 are then transmitted 1020 back to the sensor 1002. The transmission 1020 back to the sensor may be accomplished by any communication protocols/technology described herein this section or elsewhere in the specification, for example via Bluetooth. The sensor then reads the transmitted identified locations 1022 and accesses 1024 the areas of memory corresponding to the transmitted identified locations 1022 of the ECG. In some embodiments, the sensor applies additional analysis of the identified segments to further build confidence in the arrhythmia identification. This further rhythm confidence determination step 1026 allows for increasing positive predictivity prior to the power-hungry transmission step. In embodiments, if the confidence exceeds a defined threshold the data segment is transmitted. For example, the defined threshold may be a preset value or it may be set per user and monitoring session. In embodiments, the defined threshold may be changed dynamically depending on the nature of the rhythm, the history of accurate detection within the monitoring period, and/or the confidence of the rhythm inference system. Additional analysis may also be performed. Examples of possible analysis techniques include any methods disclosed herein this section or elsewhere in the specification, for example: R-peak amplitude, ECG signal amplitude proxy, ECG signal samples, local ECG signal energy, spectral information, and/or output from a simple machine-learned model.

If the confidence exceeds a threshold as described above, the sensor 1002 may transmit the requested ECG segments 1028 to the processing device via any transmission means described herein this section or elsewhere in the specification. The processing device may complete further analysis on the segments to confirm accuracy of predicted arrhythmia before using data to report to a user and/or physician, as needed.

Figure 12:
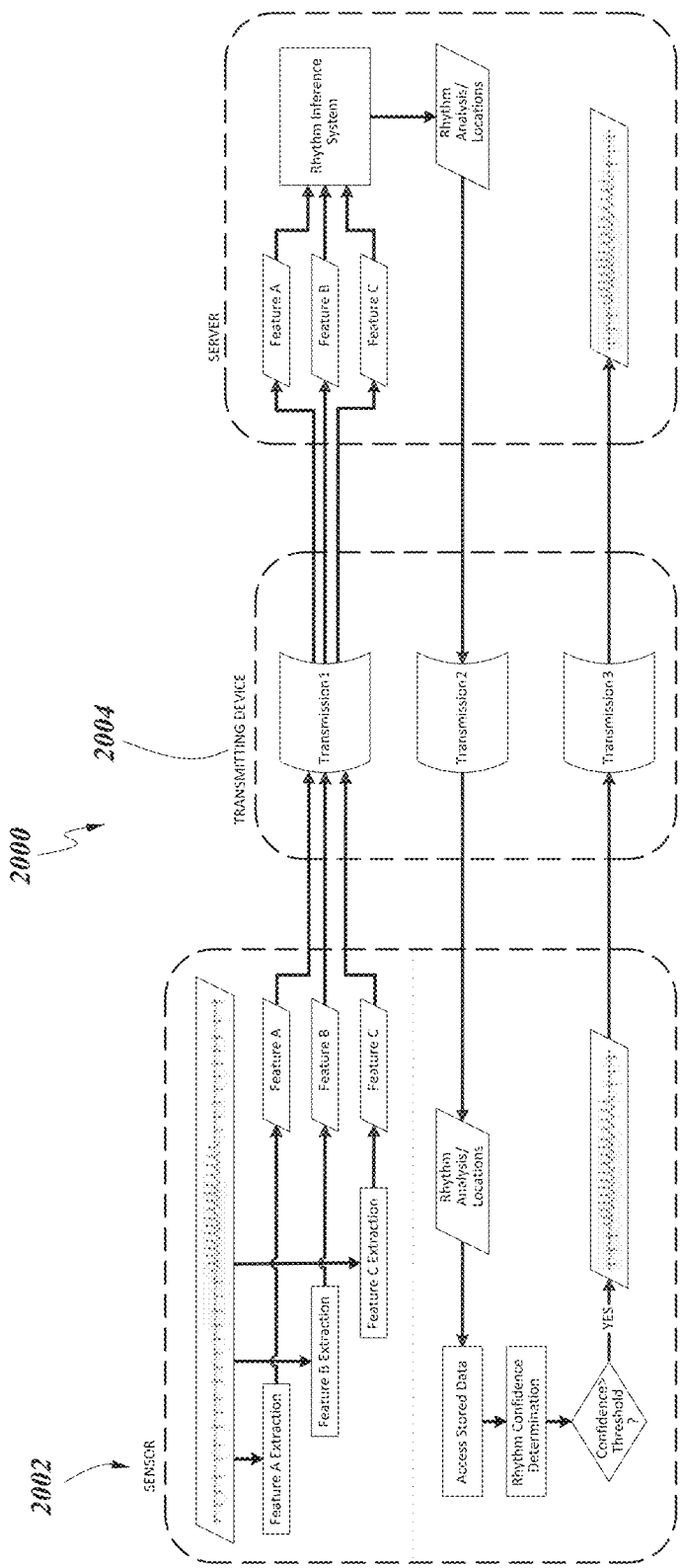
FIG. 12 is a schematic diagram of an embodiment of a system for extracting and transmitting data features from a physiological monitor using a transmitting device.

FIG. 12 is a schematic illustration of an embodiment of a system and method 2000 for a wearable ECG and/or medical sensor 2002 with transmission capabilities very similar to the system and/or method 1000 described above in relation to FIG. 11. The system of FIG. 12 differs from the system of FIG. 11 in that it includes secondary transmitting devices 2004. For example, possible secondary transmitting devices include: smartphones, tablets, personal computers, dedicated custom gateways, audio devices, wearable activity monitors, automobile consoles, other devices described herein this section or elsewhere in the specification, and other available devices for passing data.

Figure 13:
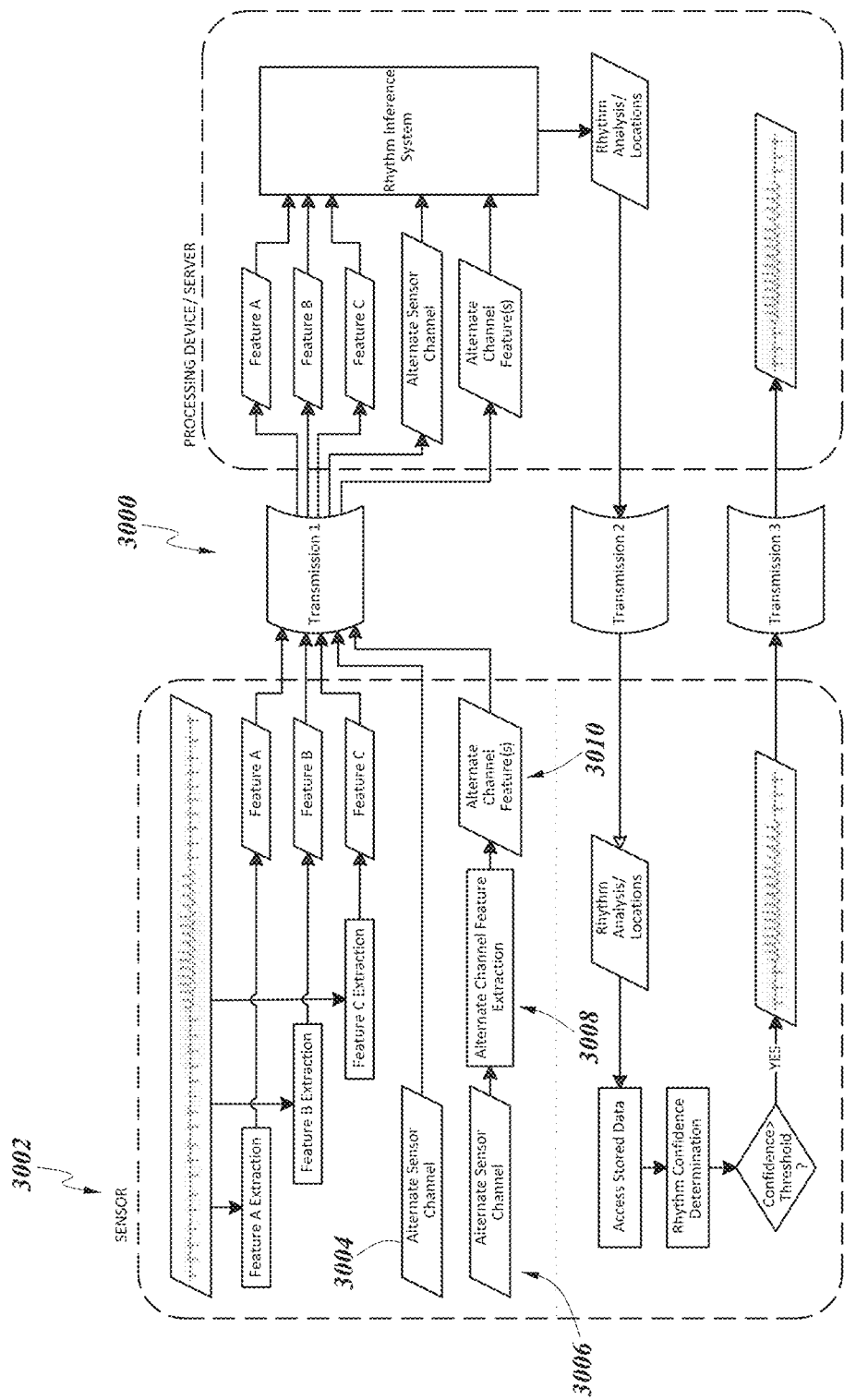
FIG. 13 is a schematic diagram of an embodiment of a physiological monitoring system utilizing additional data channels.

FIG. 13 is a schematic illustration of an embodiment of a system and method 3000 for a wearable ECG and/or medical sensor 3002 with transmission capabilities, very similar to the system and/or methods described above in relation to FIGS. 11 and 12. FIG. 13 differs from FIGS. 11 and 12 in that FIG. 13 illustrates alternate sensor channels 3004, 3006 producing alternate outputs and/or extraction 3008 of features 3010. Collection of other channels of data may serve to further augment ECG-extracted features. Data from the alternate sensor channels may be sent whole or specific features 3010 of the data channel may be extracted 3008. In certain embodiments, an alternate data channel may record galvanic skin response/impedance. This data may indicate whether the sensor 3002 leads are on or off, for example, via a Boolean algorithm indicating whether the leads are in an on/off state during a given time period, based on a preset threshold and built-in hysteresis. This information could be further used to remove periods of non-contact of the device with the body from analysis. In certain embodiments, in addition to the on/off indication Boolean, the collection of more granular impedance data points may provide insight into the change in patient activity levels, due to changes in sweat levels. In embodiments, an alternative sensor data channel may be from an accelerometer. Such a device may provide free-fall detection via an on-board algorithm to detect free-fall, an indication that the patient may have suddenly fallen due to arrhythmia-induced syncope. Further, the magnitude of acceleration detected by the accelerometer may be used to detect periods of sleep, activity levels, types of activity, and/or possibility of motion artifact, all of which may correlate with the prevalence of certain rhythm types. In particular embodiments, raw accelerometer values may be used to determine body orientation given a reference point (for example, whether the patient was upright when they were first patched). Additionally, change in orientation of the accelerometer may be used to distinguish clinically relevant morphology changes vs. not clinically relevant changes, in addition to providing more insight into activity type.

In some embodiments, an alternative data channel may be provided by a pulse oximeter. For example, a photoplethysmogram (PPG) may be generated by the pulse oximeter. The PPG may provide an alternative source for R-peak locations or as a cross-check on R-peak detection by the ECG circuitry. Further, the PPG data channel may be combined with multiple PPG/BioZ channels to output confidence of R-peak detection confidence levels. In further embodiments, SpO2/ perfusion via the pulse oximeter may provide further clinical indications of a severe arrhythmia. In certain embodiments, an alternative sensor channel may involve bioimpedance, which may be used to determine heart beat location and/or act as an alternative source for R-peak data. In some embodiments, temperature data may be provided via an alternative sensor channel. This data can be used in conjunction with other metrics of activity to discern activity type, level, and/or sleep. In some embodiments, the alternative data channel may provide information from a clock, for example the time of day or an indication of daytime or nighttime. In certain embodiments, the alternative data channel may be provided by a microphone/stethoscope, providing an audible recording of heart beat. Lastly, an alternative data channel may be provided by a flex or bend sensor which may allow for identification of motion artifacts.

Figure 14:
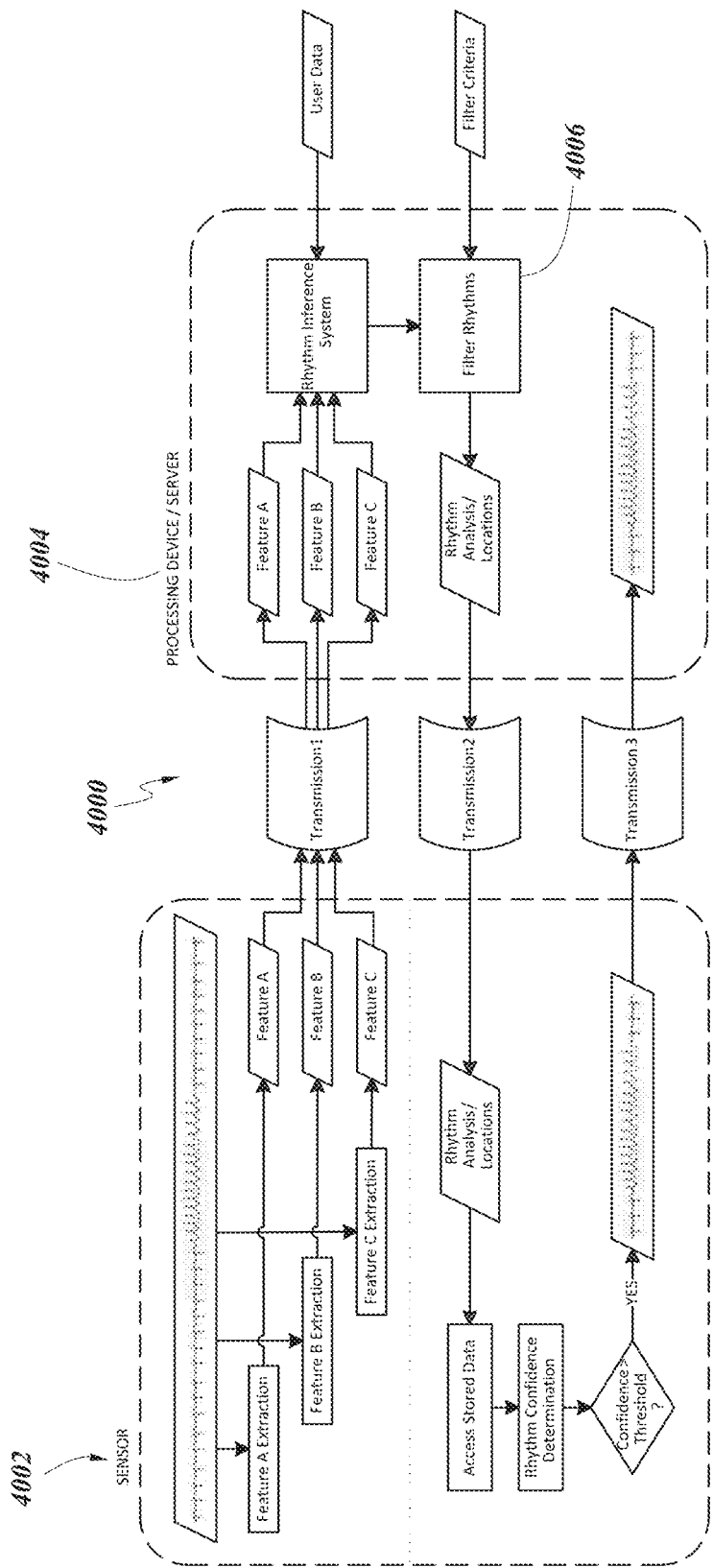
FIG. 14 is a schematic diagram of an embodiment of a physiological monitoring system incorporating data filters.

FIG. 14 is a schematic illustration of an embodiment of a system and method 4000 for a wearable ECG and/or medical sensor 4002 with transmission capabilities, very similar to the system and/or methods described above in relation to FIGS. 11 to 13. FIG. 14 differs from FIGS. 11 to 13 because the embodiment of FIG. 14 incorporates additional data filters. In some embodiments, the Processing Device 4004 may also filter rhythms 4006 identified by the rhythm inference system 4008 by applying filter criteria that may derive from multiple sources. For example, filter criteria may be drawn from: physician interest in timely reporting of particular rhythm types, physician interest in viewing a rhythm similar to one that was viewed previously (for example if multiple 3-second pauses were already reported to the physician, changing the threshold of interest to 4- or 5-seconds). In certain embodiments, filtering may include automated filtering to limit repeated retrieval of similar rhythm types and durations. Automated filtering can limit repeated retrieval of low positive-predictivity events, for example, a record with high levels of motion artifact where positive predictivity of the rhythm inference engine was low, and may allow automating filtering on subsequent requests. Such an approach may utilize confidence intervals assigned by the Rhythm inference system as well as the tracked history of rhythm inference system positive predictivity for a given monitoring session.

Figure 15:
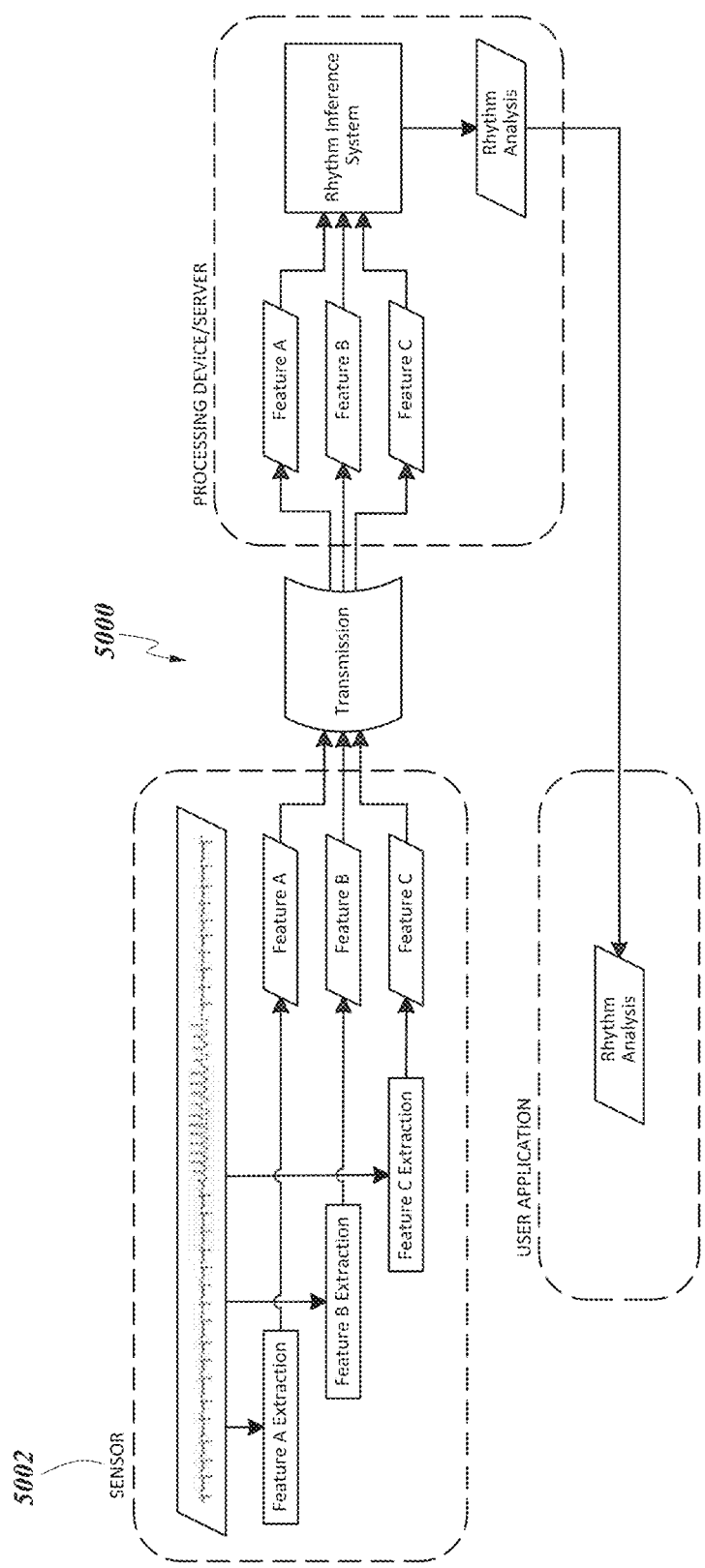
FIG. 15 is a schematic diagram of an embodiment of a wearable device system.

FIG. 15 is a schematic illustration of an embodiment of a system 5000 for a consumer wearable device without full ECG detection, with some similarities to the medical sensors of FIGS. 10 to 14. The sensors 5002 need not be medical-grade ECG sensors, but merely allow detection of beats. In embodiments, the sensor 5002 may continuously sense a data channel from which heart beat locations can be derived. Possible data sources include: PPG (optionally with multiple channels to increase accuracy), bio-impedance, and ECG without full implementation due to insufficient signal quality as compared to the sensors of FIGS. 10 to 14. Similar to the devices of FIGS. 10 to 14, features may be extracted from this signal, for example: R-peak locations, R-peak overflow flag, saturation flag, breathing rate, P/T wave locations, R-peak amplitude (or proxy), or ECG signal amplitude proxy. The data extraction may be performed via any method described herein this section or elsewhere in the specification. In certain embodiments, other channels of data are collected to improve confidence in rhythm assessments. The consumer device system 5000 further transmits and processes data via any method described herein this section or elsewhere in the specification. Based on these determinations, the results of the rhythm analysis may be sent to a user.

The consumer device system 5000 without full ECG sensing advantageously enables arrhythmia analysis using consumer-available heart-rate sensors, thereby reducing the cost and increasing the availability of the device. Consequently, this may enable arrhythmia screening on a larger population, including via over-the-counter screening.

Figure 16:
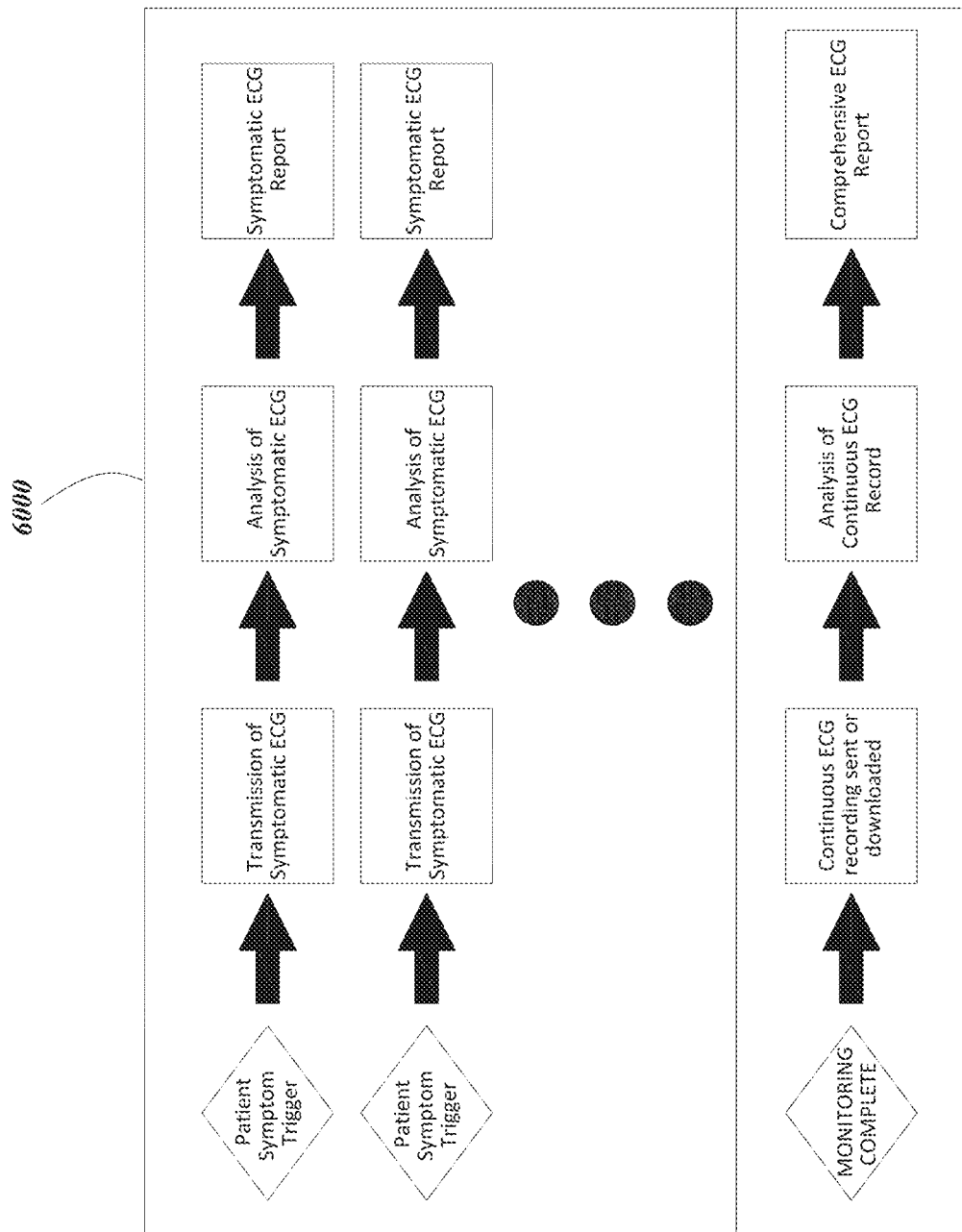
FIG. 16 is a schematic diagram of an embodiment of a symptomatic transmission system.

FIG. 16 is a schematic diagram of an embodiment of an ECG monitor system 6000 with symptomatic transmission. Such a system would involve a wearable ECG sensor, similar to the sensors described in relation to FIGS. 1 to 14. As described above, such a sensor senses and records ECG continuously. Each symptom trigger by a patient may initiate transfer of an ECG data strip. The data strip may vary in temporal location as well as duration, and may be centered around a triggered event. In certain embodiments, the data strip may be biased towards a time period prior to symptom trigger or it may be biased towards time period after symptom trigger. The data strip may be of a duration as short as a few heartbeats (~5-10 seconds), or of 60-90 second duration, or longer still (~5-20 minutes). In embodiments, the data strip duration may be dynamically changed, either programmatically based on clinical need or auto-adjusting based on patient trigger frequency. The ECG data strip may be transmitted via any of the means disclosed herein this section or elsewhere in the specification. If transmission is enabled without need for patient intervention (for example not NFC or wired transmission), data transfer may initiate automatically and opportunistically without requiring further patient interaction beyond symptom trigger.

The location for data strip analysis may vary. For example, analysis may occur local to the patient on a smartphone, tablet or PC. Alternatively, analysis may occur local to the clinic on a server or other processing device, or analysis may occur local to the ECG analysis service provider on a server or other processing device. Lastly, in embodiments, the analysis may occur using cloud-based distributed processing resources. In certain embodiments, a report may be provided for each symptomatic ECG data strip, however, a report may not be provided if the symptomatic ECG data strip is not determined to be clinically interesting. In some cases, the report may be made available, but notification to the user may be limited to those cases of particular clinical relevance. Offering this option can limit the demands on a user's time.

In certain embodiments, the report may be delivered in a variety of ways. For example, the report may be delivered: through a website, through a smartphone, tablet or PC application, through an Electronic Health Record (EMR/EHR) system with interoperability and integration into multiple providers' systems, or through automatic messaging such as email, SMS, app-based messaging. The recipient of the report may vary, in some applications the report recipient may be the patient-user while in other applications, the report recipient may be a clinician.

In particular embodiments, when monitoring is complete, the patient removes the device and sends the complete continuous ECG record to a data processing location. The method of sending may vary, for example, it may be sent via physical transfer of the entire device, such as mail or bringing the device to the prescribing clinic or it may be sent via local download of data and subsequent download to a data processing location. In some cases, the patient may not wait to remove the device before sending a partial segment of the continuous ECG record, this would be enabled by transfer methods that do not require removal of the device, for example NFC or ultra-low-power wireless data transfer. As with symptomatic ECG analysis described above, the data processing location may vary.

Figure 17:
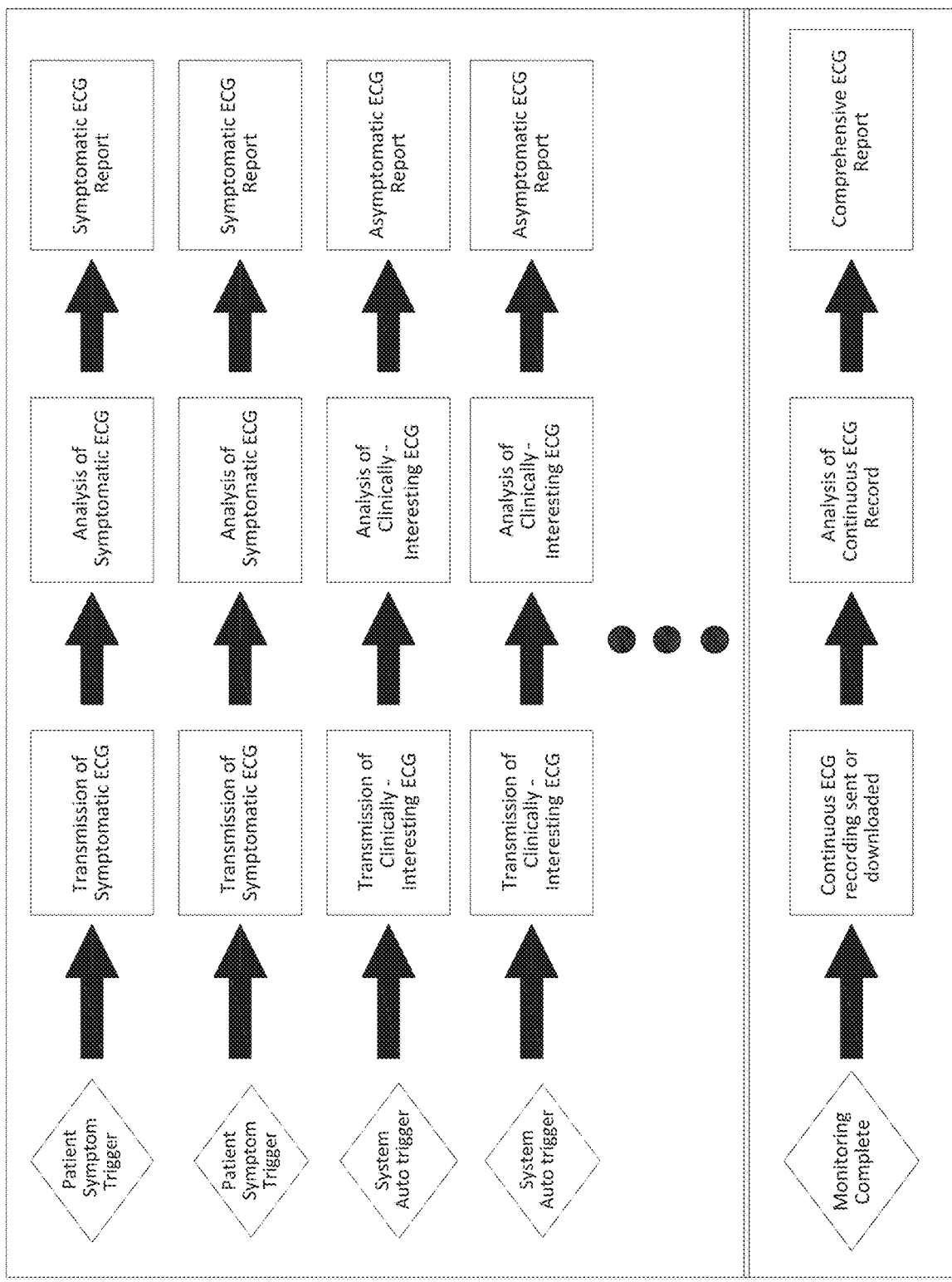
FIG. 17 is a schematic diagram of an embodiment of an asymptomatic transmission system.

FIG. 17 is a schematic diagram of an embodiment of an ECG monitor system 7000 with both symptomatic and asymptomatic transmission. The wearable sensor is similar to the sensors described herein this section or elsewhere in the specification. However, in embodiments, each asymptomatic trigger initiates transfer of an ECG data strip such as described above. Further physical features of the physiological monitoring device described herein this section or elsewhere in the specification facilitate implementation as described. As with the other embodiments described above, high-fidelity ECG recording, as enabled by the designs detailed herein this section or elsewhere in the specification, allows increased confidence in the accuracy of the feature extraction.

Computing Systems and Methods

Figure 18:
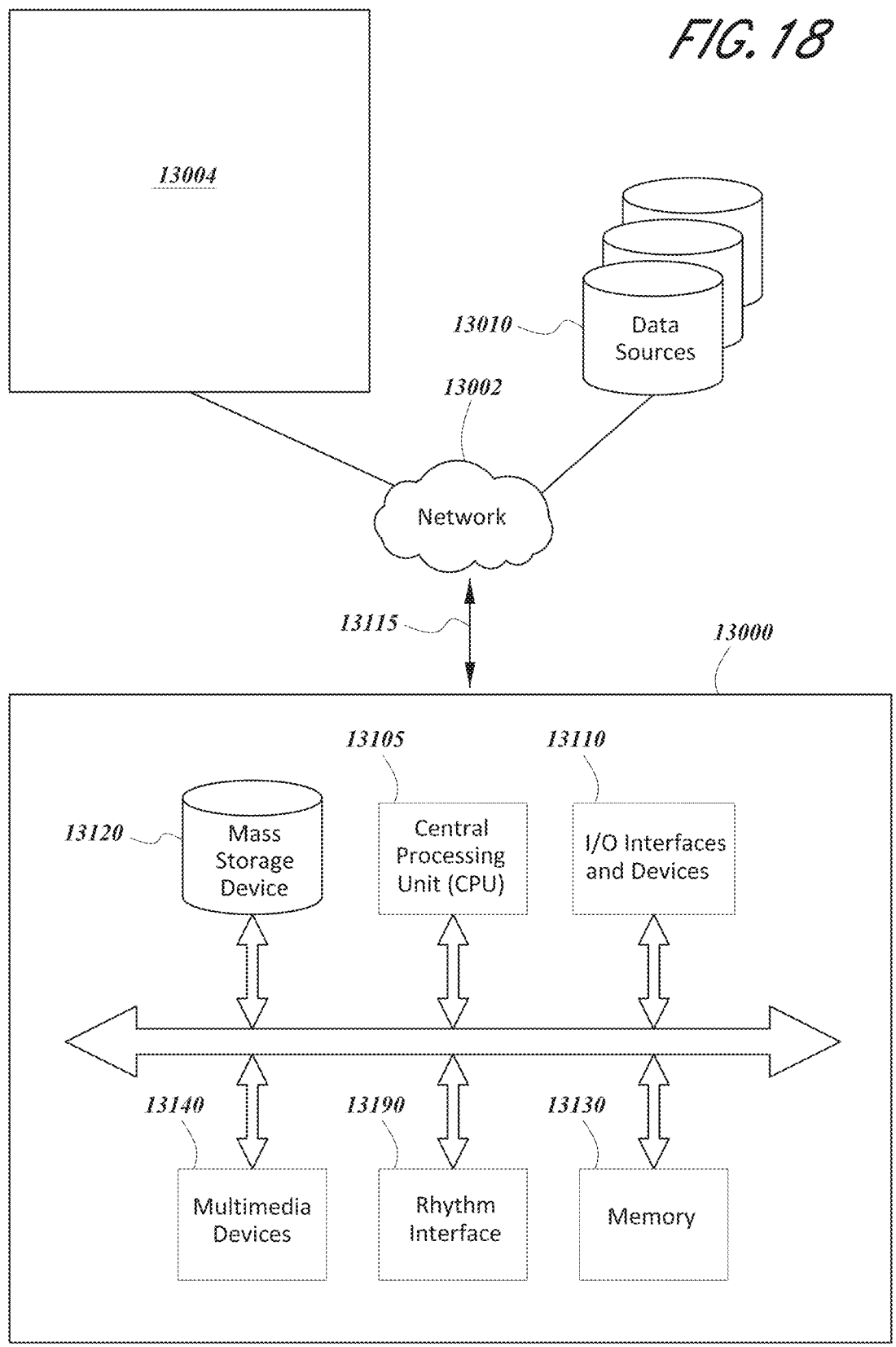
FIG. 18 is a schematic diagram of an embodiment of a computer network system.

In some embodiments, the systems, tools and methods of using same described above enable interactivity and data collection performed by a computing system 13000. FIG. 18 is a block diagram showing an embodiment in which the computing system 13000 is in communication with a network 13002 and various external computing systems 13004, such as a wearable system 13005, a gateway device 13006, which are also in communication with the network 13002. The computing system 13000 may be used to implement systems and methods described herein. While the external system 13004 are shown as grouped it is recognized that each of the systems may be external from each other and/or remotely located.

In some embodiments, the computing system 13000 includes one or more computing devices, for example, a server, a laptop computer, a mobile device (for example, smart phone, smart watch, tablet, personal digital assistant), a kiosk, automobile console, or a media player, for example. In one embodiment, the computing device 13000 includes one or more central processing units (CPUs) 13105, which may each include a conventional or proprietary microprocessor. The computing device 13000 further includes one or more memory 13130, such as random access memory (RAM) for temporary storage of information, one or more read only memory (ROM) for permanent storage of information, and one or more mass storage device 13120, such as a hard drive, diskette, solid state drive, or optical media storage device. In certain embodiments, the processing device, cloud server, server or gateway device, may be implemented as a computing system 1300. In one embodiment, the modules of the computing system 13000 are connected to the computer using a standard based bus system. In different embodiments, the standard based bus system could be implemented in Peripheral Component Interconnect (PCI), Microchannel, Small Computer computing system Interface (SCSI), Industrial Standard Architecture (ISA) and Extended ISA (EISA) architectures, for example. In addition, the functionality provided for in the components and modules of computing device 13000 may be combined into fewer components and modules or further separated into additional components and modules.

The computing device 13000 may be controlled and coordinated by operating system software, for example, iOS, Windows XP, Windows Vista, Windows 7, Windows 8, Windows 10, Windows Server, Embedded Windows, Unix, Linux, Ubuntu Linux, SunOS, Solaris, Blackberry OS, Android, or other operating systems. In Macintosh systems, the operating system may be any available operating system, such as MAC OS X. In other embodiments, the computing device 13000 may be controlled by a proprietary operating system. Conventional operating systems control and schedule computer processes for execution, perform memory management, provide file system, networking, I/O services, and provide a user interface, such as a graphical user interface (GUI), among other things.

The exemplary computing device 13000 may include one or more I/O interfaces and devices 13110, for example, a touchpad or touchscreen, but could also include a keyboard, mouse, and printer. In one embodiment, the I/O interfaces and devices 13110 include one or more display devices (such as a touchscreen or monitor) that allow visual presentation of data to a user. More particularly, a display device may provide for the presentation of GUIs, application software data, and multimedia presentations, for example. The computing system 13000 may also include one or more multimedia devices 13140, such as cameras, speakers, video cards, graphics accelerators, and microphones, for example.

The I/O interfaces and devices 13110, in one embodiment of the computing system and application tools, may provide a communication interface to various external devices. In one embodiment, the computing device 13000 is electronically coupled to a network 13002, which comprises one or more of a local area network, a wide area network, and/or the Internet, for example, via a wired, wireless, or combination of wired and wireless, communication link 13115. The network 13002 can communicate with various sensors, computing devices, and/or other electronic devices via wired or wireless communication links.

Figure 19:
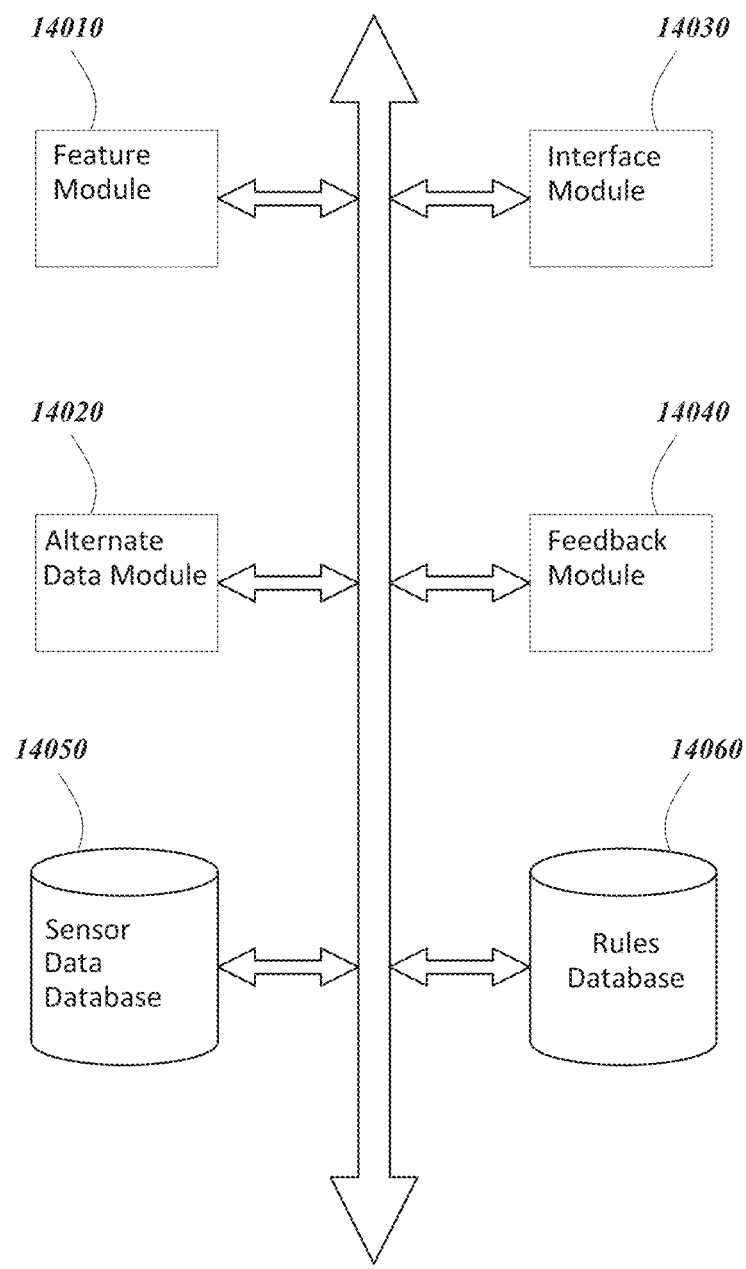
FIG. 19 is a schematic diagram of an embodiment of a programming and distribution module.

In some embodiments, the filter criteria, signals and data are processed by rhythm inference module an application tool according to the methods and systems described herein, may be provided to the computing system 13000 over the network 13002 from one or more data sources 13010. The data sources may include one or more internal and/or external databases, data sources, and physical data stores. The data sources 13010, external computing systems 13004 and the rhythm interface module 13190 may include databases for storing data (for example, feature data, raw signal data, patient data) according to the systems and methods described above, databases for storing data that has been processed (for example, data to be transmitted to the sensor, data to be sent to the clinician) according to the systems and methods described above. In one embodiment of FIG. 19, the sensor data 14050 may, in some embodiments, store data received from the sensor, received from the clinician, and so forth. The Rules Database 14060 may, in some embodiments, store data (for example, instructions, preferences, profile) that establish parameters for the thresholds for analyzing the feature data. In some embodiments, one or more of the databases or data sources may be implemented using a relational database, such as Sybase, Oracle, CodeBase, MySQL, SQLite, and Microsoft® SQL Server, and other types of databases such as, for example, a flat file database, an entity-relationship database, and object-oriented database, NoSQL database, and/or a record-based database.

The computing system, in one embodiment, includes a rhythm interface module 13190 that may be stored in the mass storage device 13120 as executable software codes that are executed by the CPU 13105. The rhythm interface module 13190 may have a Feature Module 14010, an Alternate Data Module 14020, an Inference Module 14030, a Feedback Module 14040, a Sensor Data Database 14050, and a Rules Database 14060. These modules may include by way of example, components, such as software components, object-oriented software components, subroutines, segments of program code, drivers, firmware, microcode, circuitry, data, databases, data structures, tables, arrays, and variables. These modules are also configured to perform the processes disclosed herein including, in some embodiments, the processes described with respect to FIGS. 10 to 17.

In general, the word "module," as used herein, refers to logic embodied in hardware or firmware, or to a collection of software instructions, possibly having entry and exit points, written in a programming language, such as, for example, Python, Java, Lua, C and/or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the computing system 13000, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The block diagrams disclosed herein may be implemented as modules. The modules described herein may be implemented as software modules, but may be represented in hardware or firmware. Generally, the modules described herein refer to logical modules that may be combined with other modules or divided into sub-modules despite their physical organization or storage.

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The term "including" means "included but not limited to." The term "or" means "and/or."

Any process descriptions, elements, or blocks in the flow or block diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be at least partially embodied in, and partially or fully automated via, software code modules executed by one or more computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. For example, a feature of one embodiment may be used with a feature in a different embodiment. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of a physiological monitoring device, methods, and systems are disclosed herein. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Various modifications to the implementations described in this disclosure may be made, and the generic principles defined herein may be applied to other implementations without departing from the spirit or scope of this disclosure. Thus, the scope of the disclosure is not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, the separation of various system components in the embodiments described above should not be interpreted as requiring such separation in all embodiments. Additionally, other embodiments are within the scope of the following claims. In some cases, the actions recited in the claims can be performed in a different order and still achieve desirable results.

What is claimed is:

1. A method of monitoring the physiological data of a mammal using a wearable monitor, comprising:
    applying a wearable patch to the skin of the mammal, the wearable patch comprising a hardware processer within a first adhesive assembly, the first adhesive assembly comprising a plurality of electrodes configured to detect or derive cardiac signals;
    within the hardware processor, continuously storing cardiac signals from the mammal;
    wirelessly transmitting the cardiac signals to a computing system;
    within the computing system, analyzing the cardiac signals to infer a likelihood of a cardiac arrhythmia originating in the past;
    after a period of wear, detaching the wearable patch from the surface of the mammal; and
    applying a second adhesive assembly to the skin of the mammal.

2. The method of claim 1, wherein the first adhesive assembly and the second adhesive assembly each comprise a rigid housing and a plurality of flexible wings, each flexible wing comprising an electrode.

3. The method of claim 1, wherein the computing system comprises a gateway.

4. The method of claim 1, wherein the first adhesive assembly and the second adhesive assembly each comprise a battery.

5. The method of claim 1, wherein the first adhesive assembly and the second adhesive assembly each comprise a transmitter, the transmitter configured to wirelessly transmit the cardiac signals to the computing system.

6. The method of claim 1, wherein the period of wear is less than one week.

7. The method of claim 1, wherein the cardiac signals transmitted to the computing system contain about a one hour increment of data.

8. A method of monitoring the physiological data of a mammal using a wearable monitor, comprising:
    applying a wearable patch to the skin of the mammal, the wearable patch comprising a hardware processer within a first adhesive assembly, the first adhesive assembly comprising a plurality of electrodes configured to detect or derive cardiac signals;
    within the hardware processor, continuously storing cardiac signals from the mammal;
    wirelessly transmitting the cardiac signals to a computing system;
    analyzing the cardiac signals to infer a likelihood of a cardiac arrhythmia originating in the past;
    after a period of wear, detaching the wearable patch from the surface of the mammal;
    removing the hardware processor from the wearable patch;
    inserting the hardware processor into a second adhesive assembly; and
    applying the second adhesive assembly to the skin of the mammal.

9. The method of claim 8, wherein the first adhesive assembly and the second adhesive assembly each comprise a rigid housing and a plurality of flexible wings, each flexible wing comprising an electrode.

10. The method of claim 8, wherein the computing system comprises a gateway.

11. The method of claim 8, further comprising modifying the hardware processor while it is removed from the patch.

12. The method of claim 8, wherein the cardiac signals are transmitted to the computing system on a periodic basis.

13. The method of claim 8, wherein the cardiac signals are continuously transmitted to the computing system.

14. A method of monitoring the physiological data of a mammal using a wearable monitor, comprising:
    applying a wearable patch to the skin of the mammal, the wearable patch comprising a hardware processer within a first adhesive assembly, the first adhesive assembly comprising a plurality of electrodes configured to detect or derive cardiac signals;
    within the hardware processor, continuously storing cardiac signals from the mammal;
    wirelessly transmitting the cardiac signals to a computing system;

analyzing the cardiac signals to infer a likelihood of a cardiac arrhythmia originating in the past;

after a period of wear, detaching the wearable patch from the surface of the mammal; and applying a second adhesive assembly to the skin of the mammal.

15. The method of claim 14, wherein the first adhesive assembly and the second adhesive assembly each comprise a rigid housing and a plurality of flexible wings, each flexible wing comprising an electrode.

16. The method of claim 14, wherein the computing system comprises a gateway.

17. The method of claim 14, wherein the first adhesive assembly and the second adhesive assembly each comprise a battery.

18. The method of claim 14, wherein the first adhesive assembly and the second adhesive assembly each comprise a transmitter, the transmitter configured to wirelessly transmit the cardiac signals to the computing system.

19. The method of claim 14, wherein the period of wear is less than one week.

20. The method of claim 14, wherein the episode of likely past cardiac arrhythmia comprises at most about a 20 minute increment of time.

* * * * *